(12) United States Patent
Yoo

(10) Patent No.: US 11,318,136 B2
(45) Date of Patent: May 3, 2022

(54) IDENTIFICATION OF GRANINS AS THE PATHOGENIC FACTOR OF ALZHEIMER'S DISEASE AND COMPOSITIONS AND METHODS FOR INHIBITING GRANIN AGGREGATION AND TREATING ALZHEIMER'S DISEASE

(71) Applicant: Seung Hyun Yoo, Plano, TX (US)

(72) Inventor: Seung Hyun Yoo, Plano, TX (US)

( * ) Notice: Subject to any disclaimer, the term of this patent is extended or adjusted under 35 U.S.C. 154(b) by 0 days.

(21) Appl. No.: 16/382,786

(22) Filed: Apr. 12, 2019

(65) Prior Publication Data

US 2019/0314375 A1    Oct. 17, 2019

Related U.S. Application Data

(60) Provisional application No. 62/657,601, filed on Apr. 13, 2018.

(51) Int. Cl.
| | | |
|---|---|---|
| *A61K 31/517* | (2006.01) | |
| *A61P 25/28* | (2006.01) | |
| *A61K 31/7076* | (2006.01) | |
| *A61K 31/7056* | (2006.01) | |
| *A61K 31/352* | (2006.01) | |

(52) U.S. Cl.
CPC .......... *A61K 31/517* (2013.01); *A61K 31/352* (2013.01); *A61K 31/7056* (2013.01); *A61K 31/7076* (2013.01); *A61P 25/28* (2018.01)

(58) Field of Classification Search
CPC ................ A61K 31/353; A61K 31/517; A61K 31/7056; A61P 25/28
See application file for complete search history.

(56) References Cited

U.S. PATENT DOCUMENTS

| | | |
|---|---|---|
| 2009/0163580 A1 | 6/2009 | Yatcilla et al. |
| 2010/0069481 A1 | 3/2010 | Cohen |
| 2011/0111014 A1 | 5/2011 | Langston |
| 2012/0071550 A1 | 3/2012 | Zelkha et al. |
| 2015/0065449 A1* | 3/2015 | Bienkiewicz .......... A61K 31/05  514/52 |
| 2016/0175349 A1* | 6/2016 | Hasegawa ............ A61K 36/185  424/682 |
| 2016/0199437 A1* | 7/2016 | Wilson ..................... C07K 7/06  424/130.1 |

FOREIGN PATENT DOCUMENTS

| | | | |
|---|---|---|---|
| JP | 2013241354 A | * 12/2013 | |
| WO | WO-2009087568 A2 | * 7/2009 | ............. A61P 25/00 |
| WO | 2017/031300 A1 | 2/2017 | |

OTHER PUBLICATIONS

Mira (Molecules vol. 20 pp. 4813-4823. Published 2015). (Year: 2015).*
Reiter (Journal of Pineal Research vol. 61 pp. 253-269 published 2016) (Year: 2016).*
Kim (Biosci Biotechnol. Biochem vol. 74 pp. 397-401. Published 2010) (Year: 2010).*
International Search Report dated Jul. 24, 2019 for related PCT/KR2019/004409.
Lechner, Theresa et al.; "Chromogranin peptides in Alzheimer's disease"; Experimental Gerontology; 2004; vol. 39; pp. 101-113.
Taupenot, Laurent et al..; "The chromogranin-secretogranin family"; The New England Journal of Medicine; 2003; vol. 348, No. 12; pp. 1134-1149.
International Preliminary Report on Patentability dated Oct. 13, 2020 with a Translation of the Written Opinion of the International Searching Authority in Application No. PCT/KR2019/004409.
Extended European Search Report dated May 27, 2021 for related European Patent Application No. 19784322.0.
Willis, Michael et al.; "Chromogranin peptides in brain diseases"; Journal of Neural Transmission; Springer-Verlag, VI, vol. 118, No. 5; Apr. 30, 2011; pp. 727-735 (XP019901441).

* cited by examiner

*Primary Examiner* — Theodore R. Howell
*Assistant Examiner* — George W Kosturko
(74) *Attorney, Agent, or Firm* — Sughrue Mion, PLLC

(57) ABSTRACT

Compositions for inhibiting the aggregation of a granin from a non-toxic low molecular weight form to a toxic high molecular weight aggregated form and/or dissociating a high molecular weight aggregated form to a low molecular weight form are provided. Such a composition typically includes one or more active compounds or agents, which may also be referred to herein as disaggregation compounds. Using the compounds and compositions described herein, methods of i) modulating, inhibiting or preventing the interaction of granins with metal ions, ii) modulating, inhibiting, preventing the aggregation of granins or dissociating aggregated granins, iii) reducing or inhibiting cell toxicity, iv) treating or preventing dementia or Alzheimer's disease, and v) preventing or treating Parkinson's and/or Huntington's diseases are also provided.

8 Claims, 60 Drawing Sheets

Frontal Section of Granin-injected Rat Brain

Bar = 100 μm

Bar = 50 μm

Bar = 50 μm

IDENTIFICATION OF GRANINS AS THE PATHOGENIC FACTOR OF ALZHEIMER'S DISEASE AND COMPOSITIONS AND METHODS FOR INHIBITING GRANIN AGGREGATION AND TREATING ALZHEIMER'S DISEASE

BACKGROUND

The following includes information that may be useful in understanding the present inventions. It is not an admission that any of the information provided herein is prior art, or relevant, to the presently described or claimed inventions, or that any publication or document that is specifically or implicitly referenced is prior art.

The brains of Alzheimer's disease (AD) patients are known to possess protein aggregates called senile plaques, and the clinical severity of Alzheimer's patients is directly tied to these plaques (Glass et al., 2010; Heneka et al., 2010, 2015). Hence the past efforts to find cures for AD have mainly focused on the study of these senile plaques; trying to find the components of senile plaques and devise ways of either inhibition of the formation of senile plaques or disruption and/or reduction of the already-formed plaques by interfering with aggregation of the protein components of the plaques (Glass et al., 2010; Heneka et al., 2010, 2015). The major components of senile plaques identified are beta-amyloid (Aβ) and granins (chromogranins and secretogranins) (Heneka et al., 2010, 2015, Willis et al., 2008, 2011). Beta-amyloids found in senile plaques consist of ~42 amino acids while the granin proteins consist mostly of ~430-700 amino acids (Bartolomucci et al., 2011; Helle, 2000; Taupenot et al., 2003).

Traditionally almost all the efforts to find cures for Alzheimer's disease have centered on beta-amyloid (Aβ) without any success (Doody et al., 2014; Glass et al., 2010; Heneka et al., 2010, 2015; Salloway et al., 2014). As a result, humans are helplessly exposed to this deadly disease without any remedy, and the annual worldwide expenditure related to AD treatment amounts to ~US $1 trillion. Despite the dire global situation there are currently no promising drugs to combat the disease in the pipeline even after ~30 years of extensive efforts worldwide (Doody et al., 2014; Salloway et al., 2014). This dead-end appears to have caused by a narrow approach in the world-wide efforts to find cures for Alzheimer's disease, focusing mostly on Aβ, a minor component of senile plaques, as the primary target protein.

Indeed, the hallmark of Alzheimer's disease (AD) is the presence of extracellular aggregates of brain proteins, known as senile plaques, in the brain interstitium (Glass et al., 2010; Heneka et al., 2010, 2015). The senile plaques are composed of aggregates of brain proteins, i.e., granins and Aβ (Heneka et al., 2010, 2015, Willis et al., 2008, 2011). Of these, granins are markedly larger than Aβ and much more abundant in the brain than Aβ (Bartolomucci et al., 2011; Helle, 2000; Taupenot et al., 2003). In this application, we not only identify that aggregated granins as the pathogenic factor, metal ions being the co-factor, of Alzheimer's disease but also point out that inhibition of metal-induced aggregation of granins can lead to prevention and at least partial cure of Alzheimer's disease. Accordingly, we report our experimental findings and inventions relating generally to compositions and methods for inhibiting granin aggregation and the toxicity of aggregated granins.

BRIEF SUMMARY

The inventions described and claimed herein have many attributes and embodiments including, but not limited to, those set forth or described or referenced in this Brief Summary. The inventions described and claimed herein are not limited to, or by, the features or embodiments identified in this Summary, which is included for purposes of illustration only and not restriction.

In this application, we studied the contribution of granins, the major component proteins of senile plaques, in the formation of senile plaques, and the potential roles of granins in the pathogenic developments of brain cells. This work led to the development of compositions for inhibiting the aggregation of a granin from a non-toxic low molecular weight form to a toxic high molecular weight aggregated form and/or dissociating a high molecular weight aggregated form to a low molecular weight form. Such a composition typically includes one or more active compound or agent referred to herein as a disaggregation compound.

One aspect described herein is to modulate, inhibit, or suppress the aggregation of a granin from a low molecular weight form to a high molecular weight aggregated form and/or to dissociate a high molecular weight aggregated form to a low molecular weight form.

More particularly, a composition for inhibiting the aggregation of a granin from a low molecular weight form to a high molecular weight aggregated form and/or dissociating a high molecular weight aggregated form to a low molecular weight form is provided. Such a composition typically includes one or more disaggregation compound that inhibits, prevents, or modulates the aggregation of a granin from a low molecular weight form to a high molecular weight aggregated form and/or dissociates a high molecular weight aggregated form to a low molecular weight form.

Certain anthoxanthin compounds described herein are preferred disaggregation compounds. Accordingly, certain embodiments provided herein are directed to methods of using the composition for inhibiting the interaction of granins with metal ions and/or the metal-induced aggregation of a granin, wherein the composition comprises one or more anthoxanthin as at least one disaggregation compound.

Another aspect provided herein is to modulate, inhibit, or suppress the aggregation of granins in the brain of an animal in order to reduce, inhibit, or suppress the pathogenesis of brain cells which leads to Alzheimer's disease and other neurodegenerative diseases.

In another aspect, methods of modulating, inhibiting or preventing the interaction of granins with metal ions are provided. In embodiments according to this aspect, a disaggregation compound is provided that inhibits, prevents, or modulates the interaction or binding of a granin with a metal ion or cofactor selected from $Zn^{2+}$, $Cu^{2+}$, $Fe^{2+}$ and $Ca^{2+}$.

In another aspect, a disaggregation compound provided herein reduces, inhibits, suppress or sequesters a metal ion selected from $Zn^{2+}$, $Cu^{2+}$, $Fe^{2+}$ and $Ca^{2+}$ to inhibit, prevent, or modulate the interaction or binding of a granin with the metal ion in the nervous system of an animal, and thereby functions to modulate, inhibit, or prevent the aggregation of a granin from a low molecular weight form to a high molecular weight aggregated form and/or to dissociate a high molecular weight aggregated form to a low molecular weight form.

In another aspect, methods of modulating, inhibiting, or preventing the aggregation of a granin from a low molecular weight form to a high molecular weight aggregated form and/or of dissociating a high molecular weight aggregated form to a low molecular weight form are provided.

In another aspect, a method of reducing or inhibiting cell toxicity is provided. In certain embodiments, the method comprises administering a composition for inhibiting the aggregation of a granin from a low molecular weight form to a high molecular weight aggregated form and/or dissociating a high molecular weight aggregated form to a low molecular weight form.

In another aspect a method for the treatment or prevention of dementia or Alzheimer's disease is provided. In certain embodiments, these methods use compositions for inhibiting the aggregation of a granin from a low molecular weight form to a high molecular weight aggregated form.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings.

Figure 1:
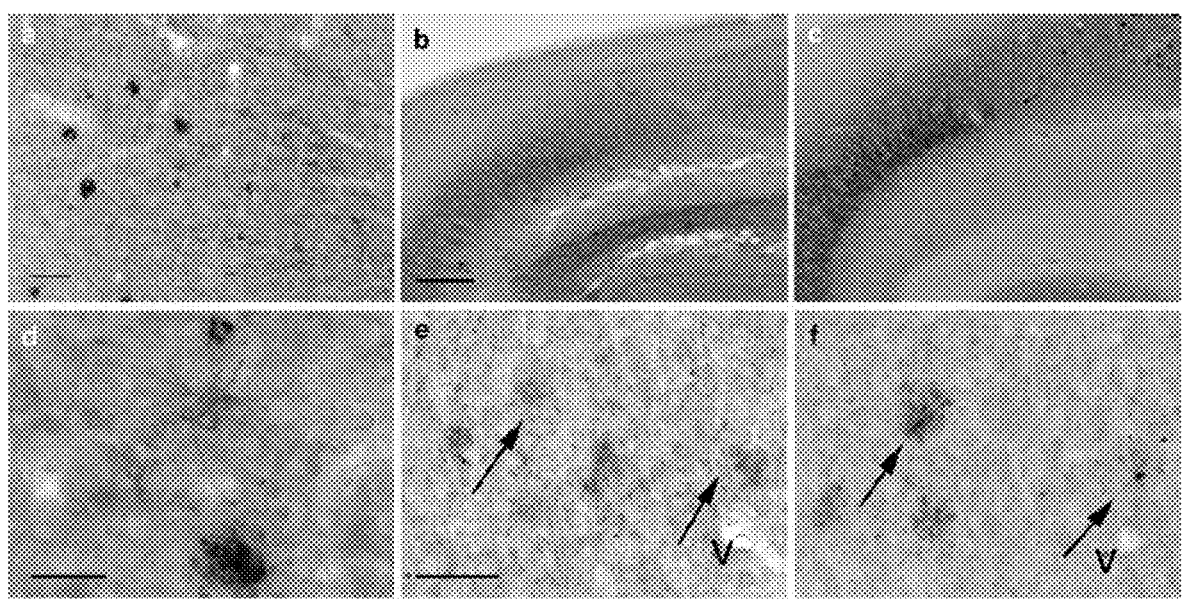
FIG. 1: Shows immunostaining (appears black in the pictures) of chromogranin A (a, d), secretogranin II (b, e), and chromogranin B (c, f) in the brain hippocampus of AD patient. Bar=100 µm (a), 200 µm (b, c), 40 µm (d), 80 µm (e, f).
Figure 2:
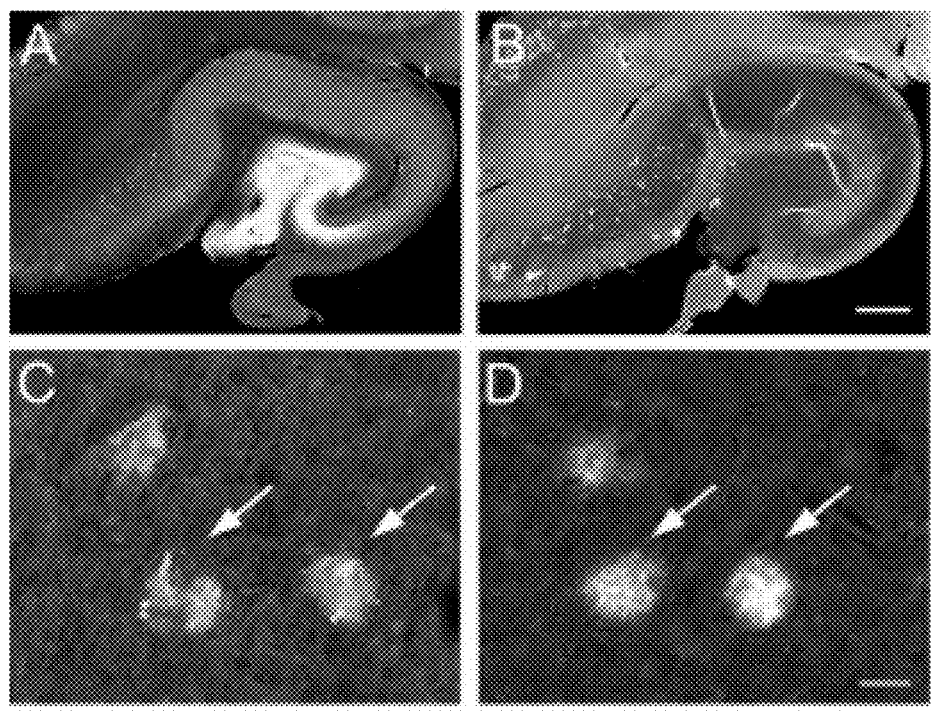
FIG. 2. Shows the presence of chromogranin B (A, C) and beta-amyloid (B, D) in the brain hippocampus of an Alzheimer's (AD) patient.
Figure 3:
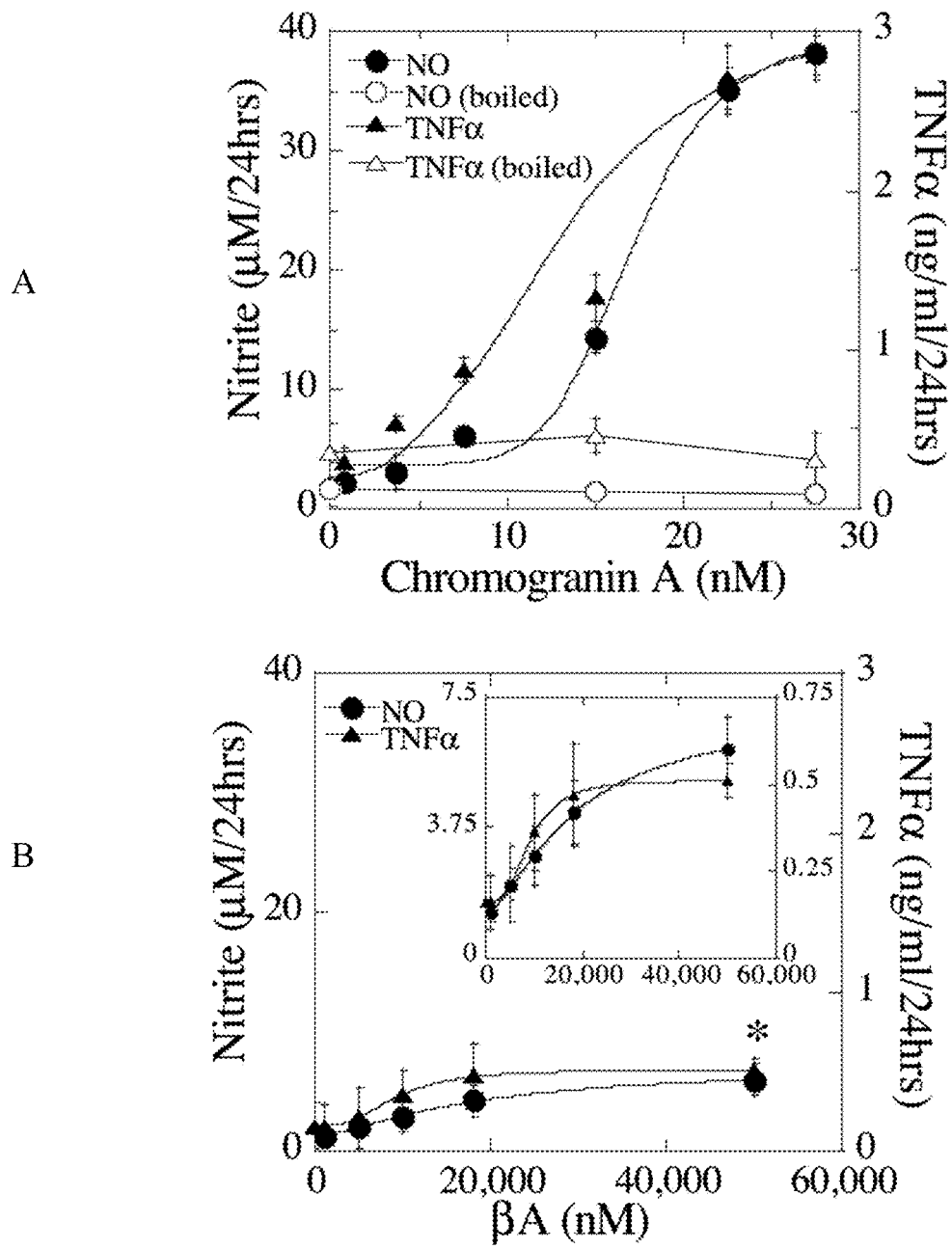
FIG. 3. Shows the dose-response effects of chromogranin A (CGA)-(panel A) and β-amyloid (Aβ)-(panel B) induced release of nitric oxide (NO) and tumor necrosis factor-α (TNFα) from brain immune cell microglia.

Four molecules were applied via intracerebroventricle injection methods as follows (shown left to right): Group 1 (control); 1 µl of 2 mM MOPS, pH 7.4 was injected into the intracerebroventricle of rat brain (7 rats). Group 2 (granins); 0.1 µM of CGA, CGB, and SgII each in 1 µl of 2 mM MOPS, pH 7.4 were injected into the intracerebroventricle of rat brain (9 rats). Group 3 (granins+metal ions); 0.1 µM of CGA, CGB, and SgII each plus 0.8 mM Cu2+, 250 µM Fe2+, and 2 mM of Zn2+, all in 1 µl of 2 mM MOPS, pH 7.4 were injected into the intracerebroventricle of rat brain (9 rats). Group 4 (granins+metal ions+4 kinds of flavonoids and stilbenoids); 0.1 µM of CGA, CGB, and SgII each, and 0.8 mM Cu2+, 250 µM Fe2+, and 2 mM of Zn2+, plus 1 µM each of 4 kinds of flavonoids, stilbenoids, and other molecules, all in 1 µl of 2 mM MOPS, pH 7.4 were injected into the intracerebroventricle of rat brain (8 rats).

Figure 30:
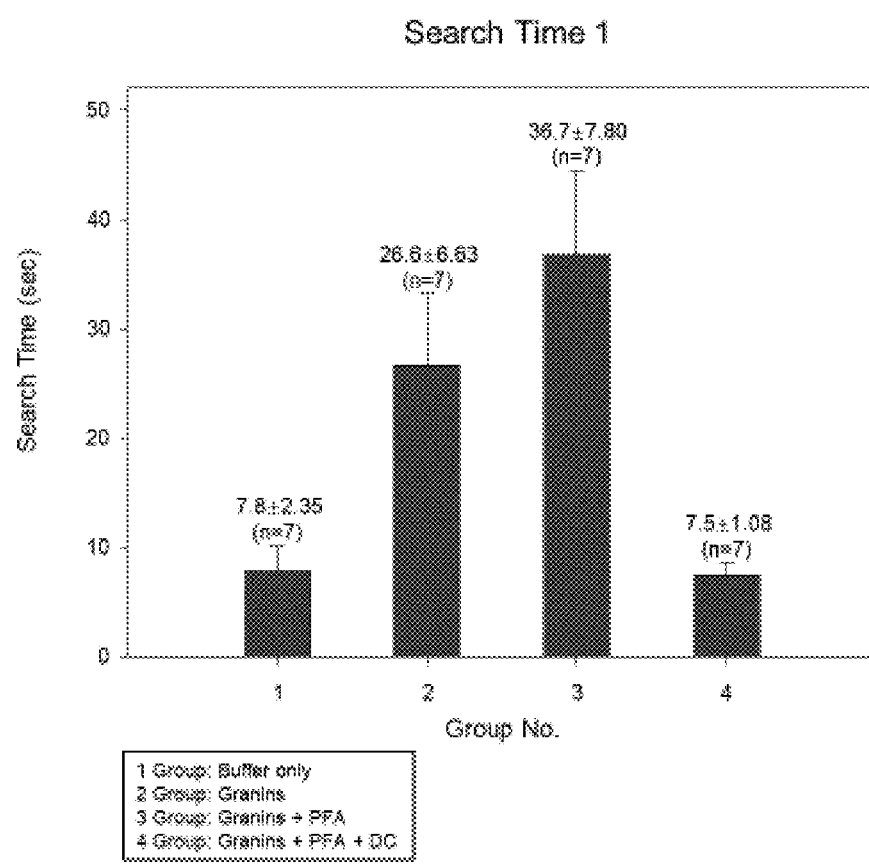

FIG. 30. Search time spent by rats in each group in Morris water maze test 1.5-mo after intraventricular injection. The average time (in seconds) spent by rats in each group to escape to the platform in Morris water maze test was expressed with standard error (n is the number of rats in each group).

Figure 31:
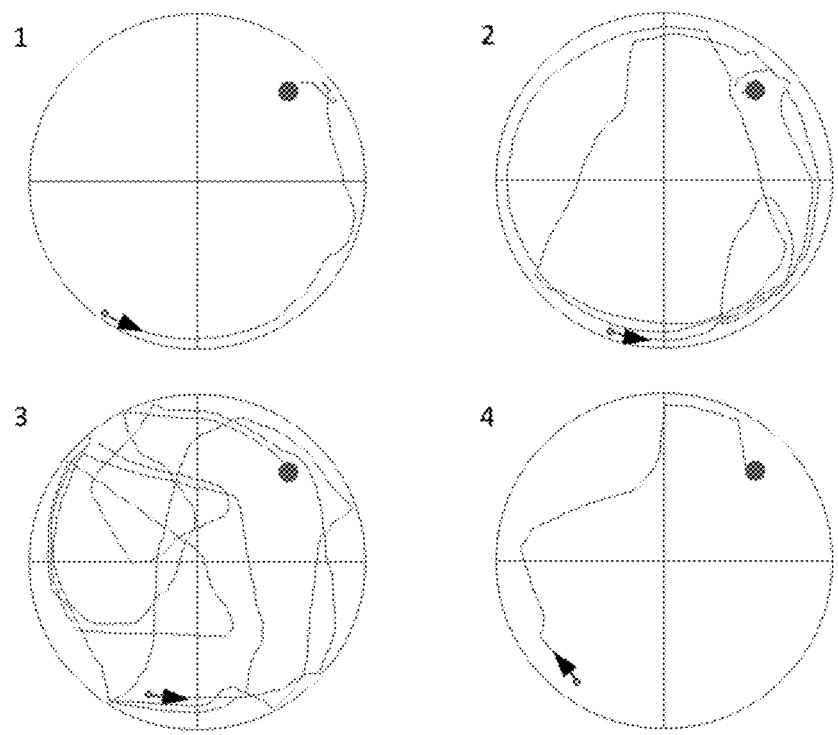

FIG. 31. Shows the representative swimming tracks of rats in different groups.

Figure 32:
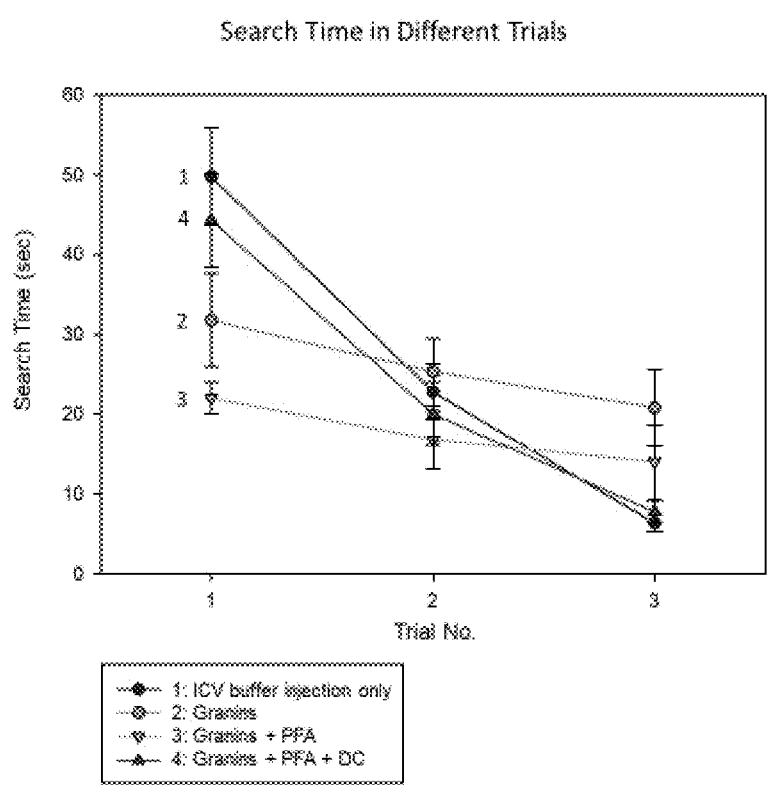

FIG. 32. Shows time spent to find the relocated platform. The numbers indicate group number, and the average times of search in seconds are expressed with standard error bars.

Figure 33:
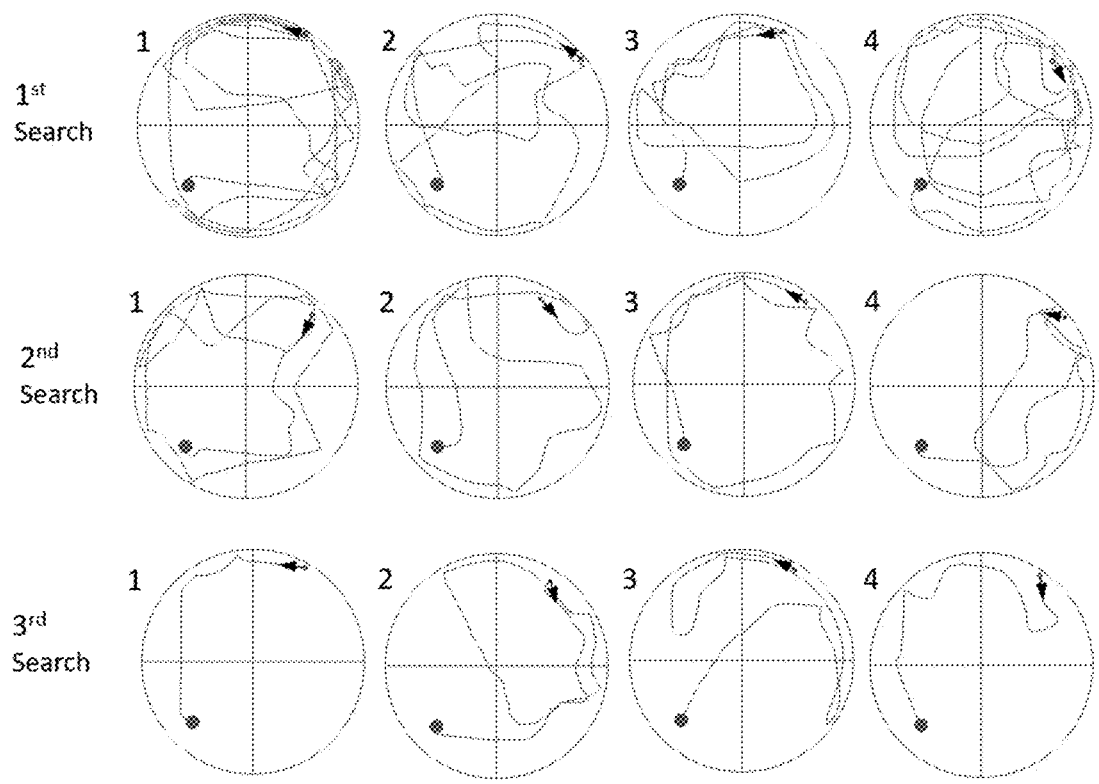

FIG. 33. Shows the representative swimming tracks of rats in each group are shown. The numbers at the top left indicate the group number and the traces show the swimming tracks of rats from each group. The small circles in the top right quadrants indicate where the rats started to swim to find the platform shown in large circles in the bottom left quadrants.

Figure 34:
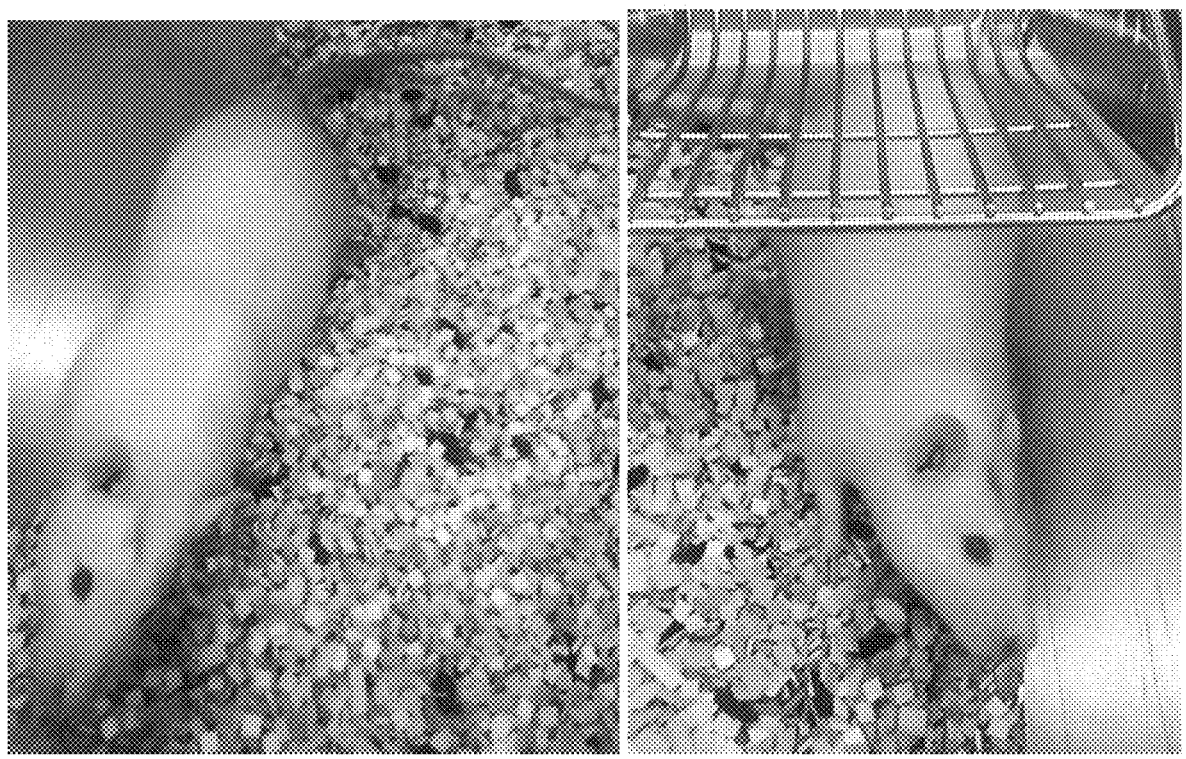

FIG. 34. Shows abnormal posture of some rats injected with granins. Some rats in group 3 showed skewed necks 2 weeks after the injection of granins plus metal ions (Cu2+, Zn2+, and Fe2+) while some rats in group 2 started to show skewed necks 4-5 weeks after the injection of granins. No rats in groups 1 and 4 exhibited any abnormal posture even after 35 weeks (~8 months).

Figure 35:
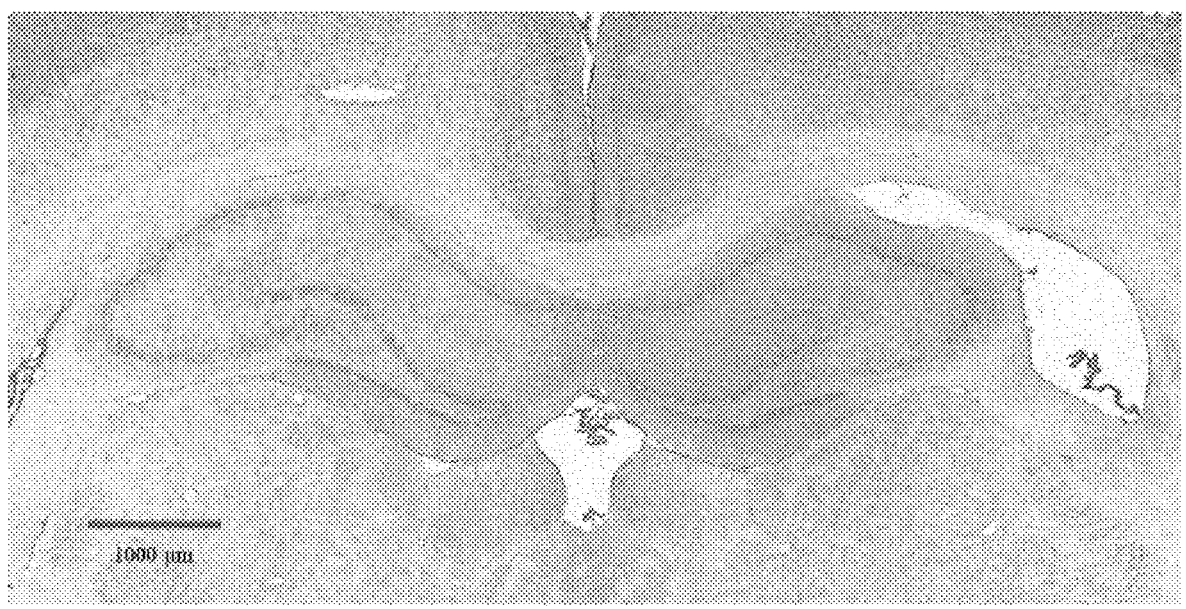

FIG. 35. Shows shrunken hippocampus (right half) of a rat with skewed neck in group 2 (injected with granins). A rat in group 2 (injected with granins) with skewed neck was sacrificed 10 weeks after the injection of granins (6 weeks after the manifestation of skewed neck and 6 months after birth) and the brain tissue was examined.

Figure 36:
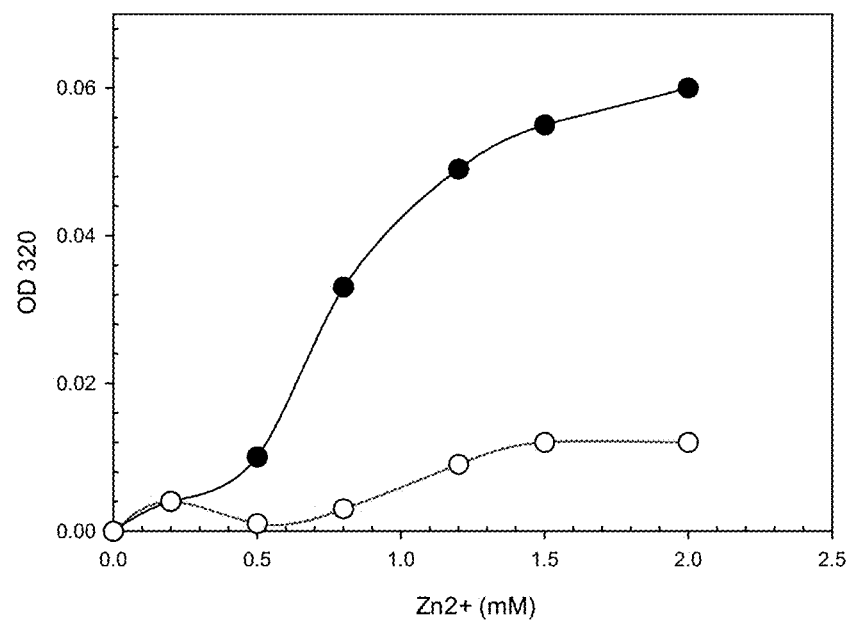

FIG. 36. Shows prevention of Zn2+-induced chromogranin B aggregation by apigenin.

Figure 37:
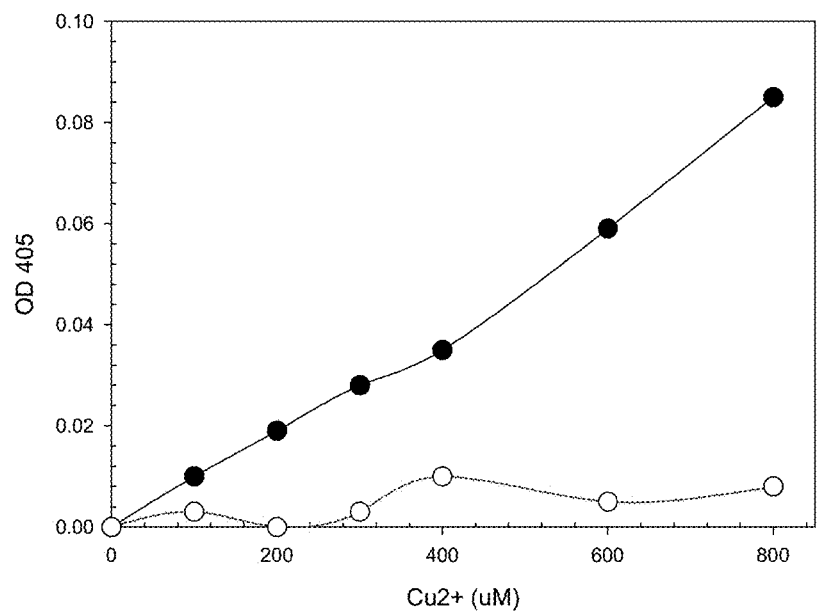

FIG. 37. Shows prevention of Cu2+-induced chromogranin A aggregation by apigenin.

Figure 38:
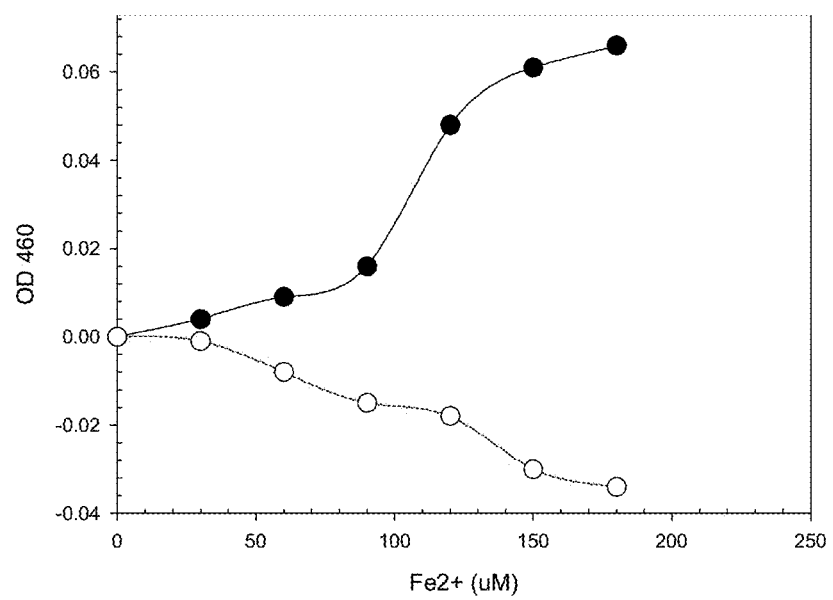

FIG. 38. Shows prevention of Fe2+-induced chromogranin B aggregation by tangeretin.

Figure 39:
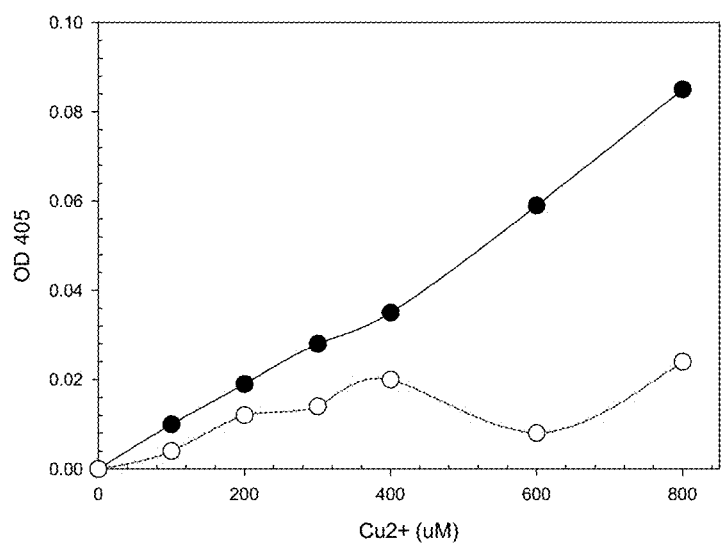

FIG. 39. Shows prevention of Cu2+-induced chromogranin A aggregation by tangeretin.

Figure 40:
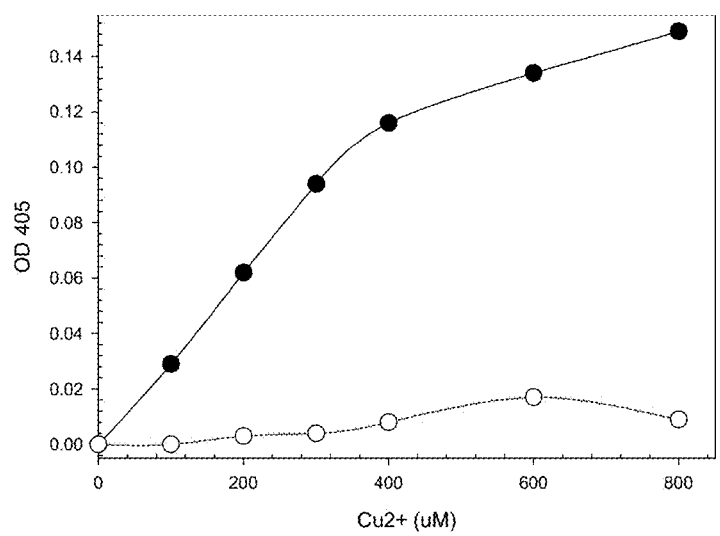

FIG. 40. Shows prevention of Cu2+-induced chromogranin B aggregation by quercetin.

Figure 41:
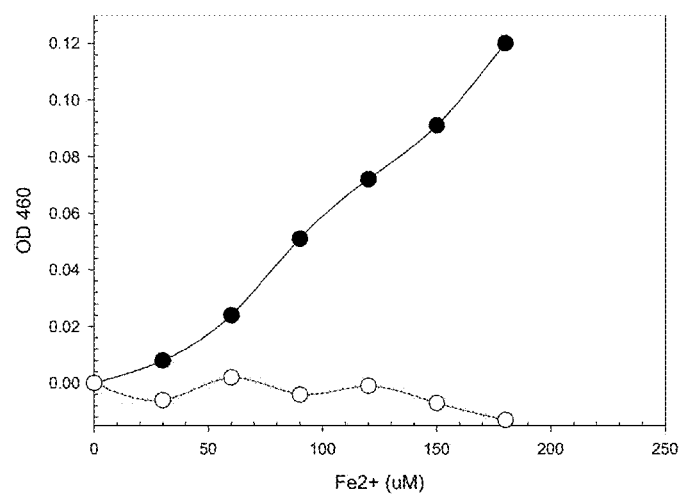

FIG. 41. Shows prevention of Fe2+-induced secretogranin II aggregation by quercetin.

Figure 42:
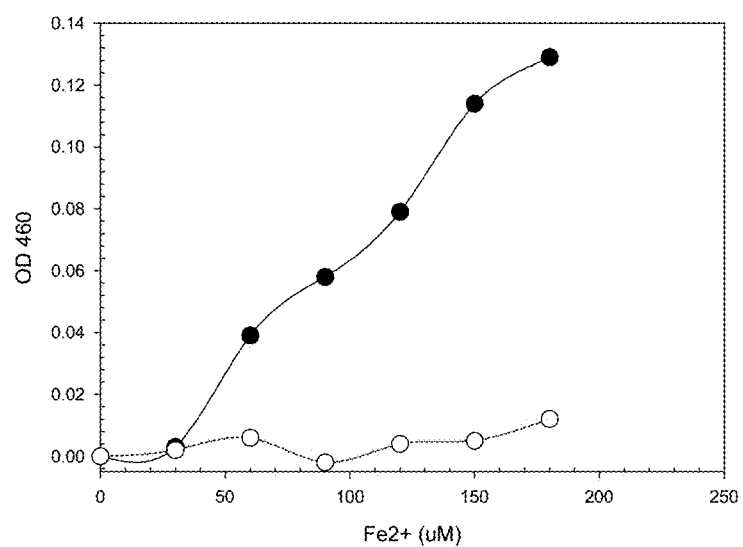

FIG. 42. Shows prevention of Fe2+-induced chromogranin A aggregation by fisetin.

Figure 43:
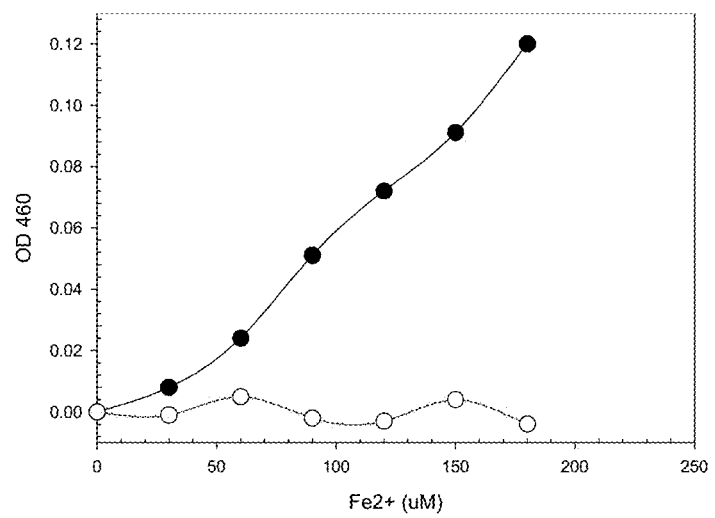

FIG. 43. Shows prevention of Fe2+-induced secretogranin II aggregation by fisetin.

Figure 44:
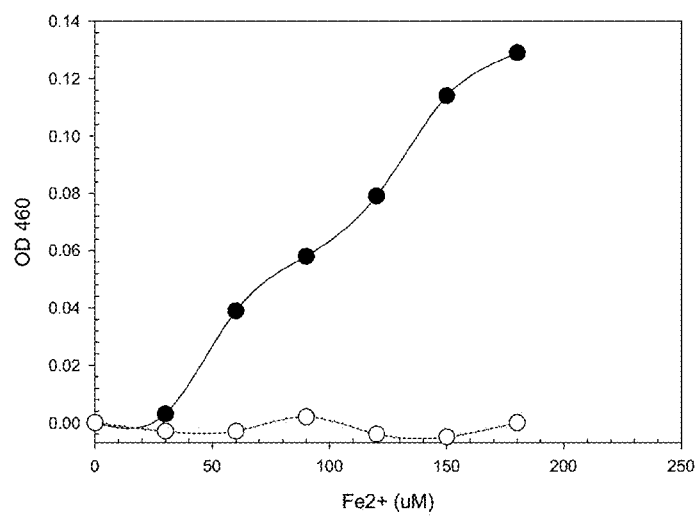

FIG. 44. Shows prevention of Fe2+-induced chromogranin A aggregation by myricetin.

Figure 45:
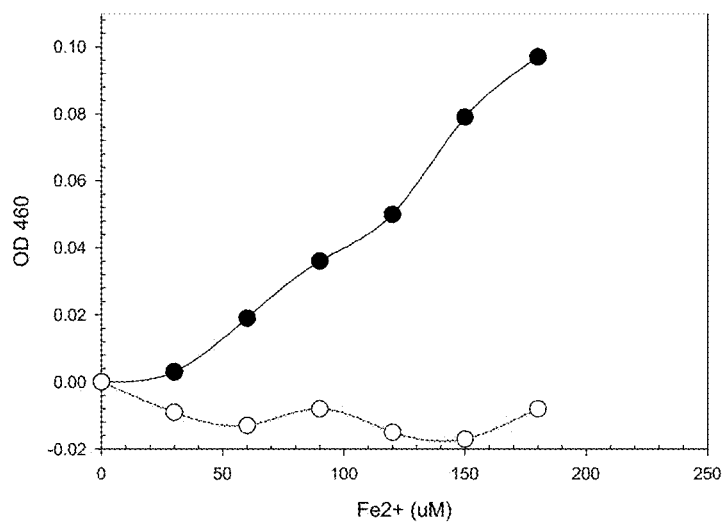

FIG. 45. Shows prevention of Fe2+-induced chromogranin B aggregation by myricetin.

Figure 46:
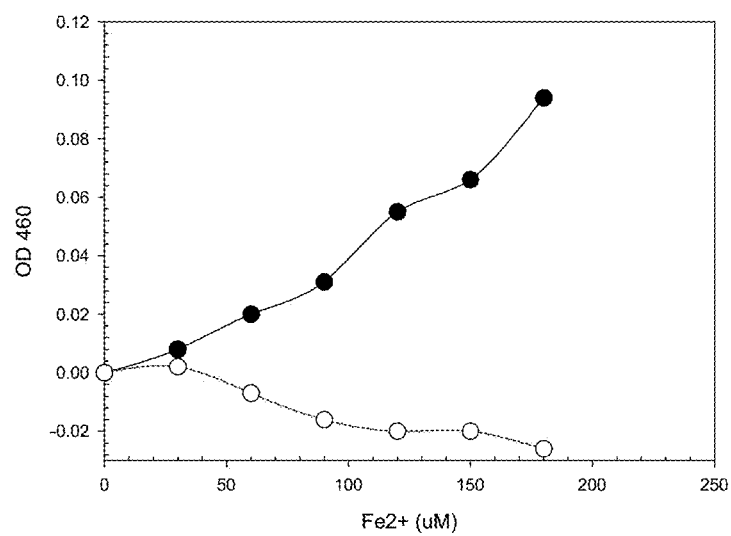

FIG. 46. Shows prevention of Fe2+-induced chromogranin A aggregation by morin.

Figure 47:
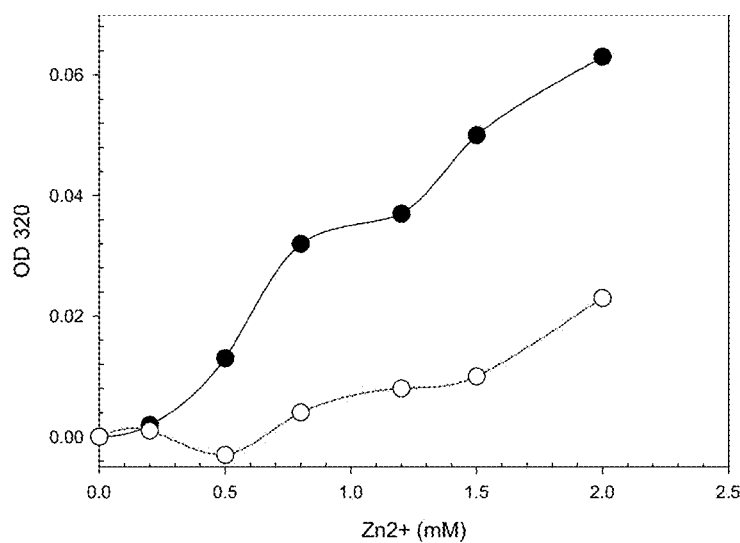

FIG. 47. Shows prevention of Zn2+-induced chromogranin A aggregation by morin.

Figure 48:
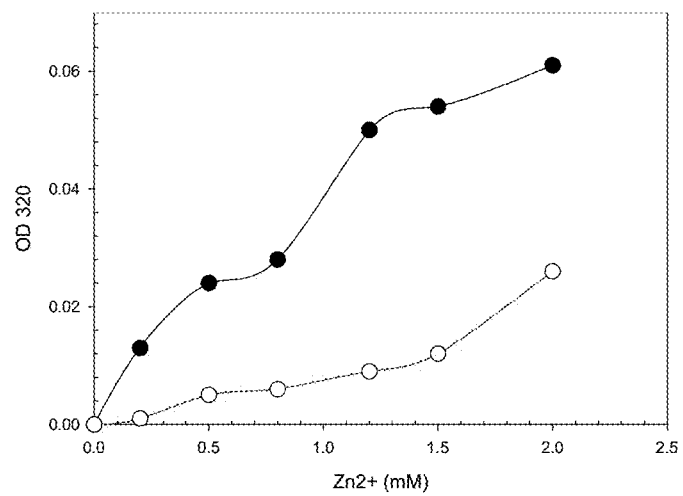

FIG. 48. Shows prevention of Zn2+-induced chromogranin A aggregation by 5,7-demethoxyflavone.

Figure 49:
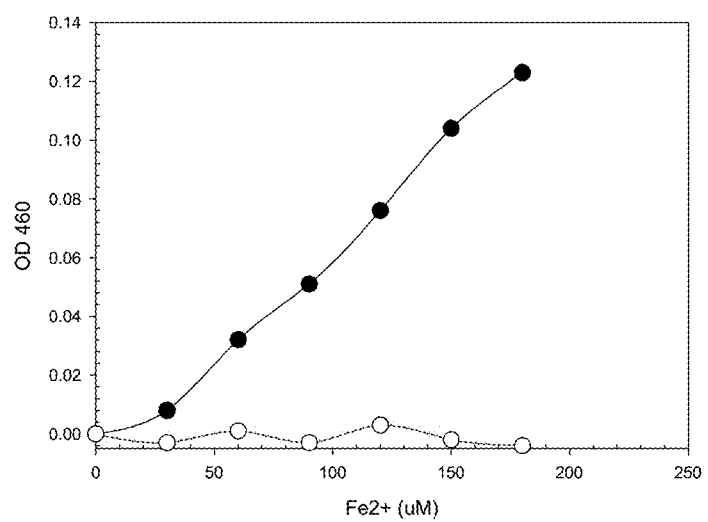

FIG. 49. Shows prevention of Fe2+-induced chromogranin A aggregation by 5,7-demethoxyflavone.

Figure 50:
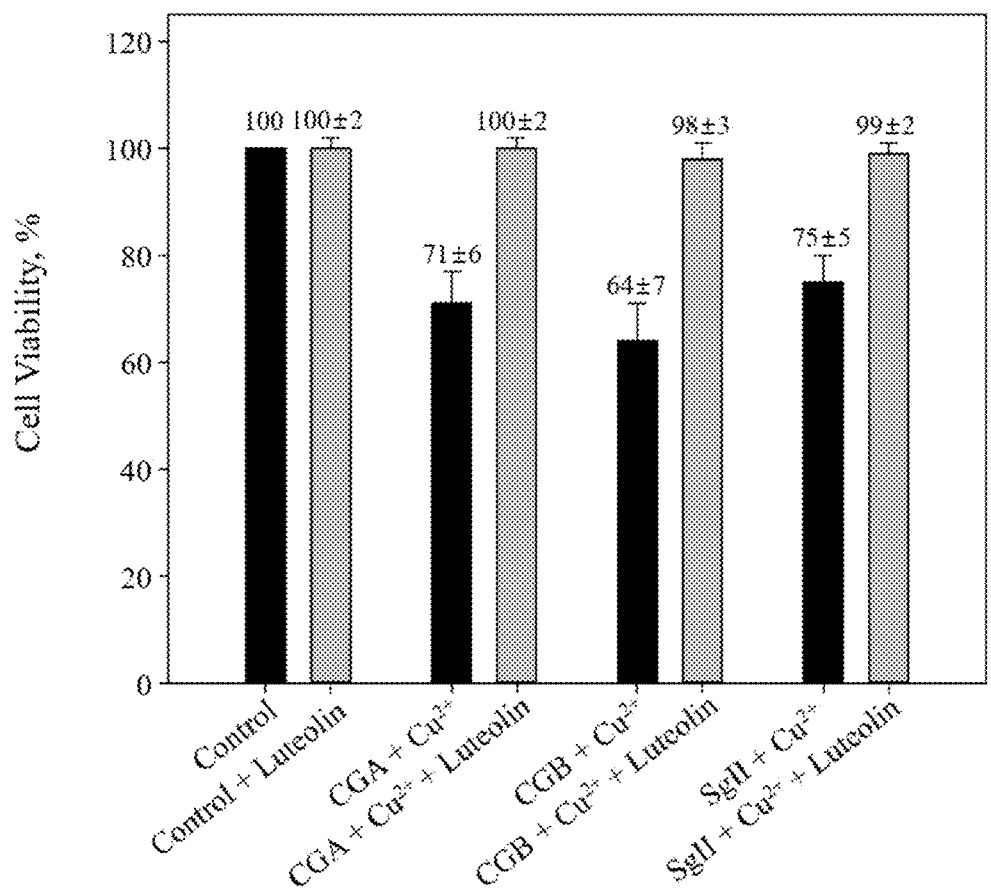

FIG. 50. Shows the cell toxicity of each granin in the presence of 20 µM Cu2+ and 1 µM toxicity inhibitor luteolin. The cell toxicity of each granin (0.1 µM chromogranin A, 0.06 µM chromogranin B, and 0.07 µM secretogranin II) in the presence of 20 µM Cu2+ and in the additional presence of 1 µM luteolin (cf. FIG. 13-14 above), one of the metal-induced granin toxicity inhibitors, was measured using PC12 cells and MTT assays (Cheruvara et al., 2015; Shearman et al., 1994). Luteolin, one of the inhibitors of metal-induced granin aggregation (see FIG. 13-14 above), virtually stopped the granin-induced toxicity.

Figure 51:
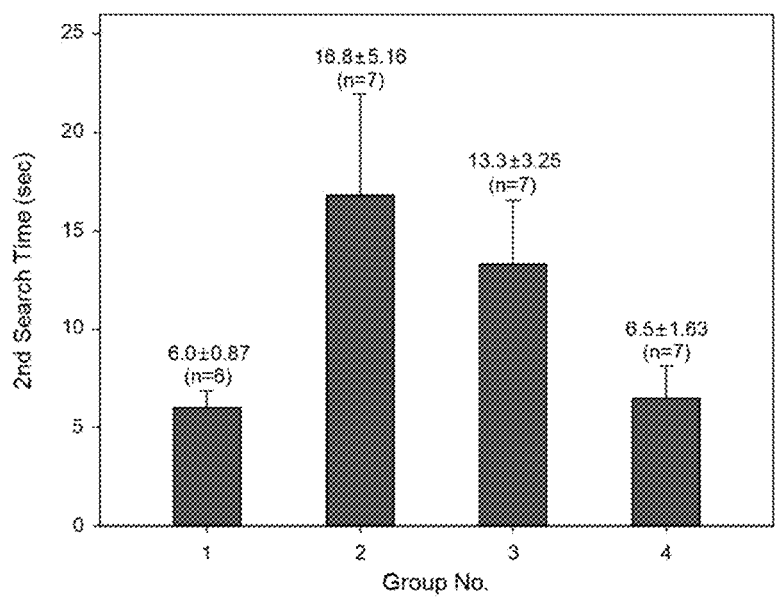

FIG. 51. Shows the search time spent by rats in each group in Morris water maze test 2.5-mo after intraventricular injection.

Figure 52:
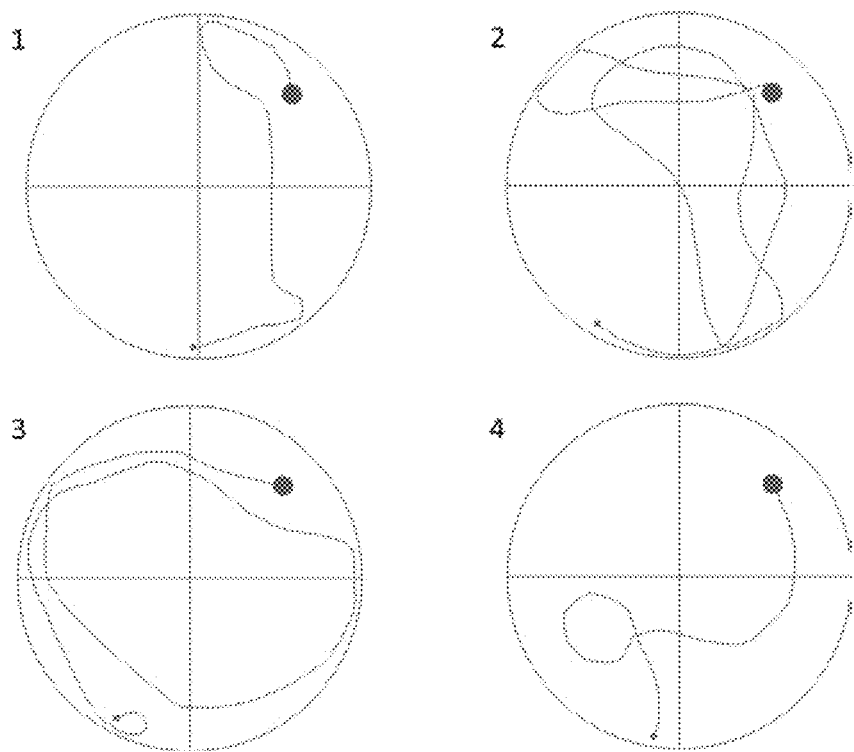

FIG. 52. Shows the representative swimming tracks of rats in each group from FIG. 51.

Figure 53A:
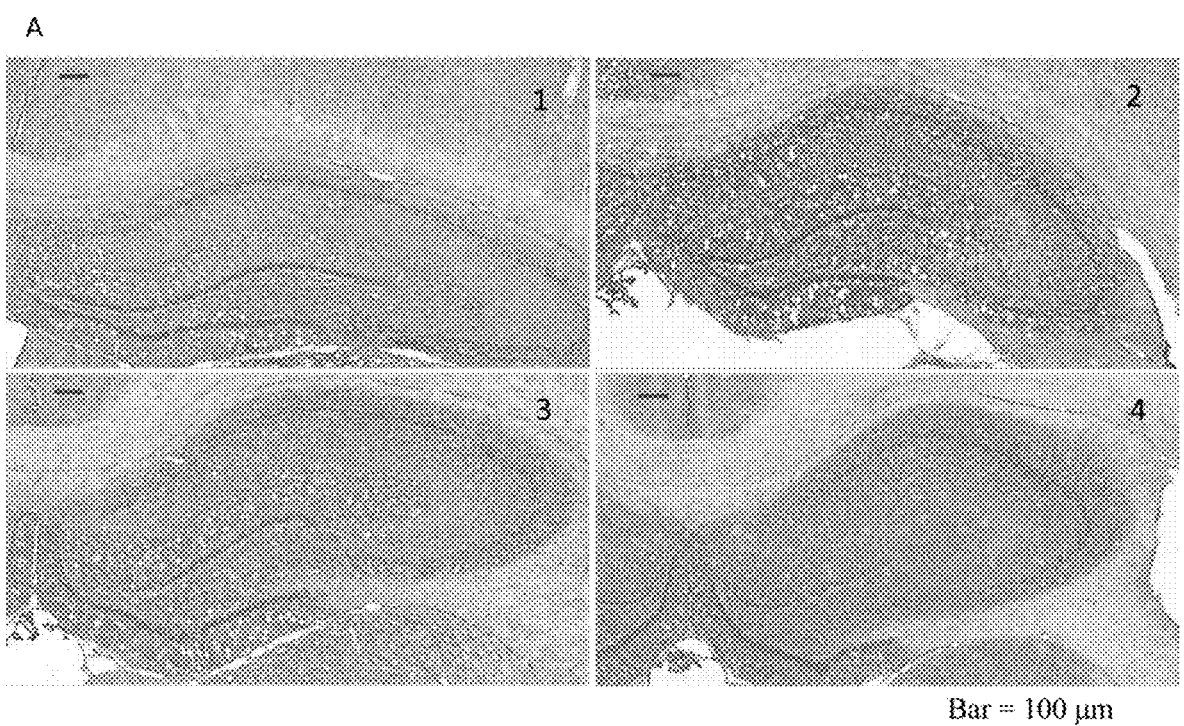

FIG. 53(a). Shows the brain hippocampus sections of 10.5 month old (7.5-mo after the granin injection) rats were stained with haematoxylin.

Figure 53B:
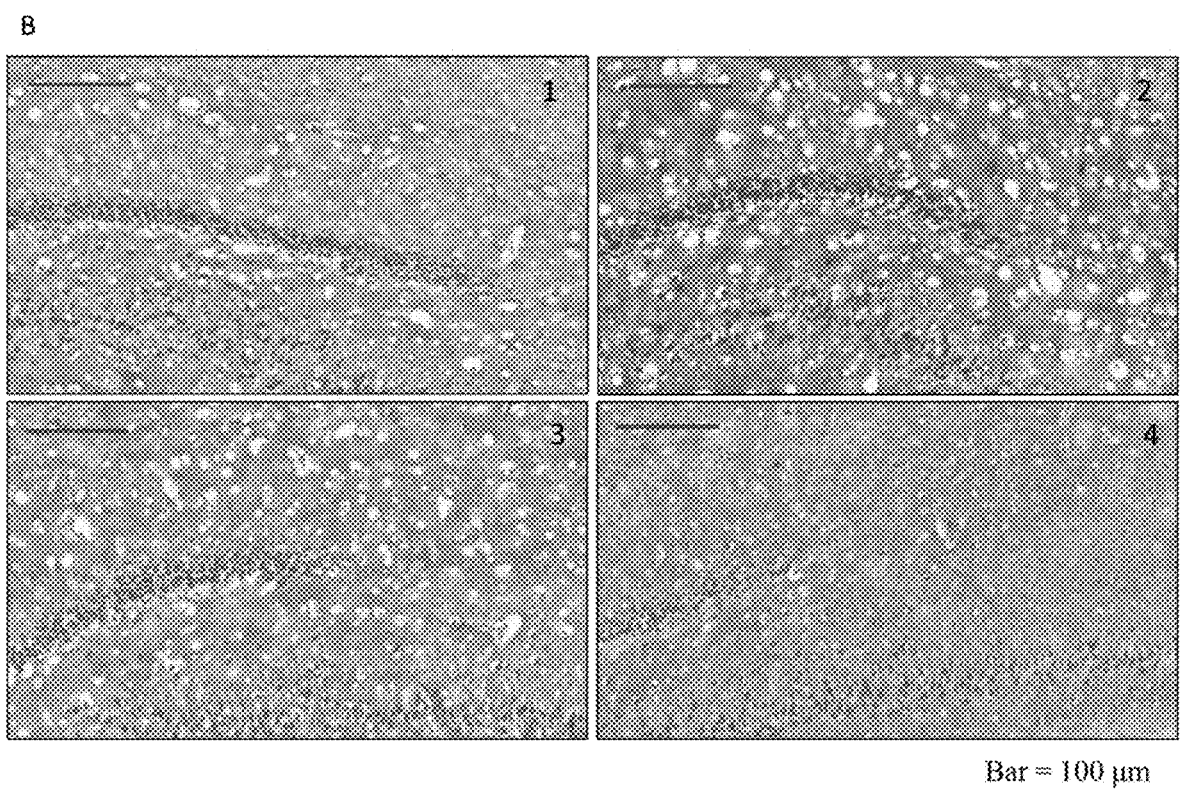

FIG. 53(b). Shows higher magnification views of approximately the same areas of hippocampus from 53(a).

Figure 54:
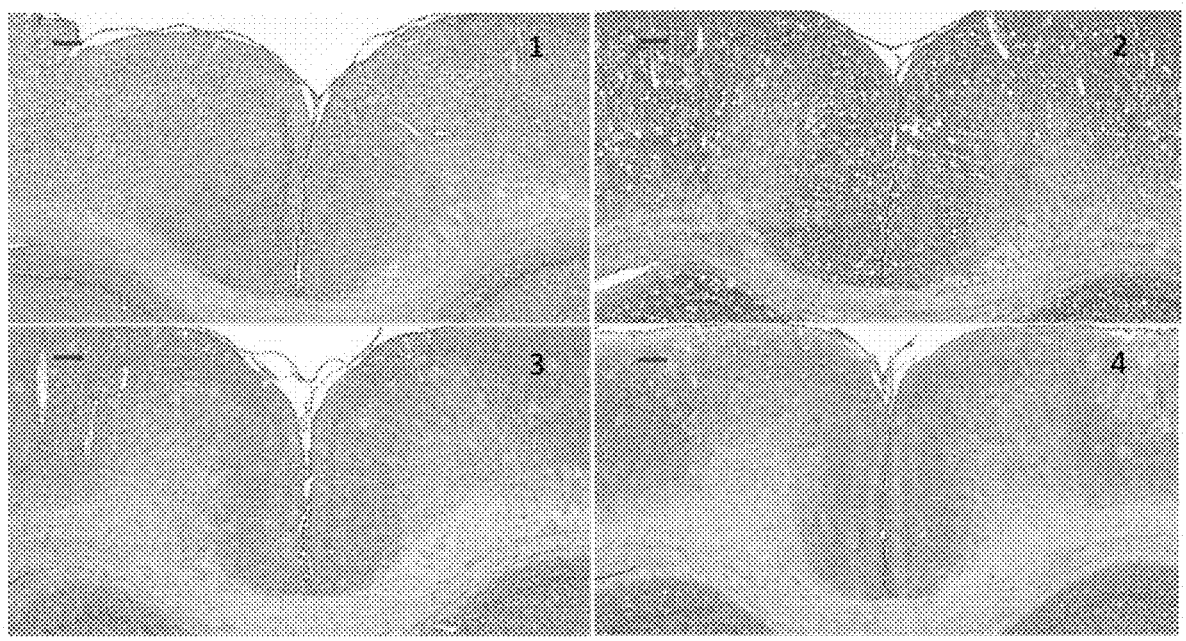

FIG. 54. Shows the frontal sections of the cortex from 10.5 month old rats with and without AD-like symptoms.

Figure 55:
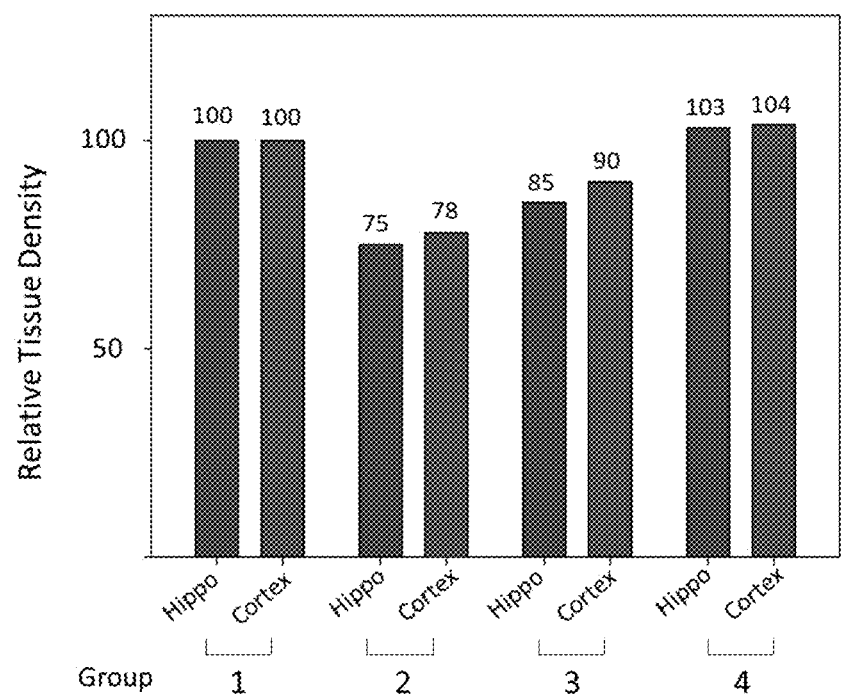

FIG. 55. Shows a comparison of the brain tissue density in 10.5 month old rats with and without AD-like symptoms.

Figure 56:
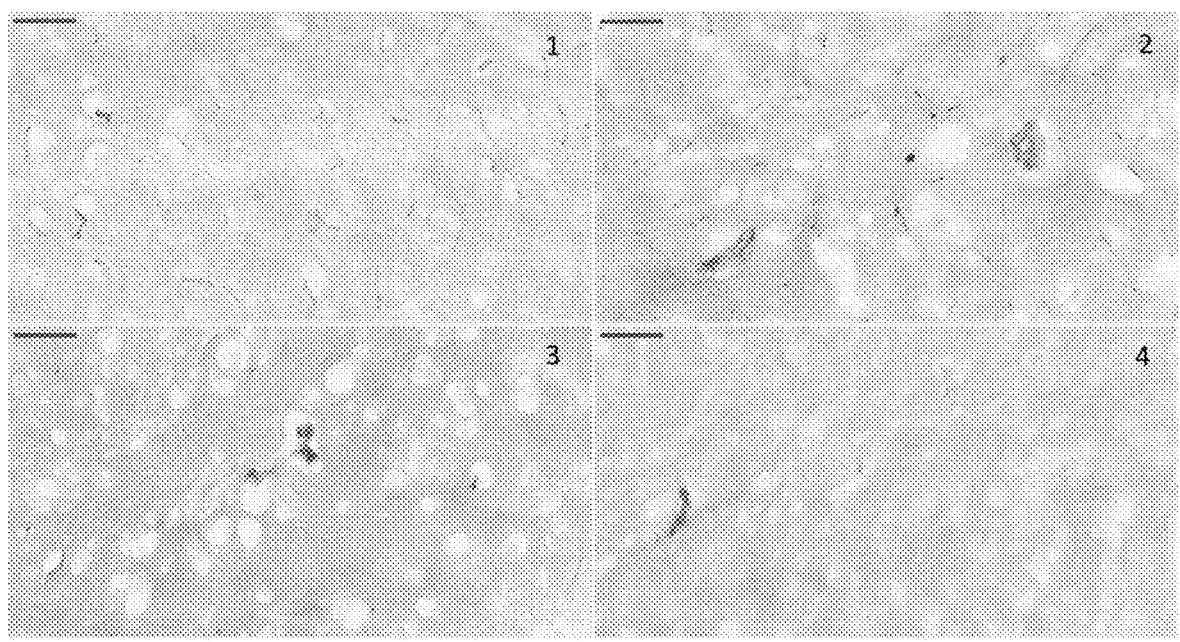

FIG. 56. Shows the immunostaining of the hippocampus from 10.5 month old rats with chromogranin A-specific antibody.

Figure 57:
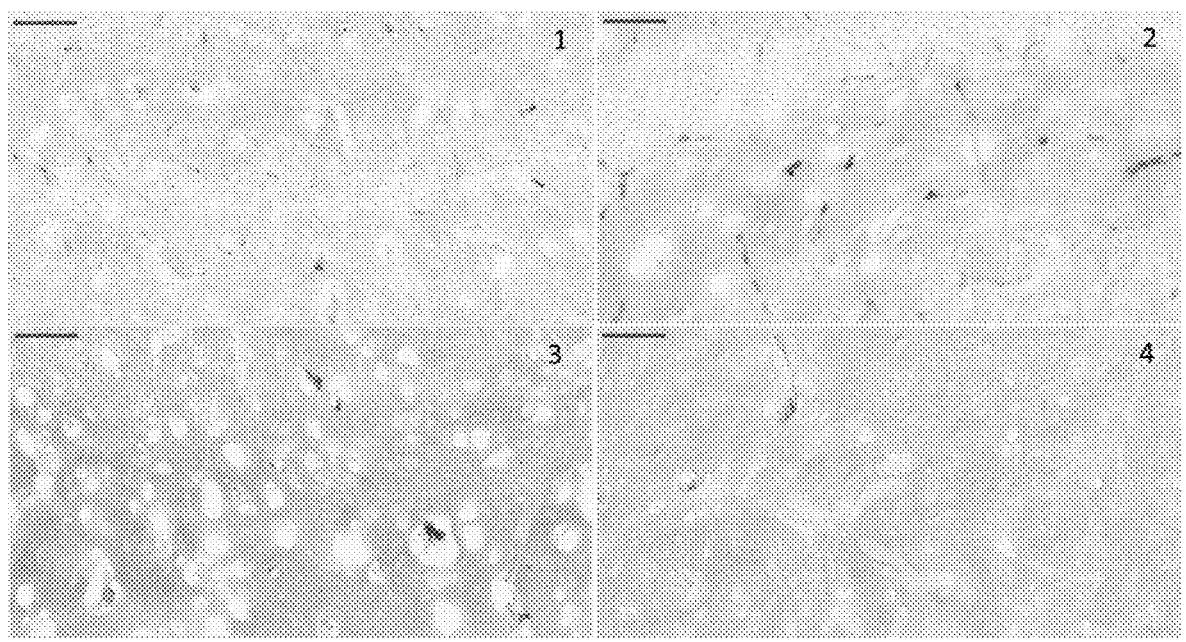

FIG. 57. Shows the immunostaining of hippocampus from 10.5 month old rats with chromogranin B-specific antibody.

Figure 58:
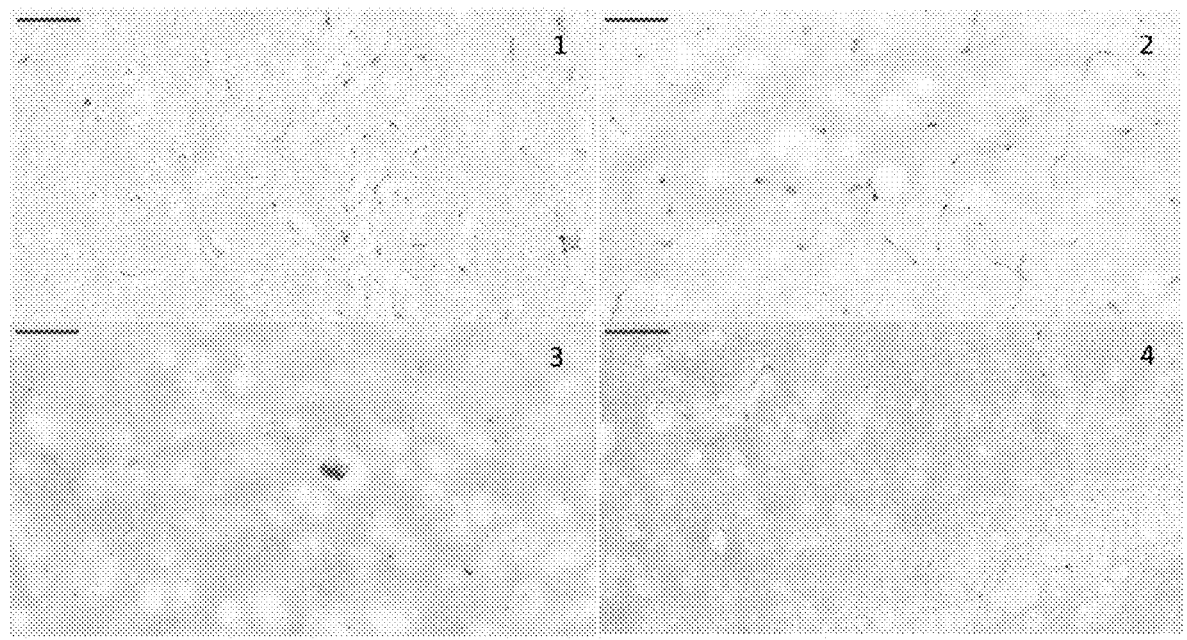

FIG. 58. Shows the immunostaining of hippocampus from 10.5 month old rats with secretogranin II-specific antibody.

Figure 59:
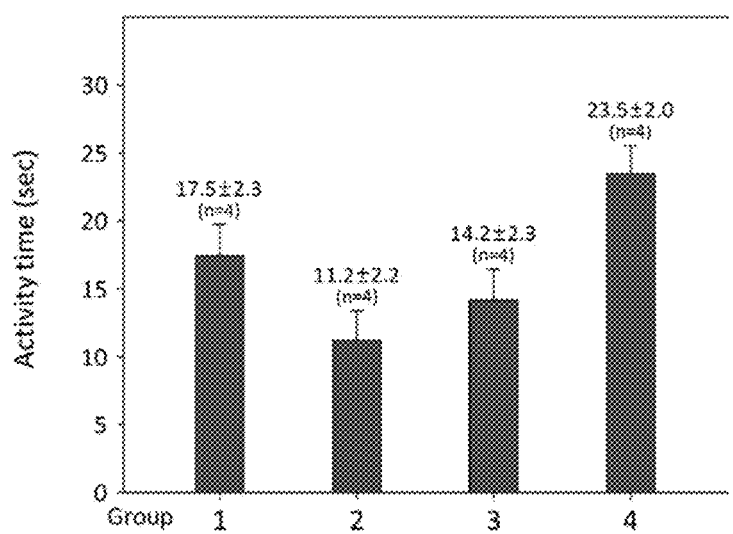

FIG. 59. Shows a comparison of mobile activity of the 11.5 month old rats with and without AD-like symptoms.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

DETAILED DESCRIPTION OF THE INVENTION

The brains of Alzheimer's disease (AD) patients are known to possess protein aggregates called senile plaques, and the clinical severity of Alzheimer's patients is directly tied to these plaques (Glass et al., 2010; Heneka et al., 2010, 2015). Given this, past efforts to find cures for AD have mainly focused on the study of these senile plaques; trying to find the components of senile plaques and devise ways of either inhibition of the formation of senile plaques or disruption and/or reduction of the already-formed plaques by interfering with aggregation of the protein components of the plaques (Glass et al., 2010; Heneka et al., 2010, 2015). The major components of senile plaques identified are beta-amyloid (Aβ) and granins (chromogranins and secretogranins) (Heneka et al., 2010, 2015, Willis et al., 2008, 2011). Beta-amyloids found in senile plaques consist of ~42 amino acids while the granin proteins consist mostly of ~430-700 amino acids (Bartolomucci et al., 2011; Helle, 2000; Taupenot et al., 2003).

Granins are secreted from the three major secretory cells of the brain, i.e., astrocytes, neurons and possibly from microglia as well, that constitute ~80% of brain cells, and are far more abundant in the brain and have orders of magnitude higher aggregation property than Aβ (Brinkmalm et al., 2018; Duits et al., 2018; Mattsson et al., 2013; Shaw et al., 2009; Wildsmith et al., 2014; Twig et al., 2005; Wu et al., 2013) and are at least ~5,400-fold more toxic on a molar basis and ~500-fold more toxic on a weight basis than Aβ to the brain cells (Twig et al., 2005; Wu et al., 2013).

The inventor has studied the contribution of granins, the major component proteins of senile plaques, in the formation of senile plaques, and the potential roles of granins in the pathogenic developments of brain cells. Our studies have shown that in this process that granins aggregate readily in the presence of metal ions such as Ca2+, Cu2+, Fe2+, and Zn2+, and in acidic pH, two features that are evident in the brains of AD patients (Faller et al., 2014; Wang and Xu, 2011; Ward et al., 2014; Yates et al., 1990; Zatta et al., 2009), and that the aggregated granins actively participate in the formation of senile plaques. The aggregation propensity of granins is orders of magnitude higher than that of beta-amyloid. Moreover, granin proteins were shown to be highly toxic to brain cells, and the toxicity was shown to be at least ~5,400-fold higher on a molar basis and ~500-fold higher on a weight basis than that of beta-amyloid (Twig et al., 2005; Wu et al., 2013).

One aspect of the invention is to study and provide ways to modulate, inhibit, or suppress the aggregation of a granin from a low molecular weight form to a high molecular weight aggregated form and/or to dissociate a high molecular weight aggregated form to a low molecular weight form. A particular aspect is to provide ways to modulate, inhibit, or suppress the aggregation of granins in the brain of an animal in order to modulate, inhibit, or suppress the pathogenesis of brain cells which leads to Alzheimer's disease and other neurodegenerative diseases. A granin typically includes one or more of the following chromogranin A (CGA), chromogranin B (CGB), secretogranin II (SgII) and secretogranin III (SgIII).

Accordingly, embodiments of the present invention disclose a composition for inhibiting the aggregation of a granin from a low molecular weight form to a high molecular weight aggregated form. Such a composition typically includes one or more active compounds or agents, which may also be referred to herein as disaggregation compounds. As used herein, an active agent or compound (used interchangeably herein) typically refers to a pharmaceutical agent that causes a biological effect when a sufficient amount is absorbed into the blood stream of an animal or patient. The embodiments may incorporate one or more disaggregation compounds for inhibiting the aggregation of a granin from a low molecular weight form to a high molecular weight aggregated form and/or dissociating a high molecular weight aggregated form to a low molecular weight form.

At least one, at least two, at least three, at least four, at least five, at least six, at least seven, at least eight, at least nine, or at least ten disaggregation compounds are utilized in various embodiments. However, more than ten disaggregation compounds may be utilized in alternative embodiments. In one aspect, a disaggregation compound provided herein inhibits the aggregation of a granin from a low molecular weight form to a high molecular weight aggregated form and/or dissociates a high molecular weight aggregated form to a low molecular weight form. In another aspect, a disaggregation compound provided herein inhibits, prevents, or modulates the interaction or binding of a granin with a metal ion or cofactor including, for example, $Zn^{2+}$, $Cu^{2+}$, $Fe^{2+}$ and $Ca^{2+}$. In certain embodiments, one or more disaggregation compound is provided that reduces, inhibits, suppress, or sequesters a metal ion selected from $Zn^{2+}$, $Cu^{2+}$, $Fe^{2+}$ and $Ca^{2+}$ to inhibit, prevent, or modulate the interaction or binding of a granin with the metal ion in the nervous system of an animal, thereby inhibiting the aggregation of a granin from a low molecular weight form to a high molecular weight aggregated form and/or dissociating a high molecular weight aggregated form to a low molecular weight form in the animal.

Suitable disaggregation compounds include, without limitation, the following: anthoxanthins, anthocyanins and anthocyanidins, flavans, flavanones, flavononols, stilbenoids, metalloproteins, $Zn^{2+}$ binding and sequestering molecules, casein, albumin, zinc finger transcription factors, metal ion chelators, $Cu^{2+}$ binding and sequestering molecules, ceruloplasmin, casein, albumin, $Fe^{2+}$ binding and sequestering molecules, calmodulin, troponin, ferritin, transferrin, lactoferrin, cordycepin, tyrphostin AG1478, and 5,7-dimethoxyflavone.

Suitable anthoxanthins include, without limitation, the following: scutellarein, luteolin, baicalein, kaempferol, quercetin, apigenin, tangeretin, myricetin, fisetin, morin, galangin, isorhamnetin, pachypodol, rhamnazin, pyranoflavonols, and furanoflavonols.

Suitable stilbenoids include, without limitation, the following: resveratrol, piceatannolin, pinosylvin, pterostilbene, astringin, and piceid. A preferred herein stilbenoid is resveratrol.

Suitable flavans include, without limitation, the following: epigallocatechin 3-gallate (EGCG), catechin, gallocatechin, catechin 3-gallate, gallocatechin 3-gallate, epicatechin, epigallocatechin, epicatechin 3-gallate, theaflavin-3-gallate, theaflavin-3'-gallate, theaflavin-3,3'-gallate, thearubigin, and proanthocyanidins. A preferred herein flavan is epigallocatechin 3-gallate (EGCG).

Methods

In another aspect, methods of i) modulating, inhibiting or preventing the interaction of granins with metal ions, ii) modulating, inhibiting, preventing the aggregation of granins, or dissociating a high molecular weight aggregated form to a low molecular weight form, iii) reducing or inhibiting cell toxicity, and iv) treating or preventing dementia or Alzheimer's disease are provided.

In one aspect, these methods typically use one or more disaggregation compounds. A preferred disaggregation compound comprises an anthoxanthin. Thus certain embodiments provided herein are directed to methods of using the composition for inhibiting the interaction of granins with metal ions, wherein the composition comprises one or more anthoxanthins.

As a non-limiting example, one particular embodiment provided herein is directed to methods of using the composition for inhibiting the interaction of granins with metal ions, the composition comprising at least two of the following: scutellarein, luteolin, baicalein, kaempferol, quercetin, apigenin, tangeretin, myricetin, fisetin, morin, resveratrol, EGCG, cordycepin, 5,7-dimethoxyflavone, and tyrphostin AG1478. Other embodiments use compositions for inhibiting the interaction of granins with metal ions comprising at least two, at least three, at least four, at least five, at least six, at least seven, at least eight, or all of the following: scutellarein, luteolin, baicalein, kaempferol, quercetin, apigenin, tangeretin, myricetin, fisetin, morin, resveratrol, EGCG, cordycepin, 5,7-dimethoxyflavone, and tyrphostin AG1478. One embodiment comprises the following: scutellarein, luteolin, baicalein, kaempferol, apigenin, tangeretin, myricetin, fisetin, morin, resveratrol, and EGCG. Another embodiment comprises the following: scutellarein, luteolin, baicalein, kaempferol, quercetin, resveratrol, EGCG, cordycepin, 5,7-dimethoxyflavone, and tyrphostin AG1478.

A particular embodiment provided herein is directed to a composition and methods for inhibiting the interaction of granins with metal ions, the composition comprising i) an anthoxanthin, ii) a stilbenoid, and iii) a disaggregation compound other than an anthoxanthin or stilbenoid. In certain further embodiments, the anthoxanthin is one or more of the following scutellarein, luteolin, baicalein, kaempferol, quercetin, apigenin, tangeretin, myricetin, fisetin. In certain further embodiments, the stilbenoid is resveratrol or a derivative, salt, or ester thereof. In certain further embodiments, the disaggregation compound other than an anthoxanthin or stilbenoid is selected from EGCG, cordycepin, 5,7-dimethoxyflavone, tyrphostin AG1478.

In another aspect, methods of modulating, inhibiting, or preventing the aggregation of a granin from a low molecular weight form to a high molecular weight aggregated form or dissociating a high molecular weight aggregated form to a low molecular weight form are provided. Accordingly, in certain embodiments pharmaceutical compositions are disclosed and provided for modulating, inhibiting, or preventing the aggregation of a granin from a low molecular weight form to a high molecular weight aggregated form. In certain embodiments, these methods use compositions for inhibiting the aggregation of a granin from a low molecular weight form to a high molecular weight aggregated form. One particular embodiment of pharmaceutical composition for methods of modulating, inhibiting, or preventing the aggregation of a granin from a low molecular weight form to a high molecular weight aggregated form provided includes at least two of the following: scutellarein, luteolin, baicalein, kaempferol, quercetin, apigenin, tangeretin, myricetin, fisetin, resveratrol, EGCG, cordycepin, and tyrphostin AG1478. Alternative embodiments include at least three, at least four, at least five, at least six, at least seven, at least eight, at least nine, or at least ten disaggregation compounds in a pharmaceutical composition or formulation.

In another aspect a method for the treatment or prevention of dementia or Alzheimer's disease is provided. Accordingly, in certain embodiments pharmaceutical compositions are disclosed and provided for methods of treatment or prevention of dementia or Alzheimer's disease. In certain embodiments, these methods use compositions for inhibiting the aggregation of a granin from a low molecular weight form to a high molecular weight aggregated form and/or dissociating a high molecular weight aggregated form to a low molecular weight form. One particular embodiment of pharmaceutical composition for the treatment or prevention of dementia or Alzheimers disease provided includes at least two of the following: scutellarein, luteolin, baicalein, kaempferol, quercetin, apigenin, tangeretin, myricetin, fisetin, resveratrol, EGCG, cordycepin, and tyrphostin AG1478. Alternative embodiments include at least three, at least four, at least five, at least six, at least seven, at least eight, at least nine, or at least ten disaggregation compounds in a pharmaceutical composition or formulation.

In another aspect, a method of reducing or inhibiting cell toxicity is provided. In preferred embodiments, the method comprises administering a composition for inhibiting the aggregation of a granin from a low molecular weight form to a high molecular weight aggregated form and/or dissociating a high molecular weight aggregated form to a low molecular weight form provided herein.

In another aspect, methods for the treatment or prevention of dementia or Alzheimer's disease are provided. In certain embodiments, the method comprises administering an effective amount of a pharmaceutical composition for inhibiting the aggregation of a granin from a low molecular weight form to a high molecular weight aggregated form and/or dissociating a high molecular weight aggregated form to a low molecular weight form to an animal (e.g. a patient). In one particular embodiment, the composition comprises at least two of the following: scutellarein, luteolin, baicalein, kaempferol, quercetin, apigenin, tangeretin, myricetin, fisetin, resveratrol, EGCG, cordycepin, and tyrphostin AG1478. In preferred embodiments, the method is effective to inhibit the aggregation of a granin from a low molecular weight form to a high molecular weight aggregated form and/or to dissociate a high molecular weight aggregated form to a low molecular weight form in an animal.

Compositions and Formulations

The daily dose of an active compound may be, e.g., at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 150 mg, at least 200 mg, at least 250 mg, at least 300 mg, at least 350 mg, at least 400 mg, at least 450 mg, at least 500 mg, at least 550 mg, at least 600 mg, at least 650 mg, at least 700 mg, at least 750 mg, at least 800 mg, at least 850 mg, at least 900 mg, at least 950 mg, at least 1000 mg, at least 1050 mg, at least 1100 mg, at least 1150 mg, at least 1200 mg, at least 1250 mg, at least 1300 mg, at least 1350 mg, at least 1400 mg, at least 1450 mg, at least 1500 mg, at least 2000 mg, at least 3000 mg, at least 5000 mg or more mg.

Aspects of the present specification disclose a dose of a therapeutic compound to treat a disorder is in the range of at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day or in the range of about 0.001 mg/kg/day to about 100 mg/kg/day or in the range of about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day.

In another aspect, the ratio of one or more disaggregation compounds to another disaggregation compound in a composition for inhibiting the aggregation of a granin from a low molecular weight form to a high molecular weight aggregated form and/or dissociating a high molecular weight aggregated form to a low molecular weight form may vary in different embodiments. In this aspect, the ratio of the total amount of one disaggregation compound to the total amount of another disaggregation compound may range, for example, from about 1:100, 1:95, 1:90, 1:85, 1:80, 1:75, 1:70, 1:65, 1:60, 1:55, 1:50, 1:45, 1:40, 1:35, 1:30, 1:25, 1:20, 1:15, 1:10, 1:9, 1:8, 1:7, 1:6, 1:5, 1:4, 1:3, 1:2, or 1:1 w/w to about 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 9:1, 8:1, 7:1, 6:1, 5:1, 4:1, 3:1, 2.5:1, 2:1, 1.9:1, 1.8:1, 1.7:1. 1.6:1, 1:5:1, 1.4:1, 1.3:1, 1.2:1, 1.1:1, and 1:1 w/w.

Aspects of the present specification disclose that a decrease or reduction in granin aggregation is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% and the severity associated with Alzheimer's Disease symptoms (AD) is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.

In other aspects of this embodiment, administration of a therapeutic compound of the present invention as disclosed herein reduces the severity of symptoms associated with a disease associated with granin aggregation by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

Aspects of the present specification disclose the symptoms associated with decrease or reduction in granin aggregation is reduced by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%. In preferred embodiments, the symptoms described above associated with a decrease or reduction in granin aggregation further applies to the methods of i) modulating, inhibiting or preventing the interaction of granins with metal ions, ii) modulating, inhibiting, preventing the aggregation of granins, or dissociating a high molecular weight aggregated form to a low molecular weight form, iii) reducing or inhibiting cell toxicity, and iv) treating or preventing dementia or Alzheimer's disease described herein.

Dosing can be single dosage or cumulative (serial dosing), and can be readily determined by one skilled in the art. A therapeutic compound of the present invention may be administered once, twice, three, four, five, six, seven, eight, nine, ten, eleven, twelve, thirteen, fourteen, fifteen, sixteen, seventeen, eighteen, nineteen, twenty or more times to a subject. For instance, treatment of AD may comprise a one-time administration of an effective dose of a therapeutic compound as disclosed herein. Alternatively, treatment of AD may comprise multiple administrations of an effective dose of a therapeutic compound as carried out over a range of time periods, such as, e.g., once daily, twice daily, trice daily, once every few days, or once weekly. The timing of administration can vary from individual to individual, depending upon such factors as the severity of an individual's symptoms. For example, an effective dose of a therapeutic compound as disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly. In one embodiment, a therapeutic compound as disclosed herein is capable of decreasing the time to resolve the symptoms of a disease, including in an individual suffering from AD by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% as compared to a patient not receiving the same treatment.

In an embodiment, the period of administration of a therapeutic compound is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

A therapeutic compound as disclosed herein is administered to an individual. An individual is typically a human being, but can be an animal, including, but not limited to, dogs, cats, birds, cattle, horses, sheep, goats, reptiles and other animals, whether domesticated or not.

In another aspect, provided herein is a kit or package containing, without limitation, at least one combination composition of the invention, accompanied by instructions for use. In an embodiment, in instances in which each therapeutic compound themselves are administered, without limitation, as individual or separate dosage forms (e.g., capsules, tablets or liquid), the kit comprises, without limitation, each therapeutic compound making up the composition of the invention, along with instructions for use. In an additional embodiment, a therapeutic compound, without limitation, may be packaged in any manner suitable for administration, so long as the packaging, when considered along with the instructions for administration, without limitation, clearly indicates the manner in which each therapeutic compound is to be administered. In a further embodiment, each therapeutic compound or a combination of therapeutic compounds may, without limitation, be combined into a single administrable dosage form such as a liquid, including a liquid administered subcutaneously or other liquid formulation. A therapeutic compound can be provided to an individual in a package. The package can be a container, for instance, without limitation, a bottle, a canister, a tube or other enclosed vessel.

In an embodiment, in instances in which each of the drugs themselves are administered, without limitation, as individual or separate dosage forms (e.g., capsules or tablets), the kit comprises, without limitation, each of the drugs making up the composition of the invention, along with instructions for use. In an additional embodiment, the drug components, without limitation, may be packaged in any manner suitable for administration, so long as the packaging, when considered along with the instructions for administration, without limitation, clearly indicates the manner in which each of the drug components is to be administered. In a further embodiment, each of the drug components of the combination may, without limitation, be combined into a single administrable dosage form such as a capsule.

EXAMPLES

The following non-limiting examples are provided for illustrative purposes only in order to facilitate a more complete understanding of representative embodiments now contemplated. These examples are intended to be a mere illustration only and not to constitute a limitation on the scope of the invention.

Thus, these examples should not be construed to limit any of the embodiments described in the present specification.

Example 1

Aggregation of Granins Upon Metal Ion Binding

Experiments were performed to test the effect of metals, in particular $Cu^{2+}$, $Zn^{2+}$, and $Fe^{2+}$, on the aggregation of granins.

Materials and Methods

Figure 4:
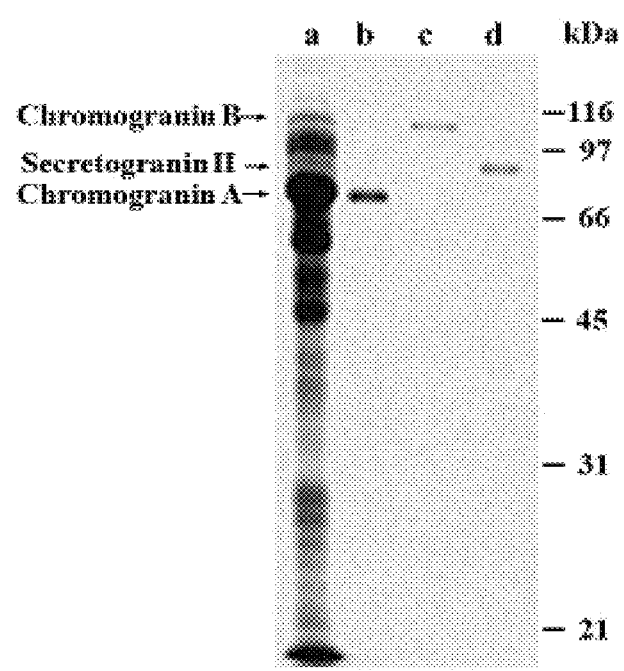
FIG. 4. Shows purified native chromogranin B (c), secretogranin II (d), and chromogranin A (b).

Materials: The major granin proteins, chromogranin A (CGA), chromogranin B (CGB), and secretogranin II (SgII) were purified from secretory granules of bovine adrenal medulla as described (Park et al., 2002; Yoo, 1995; Yoo and Albanesi, 1990). Chelex 100 was from Bio-Rad (U.S.A), and other chemicals were of highest purity that is commercially available. Purified native chromogranin B (c), secretogranin II (d), and chromogranin A (b) are illustrated in FIG. 4. The flavonoids, stilbenoids, and the other test compounds used in the present experiments were obtained from MedChem Express (U.S.A.), Sigma-Aldrich (U.S.A.), and Santa-Cruz Biotech. (U.S.A.), and the purity of all the compounds tested was 98% or higher.

Aggregation Experiments: Prior to aggregation studies, it is necessary to remove metal ions that had interacted with granins during purification process from granins through extensive treatments with chelating agents such as Chelex 100 (Bio-Rad, U.S.A) to dissociate the granin aggregates. For metal-induced aggregation studies, Chelex 100-treated CGA, CGB, or SgII in 2 mM MOPS, pH 7.4, was titrated with concentrated metal ions such as $CuCl_2$, $FeCl_2$, and $ZnCl_2$. Aggregation was monitored by measuring the turbidity change with a Beckman DU640 uv/vis spectrophotometer. All the measurements were done at 24° C.

Figure 5:
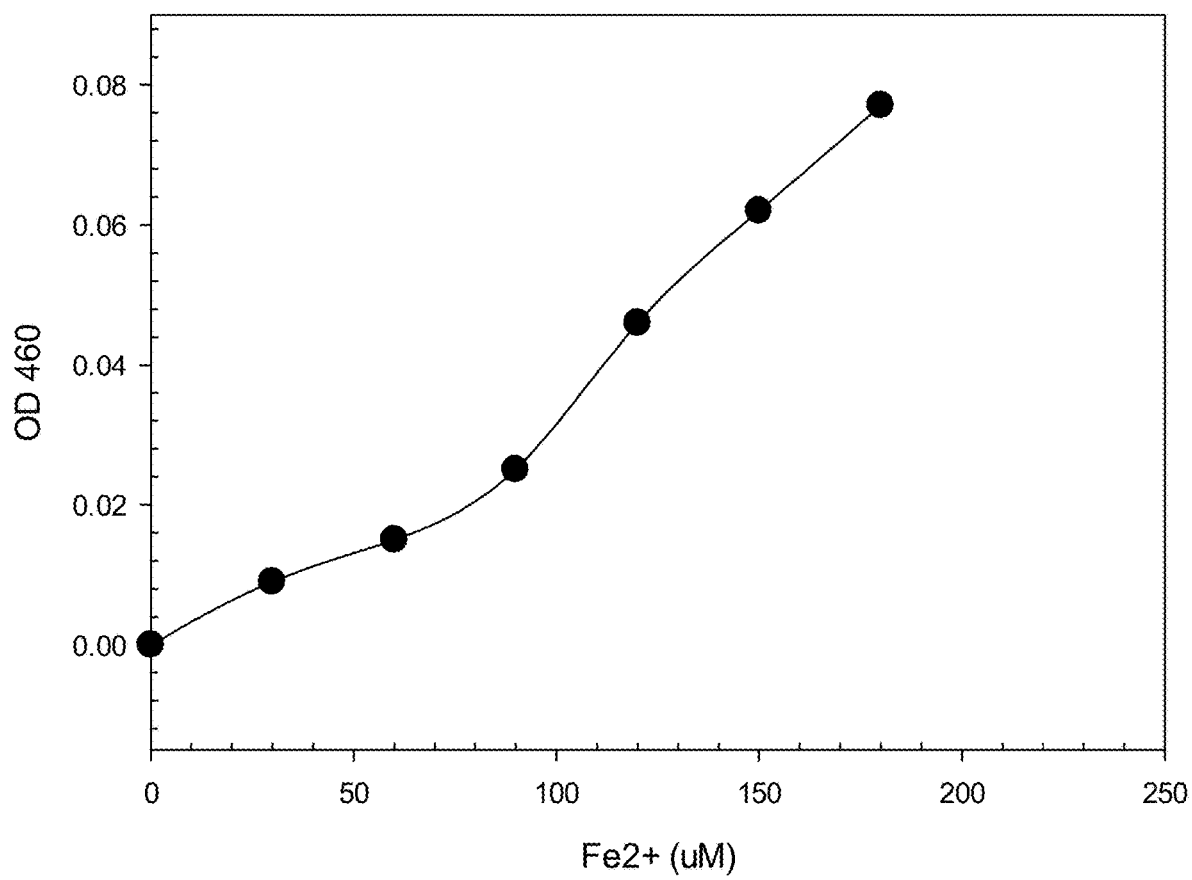
FIG. 5. Shows aggregation of chromogranin A as a function of increasing $Fe^{2+}$ concentrations.
Figure 6:
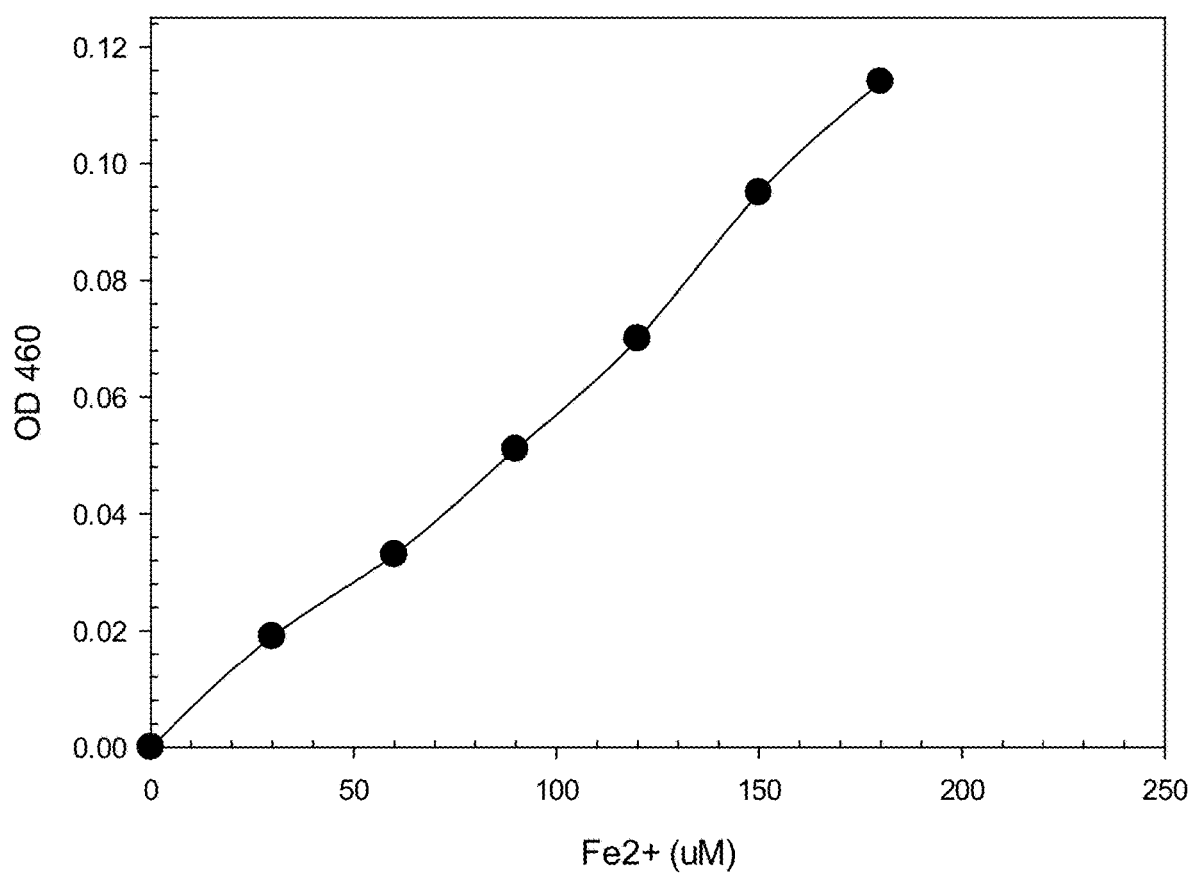
FIG. 6. Shows aggregation of chromogranin B as a function of increasing $Fe^{2+}$ concentrations.
Figure 7:
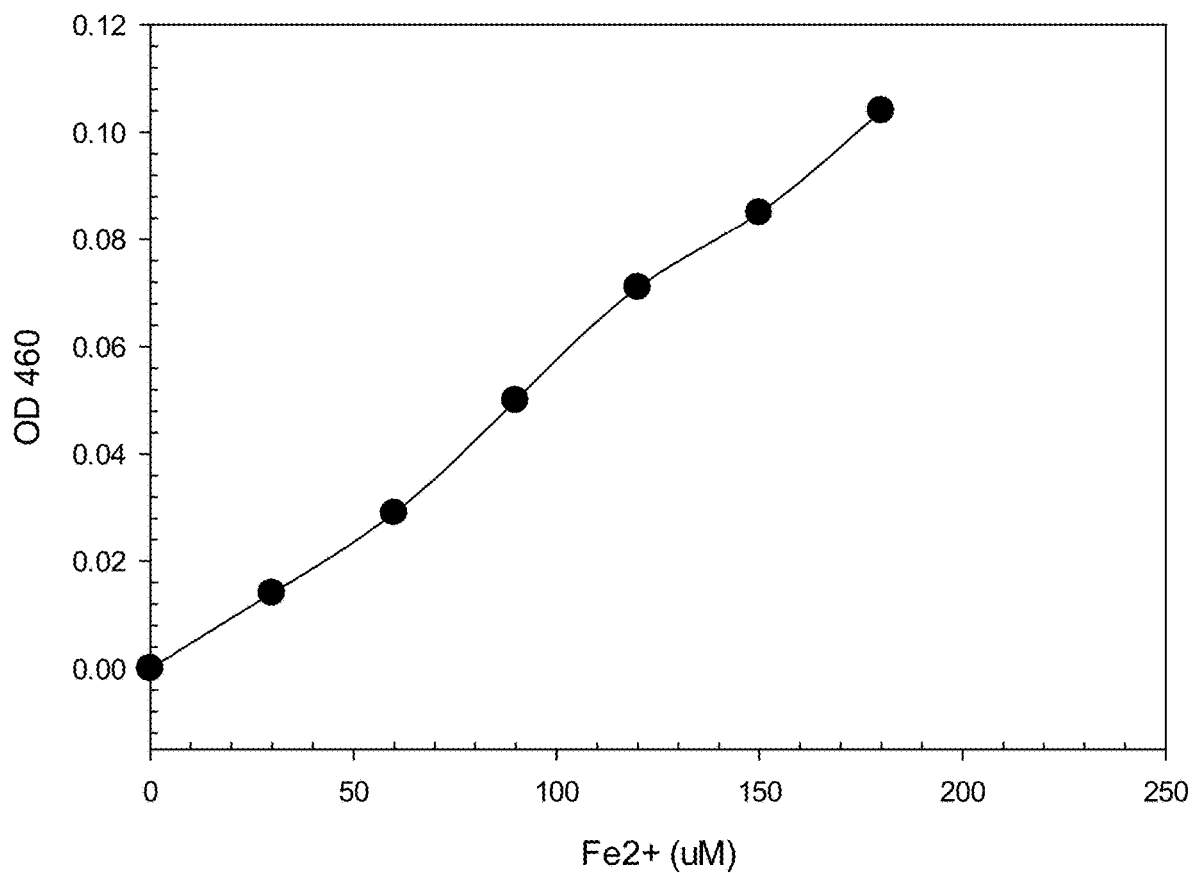
FIG. 7. Shows aggregation of secretogranin II as a function of increasing $Fe^{2+}$ concentrations.

FIGS. 5-10 show the effects of particular metals on the aggregation characteristics of particular granins. FIG. 5. shows aggregation of chromogranin A as a function of increasing $Fe^{2+}$ concentrations. 0.005 mg/ml chromogranin A (0.1 μM) was used as a function of $Fe^{2+}$ concentrations at pH 7.4. From FIG. 5, it is evident that the higher the $Fe^{2+}$ concentrations the higher the magnitude of $Fe^{2+}$-induced aggregation of chromogranin A. FIG. 6. shows aggregation of chromogranin B as a function of increasing $Fe^{2+}$ concentrations. 0.005 mg/ml chromogranin B (0.06 μM) was used as a function of $Fe^{2+}$ concentrations at pH 7.4. From FIG. 6, it is evident that the higher the Fe2+ concentrations the higher the magnitude of $Fe^{2+}$-induced aggregation of chromogranin B. FIG. 7 shows aggregation of secretogranin II as a function of increasing $Fe^{2+}$ concentrations. An amount of 0.005 mg/ml secretogranin II (0.07 μM) was used as a function of $Fe^{2+}$ concentrations at pH 7.4. From FIG. 7, it is evident that the higher the $Fe^{2+}$ concentrations the higher the magnitude of $Fe^{2+}$-induced aggregation of secretogranin II.

Figure 8:
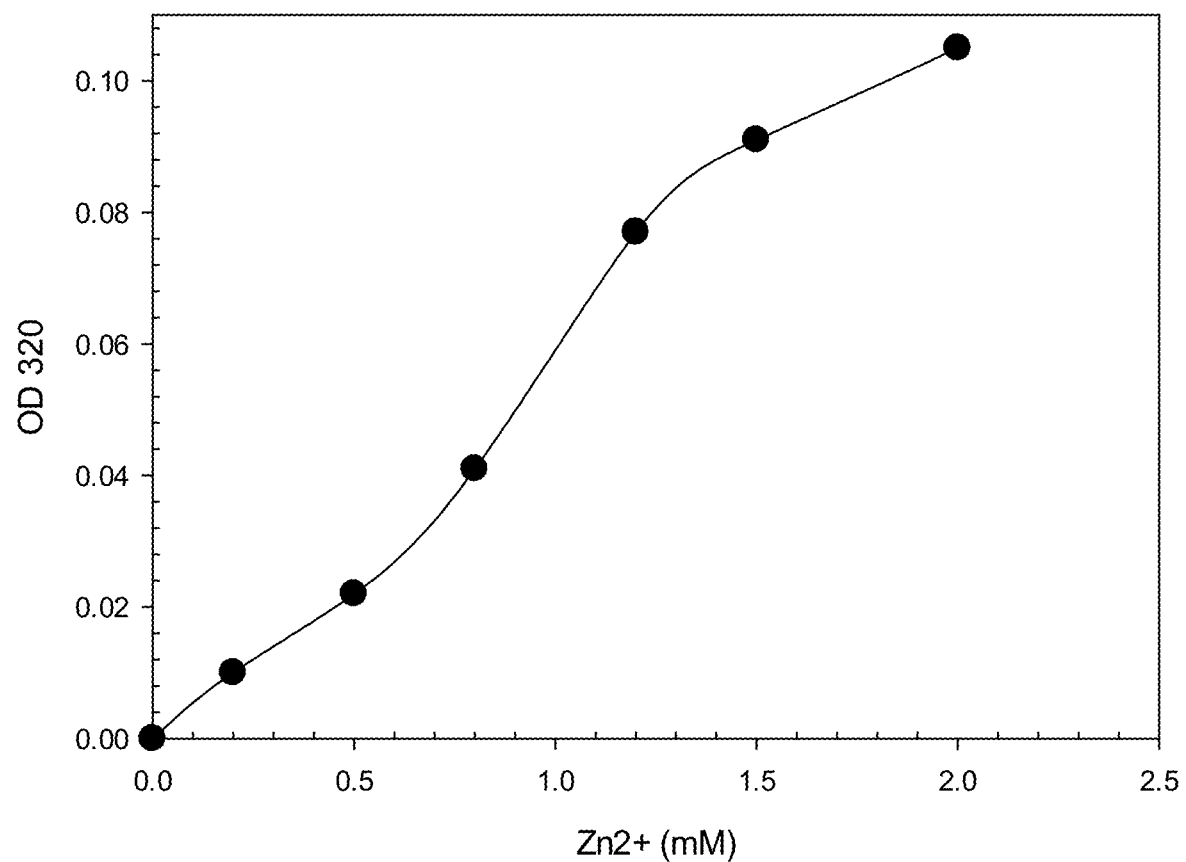
FIG. 8. Shows aggregation of chromogranin B as a function of increasing $Zn^{2+}$ concentrations.
Figure 9:
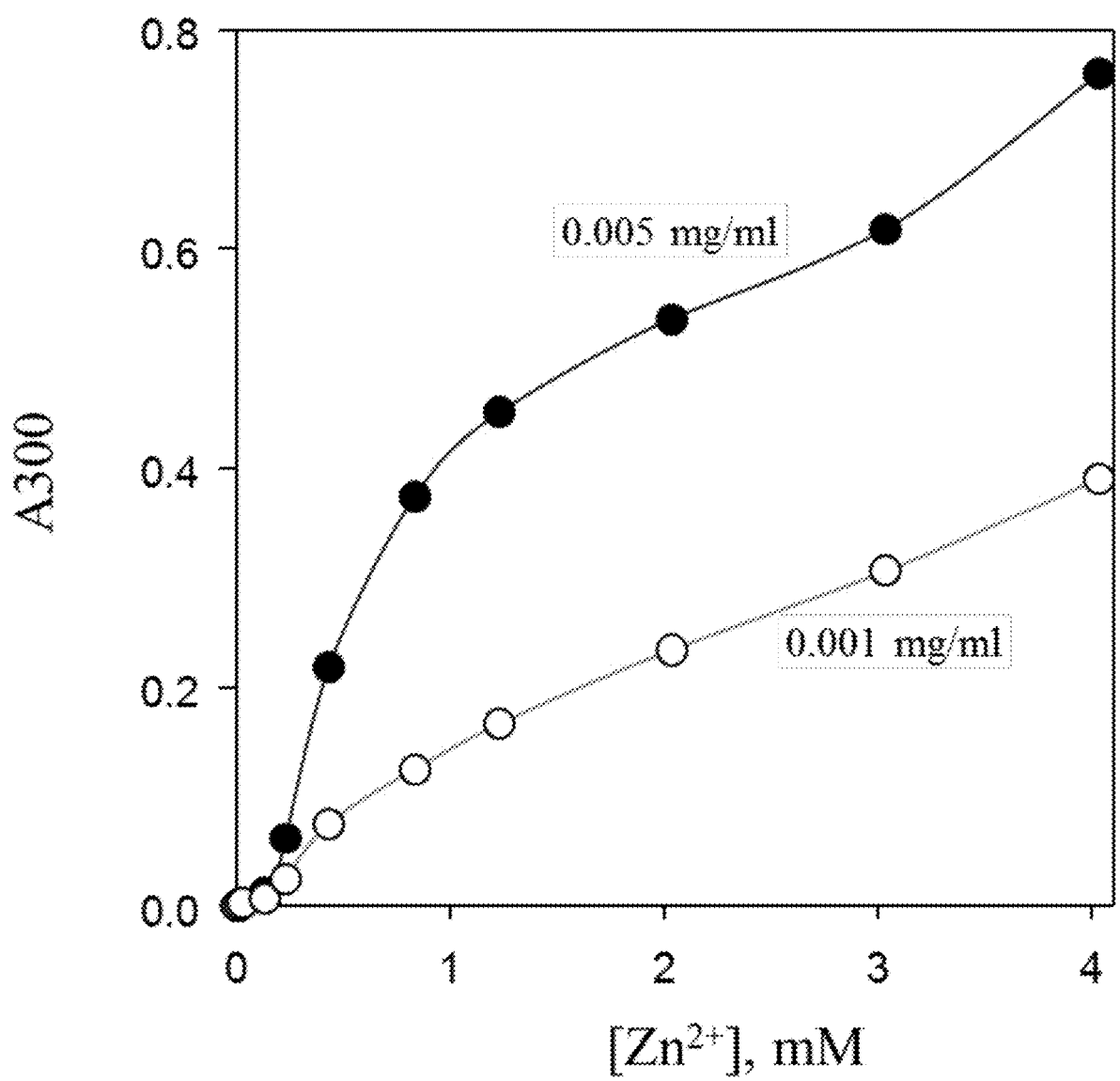
FIG. 9. Shows aggregation of secretogranin II as a function of increasing $Zn^{2+}$ concentrations.
Figure 10:
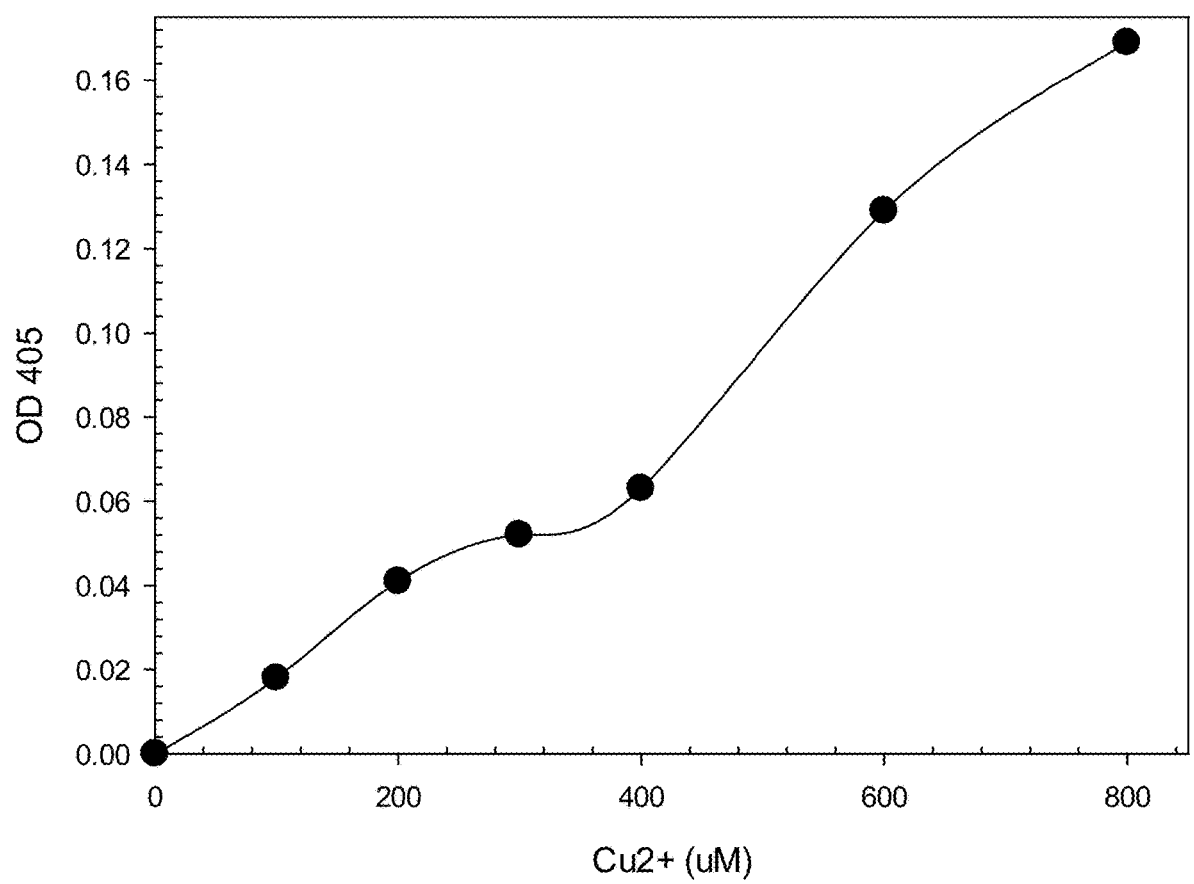
FIG. 10. Shows aggregation of secretogranin II as a function of increasing $Cu^{2+}$ concentrations.
Figure 11:
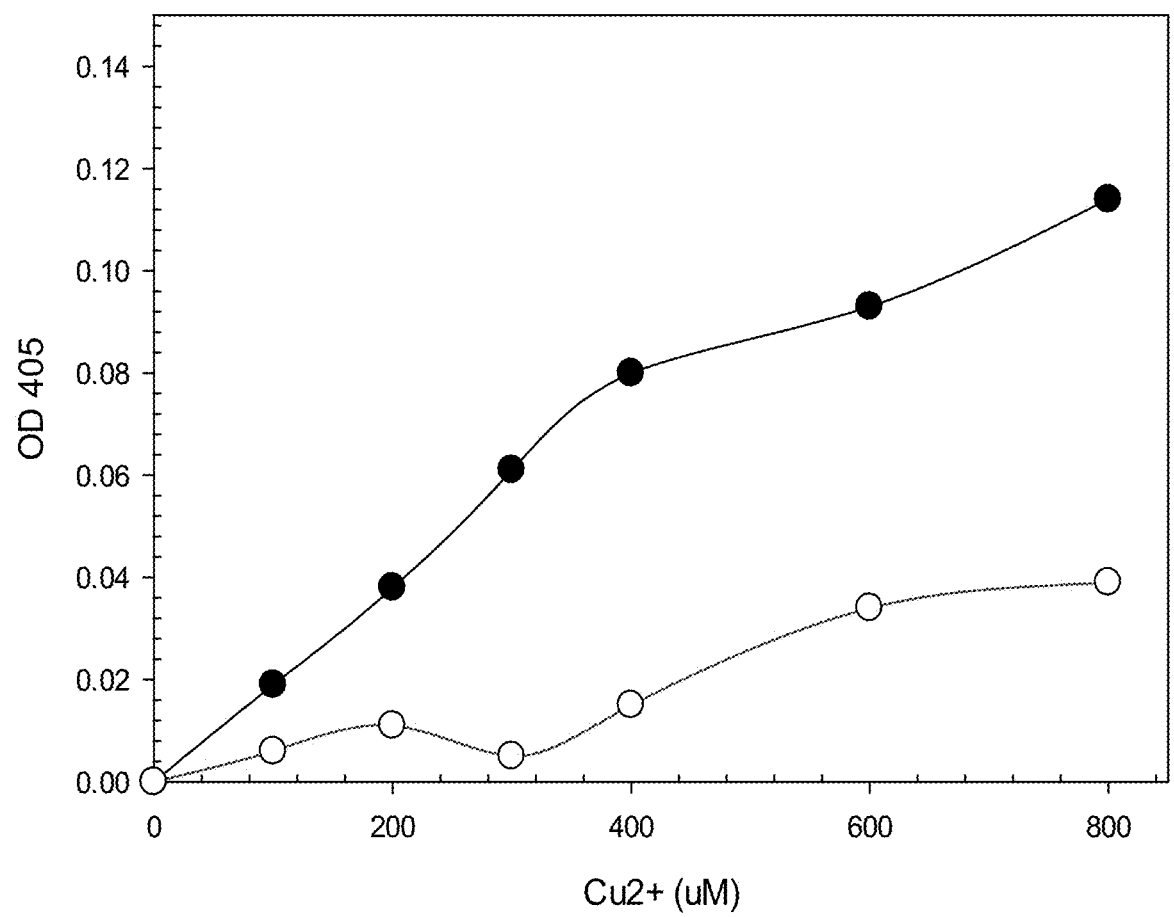
FIG. 11. Shows prevention of Cu2+-induced chromogranin A aggregation by scutellarein. Cu2+-induced chromogranin A aggregation (0.005 mg/ml) (0.1 µM) was mostly suppressed by 1 µM scutellarein at pH 7.4. Chromogranin A aggregation by increasing concentrations of Cu2+ is expressed in black line (closed circles) while that in the presence of scutellarein is expressed in grey line (open circles).
Figure 12:
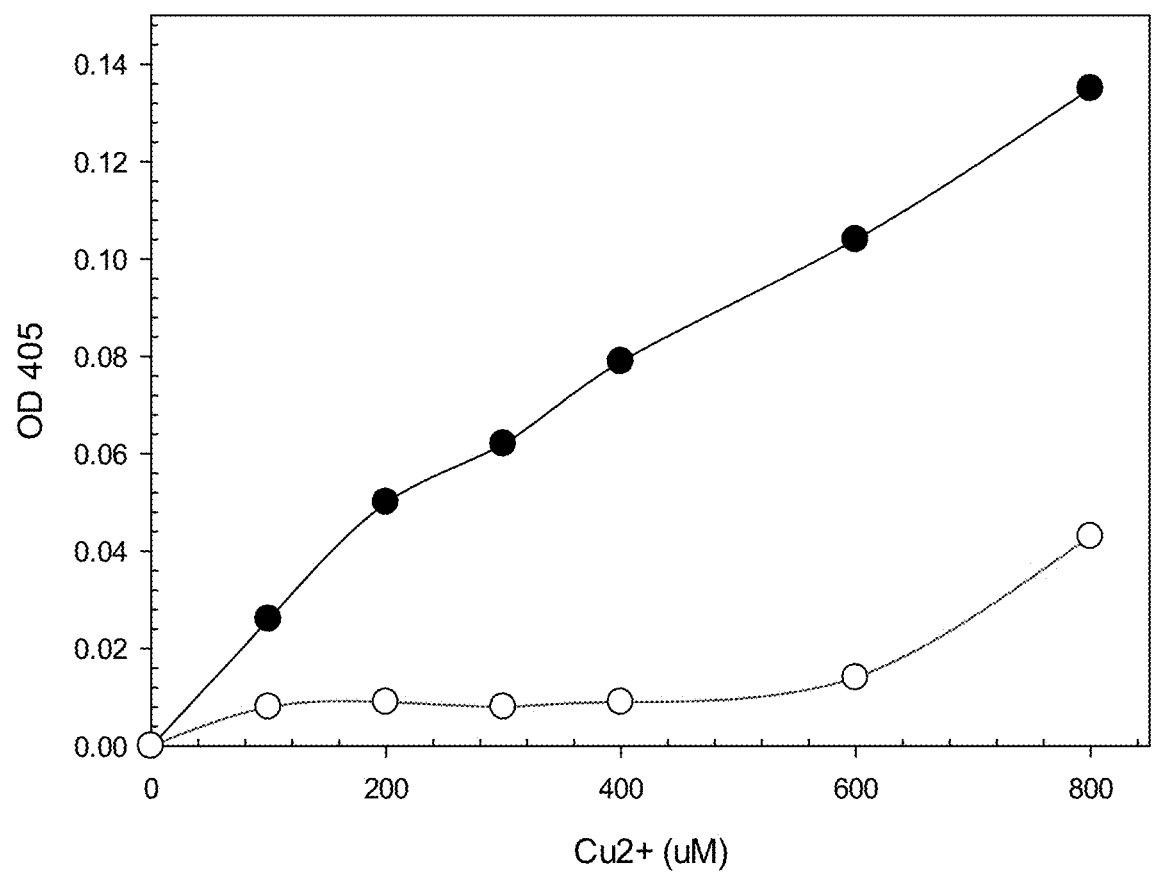
FIG. 12. Shows prevention of Cu2+-induced secretogranin II aggregation by scutellarein. Cu2+-induced secretogranin II aggregation (0.005 mg/ml) (0.07 µM) was mostly inhibited by 1 µM scutellarein at pH 7.4. Secretogranin II aggregation by increasing concentrations of Cu2+ is expressed in black line (closed circles) while that in the presence of scutellarein is expressed in grey line (open circles).
Figure 13:
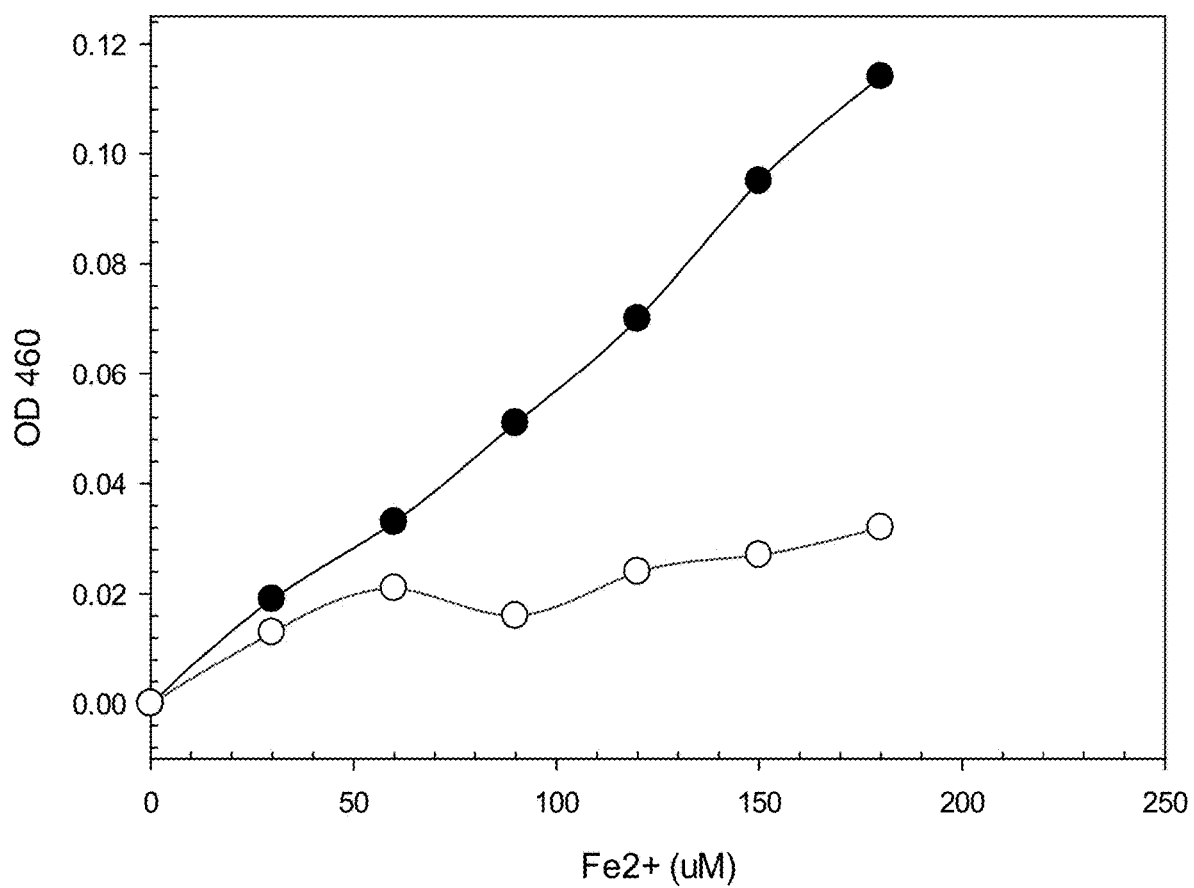
FIG. 13. Shows prevention of Fe2+-induced chromogranin B aggregation by luteolin. Fe2+-induced chromogranin B aggregation (0.005 mg/ml) (0.06 µM) was mostly inhibited by 1 µM luteolin at pH 7.4. Chromogranin B aggregation by increasing concentrations of Fe2+ is expressed in black line (closed circles) while that in the presence of luteolin is expressed in grey line (open circles).

FIG. 8 shows aggregation of chromogranin B as a function of increasing $Zn^{2+}$ concentrations. 0.005 mg/ml chromogranin B (0.06 µM) was used as a function of $Zn^{2+}$ concentrations at physiological pH 7.4. From FIG. 8, it is evident that the higher the $Zn^{2+}$ concentrations the higher the magnitude of $Zn^{2+}$-induced aggregation of chromogranin B. FIG. 9 shows aggregation of secretogranin II as a function of increasing $Zn^{2+}$ concentrations. Increasing secretogranin II concentrations were used as a function of $Zn^{2+}$ concentrations at physiological pH 7.4. From FIG. 9, it is evident that the higher the secretogranin II concentrations the higher the magnitude of $Zn^{2+}$-induced aggregation of secretogranin II. FIG. 10. shows aggregation of secretogranin II as a function of increasing $Cu^{2+}$ concentrations. An amount of 0.005 mg/ml secretogranin II (0.07 µM) was used as a function of $Cu^{2+}$ concentrations at pH 7.4. From FIG. 10, it is evident that the higher the $Cu^{2+}$ concentrations the higher the magnitude of $Cu^{2+}$-induced aggregation of secretogranin II. FIG. 11. Shows prevention of Cu2+-induced chromogranin A aggregation by scutellarein. Cu2+-induced chromogranin A aggregation (0.005 mg/ml) (0.1 µM) was mostly suppressed by 1 µM scutellarein at pH 7.4. Chromogranin A aggregation by increasing concentrations of Cu2+ is expressed in black line (closed circles) while that in the presence of scutellarein is expressed in grey line (open circles). From FIG. 11, it is evident that scutellarein mostly inhibited the $Cu^{2+}$-induced chromogranin A aggregation. FIG. 12 shows prevention of $Cu^{2+}$-induced secretogranin II aggregation by scutellarein. Cu2+-induced secretogranin II aggregation (0.005 mg/ml) (0.07 µM) was mostly inhibited by 1 µM scutellarein at pH 7.4. Secretogranin II aggregation by increasing concentrations of Cu2+ is expressed in black line (closed circles) while that in the presence of scutellarein is expressed in grey line (open circles). From FIG. 12, it is evident that scutellarein mostly inhibited the $Cu^{2+}$-induced secretogranin II aggregation. FIG. 13 shows prevention of $Fe^{2+}$-induced chromogranin B aggregation by luteolin. $Fe^{2+}$-induced chromogranin B aggregation (0.005 mg/ml) (0.06 µM) was mostly inhibited by 1 µM luteolin at pH 7.4. Chromogranin B aggregation by increasing concentrations of $Fe^{2+}$ is expressed in black line (closed circles) while that in the presence of luteolin is expressed in grey line (open circles). From FIG. 13, it is evident that luteolin mostly inhibited the $Fe^{2+}$-induced chromogranin B aggregation.

Figure 14:
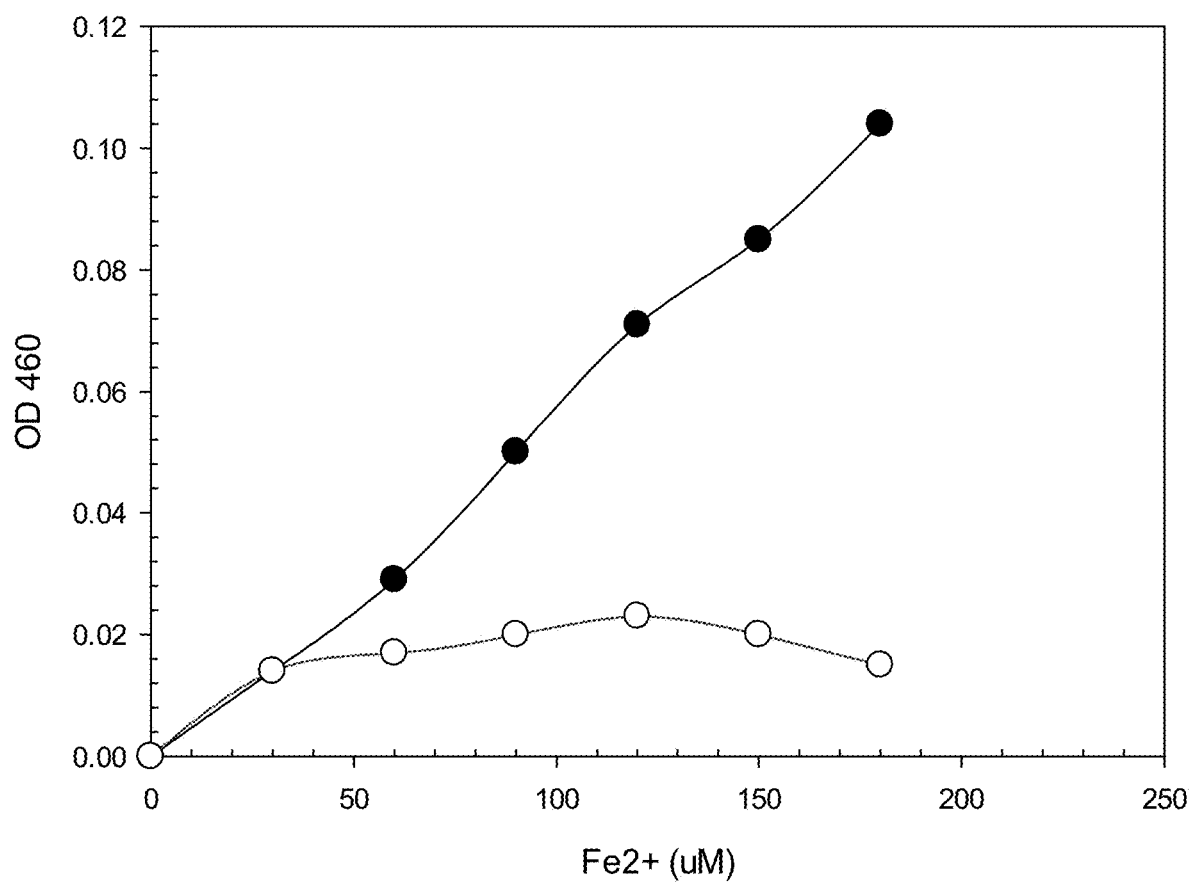
FIG. 14. Shows prevention of Fe2+-induced secretogranin II aggregation by luteolin. Fe2+-induced secretogranin II aggregation (0.005 mg/ml) (0.07 µM) was mostly inhibited by 1 µM luteolin at pH 7.4. Secretogranin II aggregation by increasing concentrations of Fe2+ is expressed in black line (closed circles) while that in the presence of luteolin is expressed in grey line (open circles).
Figure 15:
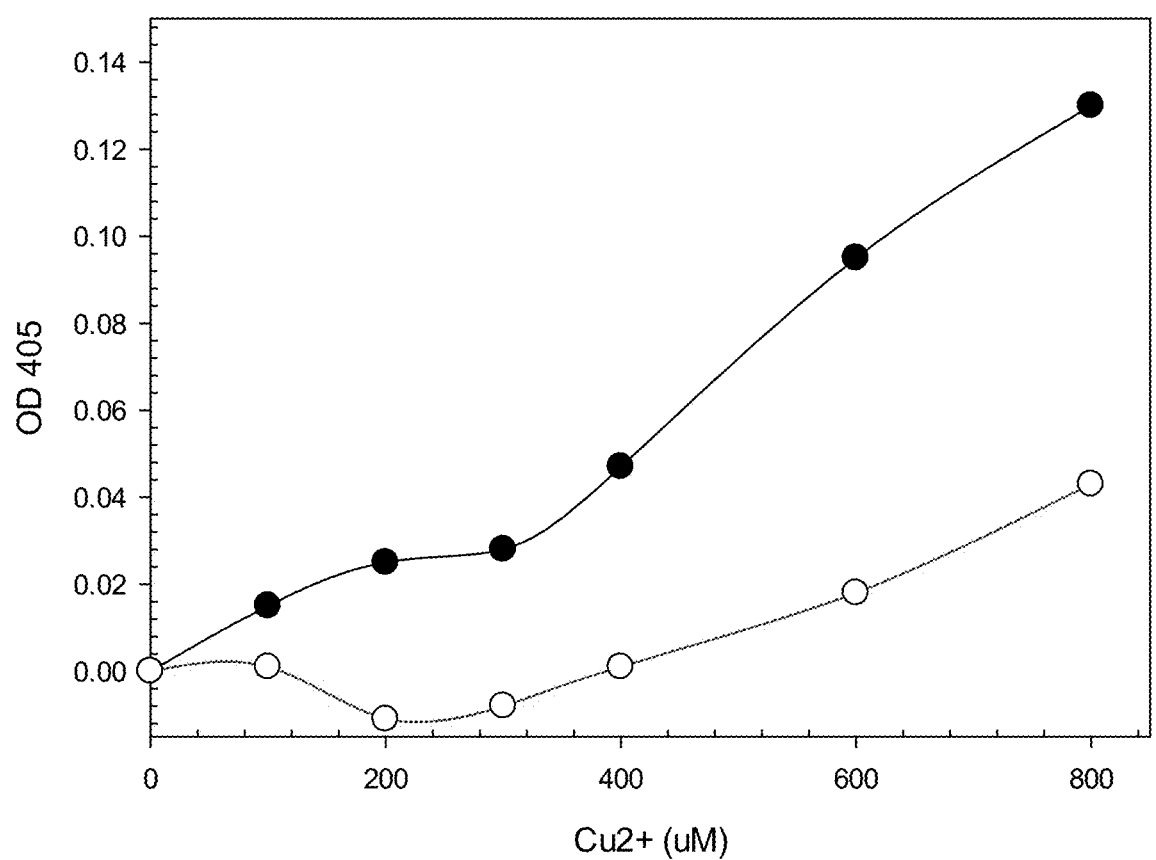
FIG. 15. Shows prevention of Cu2+-induced chromogranin B aggregation by baicalein. Cu2+-induced chromogranin B aggregation (0.005 mg/ml) (0.06 µM) was mostly suppressed by 1 µM baicalein at pH 7.4. Chromogranin B aggregation by increasing concentrations of Cu2+ is expressed in black line (closed circles) while that in the presence of baicalein is expressed in grey line (open circles).
Figure 16:
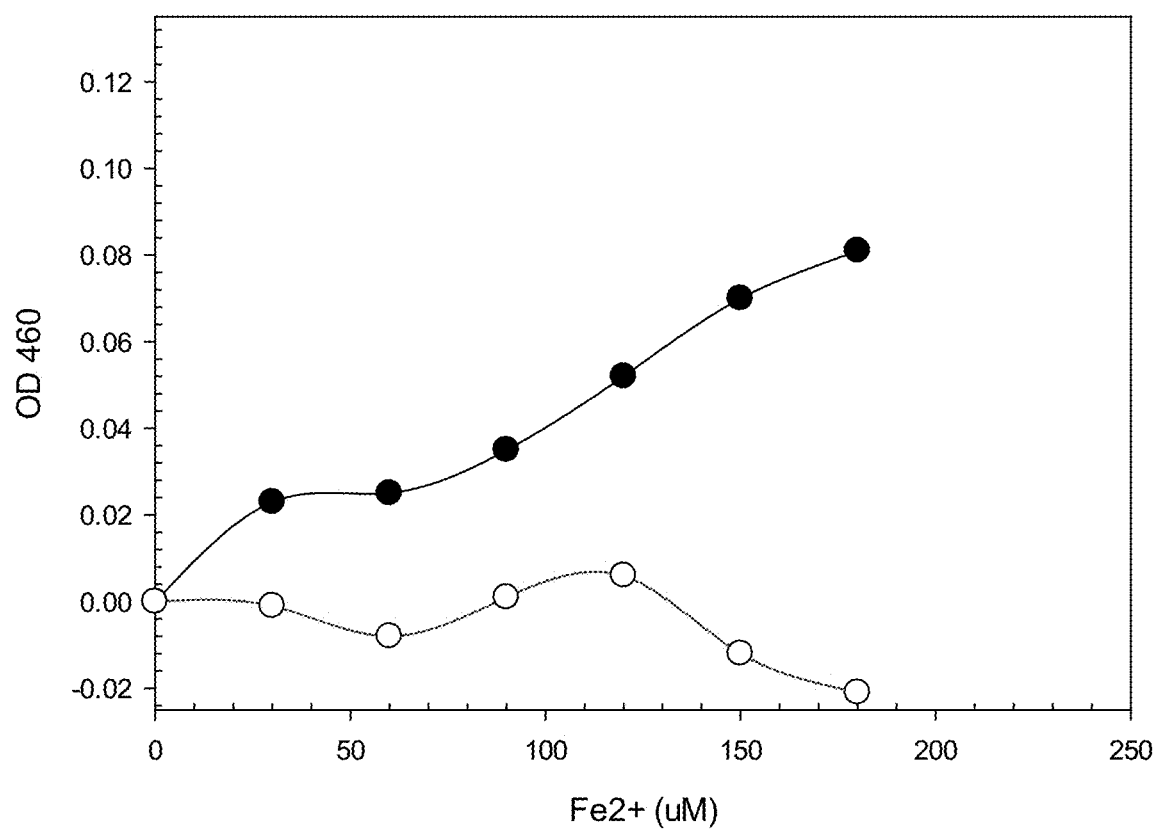
FIG. 16. Shows prevention of Fe2+-induced secretogranin II aggregation by baicalein. Fe2+-induced secretogranin II aggregation (0.01 mg/ml) (0.14 µM) was completely suppressed by 1 µM baicalein at pH 7.4. Secretogranin II aggregation by increasing concentrations of Fe2+ is expressed in black line (closed circles) while that in the presence of baicalein is expressed in grey line (open circles).
Figure 17:
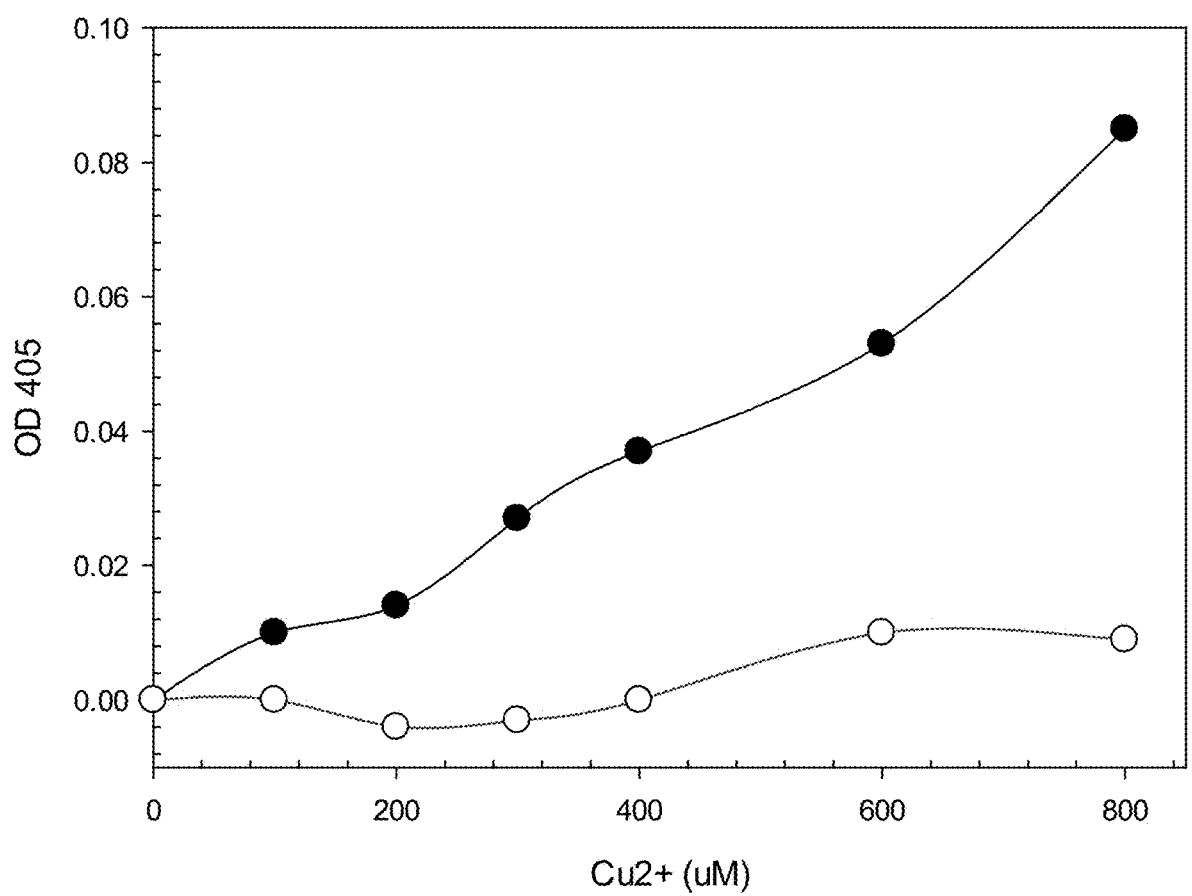
FIG. 17. Shows prevention of Cu2+-induced secretogranin II aggregation by kaempferol. Cu2+-induced secretogranin II aggregation (0.005 mg/ml) (0.07 µM) was mostly suppressed by 1 µM kaempferol at pH 7.4. Secretogranin II aggregation by increasing concentrations of Cu2+ is expressed in black line (closed circles) while that in the presence of baicalein is expressed in grey line (open circles).
Figure 18:
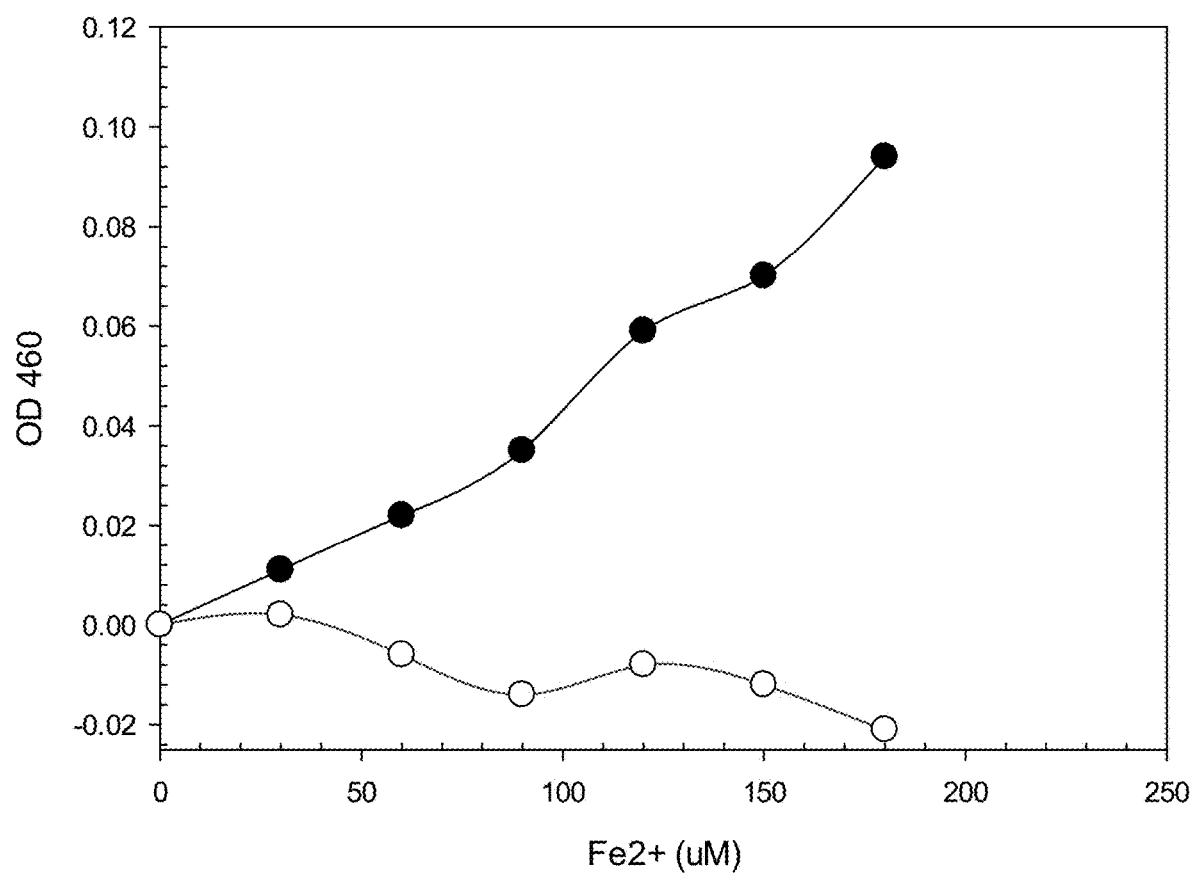
FIG. 18. Shows prevention of Fe2+-induced chromogranin A aggregation by kaempferol. Fe2+-induced chromogranin A aggregation (0.005 mg/ml) (0.1 µM) was completely suppressed by 1 µM kaempferol at pH 7.4. Chromogranin A aggregation by increasing concentrations of Fe2+ is expressed in black line (closed circles) while that in the presence of baicalein is expressed in grey line (open circles).

FIG. 14 shows prevention of $Fe^{2+}$-induced secretogranin II aggregation by luteolin. $Fe^{2+}$-induced secretogranin II aggregation (0.005 mg/ml) (0.07 µM) was mostly inhibited by 1 µM luteolin at pH 7.4. Secretogranin II aggregation by increasing concentrations of $Fe^{2+}$ is expressed in black line (closed circles) while that in the presence of luteolin is expressed in grey line (open circles). From FIG. 14, it is evident that luteolin mostly inhibited the $Fe^{2+}$-induced secretogranin II aggregation. FIG. 15. shows prevention of $Cu^{2+}$-induced chromogranin B aggregation by baicalein. $Cu^{2+}$-induced chromogranin B aggregation (0.005 mg/ml) (0.06 µM) was mostly suppressed by 1 µM baicalein at pH 7.4. Chromogranin B aggregation by increasing concentrations of $Cu^{2+}$ is expressed in black line (closed circles) while that in the presence of baicalein is expressed in grey line (open circles). From FIG. 15, it is evident that baicalein mostly inhibited the $Cu^{2+}$-induced chromogranin B aggregation. FIG. 16 shows prevention of $Fe^{2+}$-induced secretogranin II aggregation by baicalein. $Fe^{2+}$-induced secretogranin II aggregation (0.01 mg/ml) (0.14 µM) was completely suppressed by 1 µM baicalein at pH 7.4. Secretogranin II aggregation by increasing concentrations of $Fe^{2+}$ is expressed in black line (closed circles) while that in the presence of baicalein is expressed in grey line (open circles). From FIG. 16, it is evident that baicalein completely inhibited the $Fe^{2+}$-induced secretogranin II aggregation. FIG. 17 shows prevention of $Cu^{2+}$-induced secretogranin II aggregation by kaempferol. $Cu^{2+}$-induced secretogranin II aggregation (0.005 mg/ml) (0.07 µM) was mostly suppressed by 1 µM kaempferol at pH 7.4. Secretogranin II aggregation by increasing concentrations of $Cu^{2+}$ is expressed in black line (closed circles) while that in the presence of baicalein is expressed in grey line (open circles). From FIG. 17, it is evident that kaempferol mostly inhibited the $Cu^{2+}$-induced secretogranin II aggregation. FIG. 18 shows prevention of $Fe^{2+}$-induced chromogranin A aggregation by kaempferol. $Fe^{2+}$-induced chromogranin A aggregation (0.005 mg/ml) (0.1 µM) was completely suppressed by 1 µM kaempferol at pH 7.4. Chromogranin A aggregation by increasing concentrations of $Fe^{2+}$ is expressed in black line (closed circles) while that in the presence of baicalein is expressed in grey line (open circles). From FIG. 18, it is evident that kaempferol completely inhibited $Fe^{2+}$-induced aggregation of chromogranin A.

Figure 19:
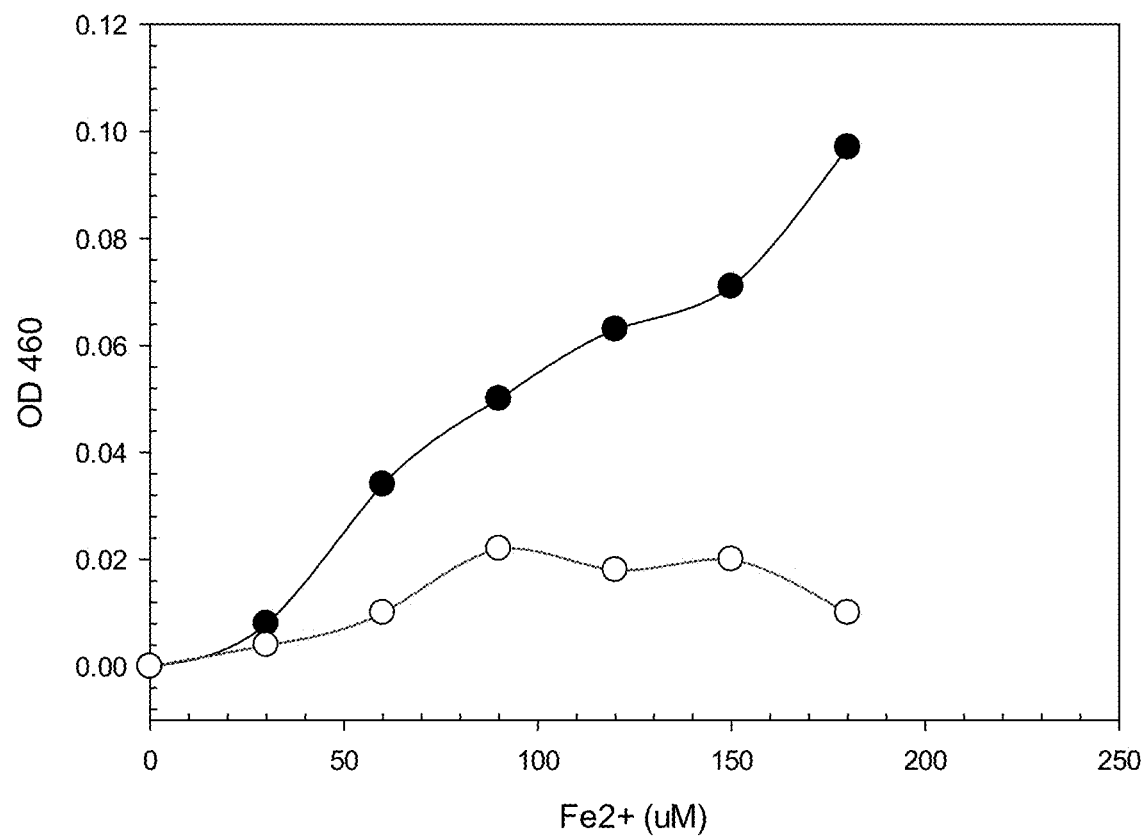
FIG. 19. Shows prevention of Fe2+-induced chromogranin B aggregation by resveratrol. Fe2+-induced chromogranin B aggregation (0.005 mg/ml) (0.06 µM) was mostly suppressed by 1 µM resveratrol at pH 7.4. Chromogranin B aggregation by increasing concentrations of Fe2+ is expressed in black line (closed circles) while that in the presence of resveratrol is expressed in grey line (open circles).
Figure 20:
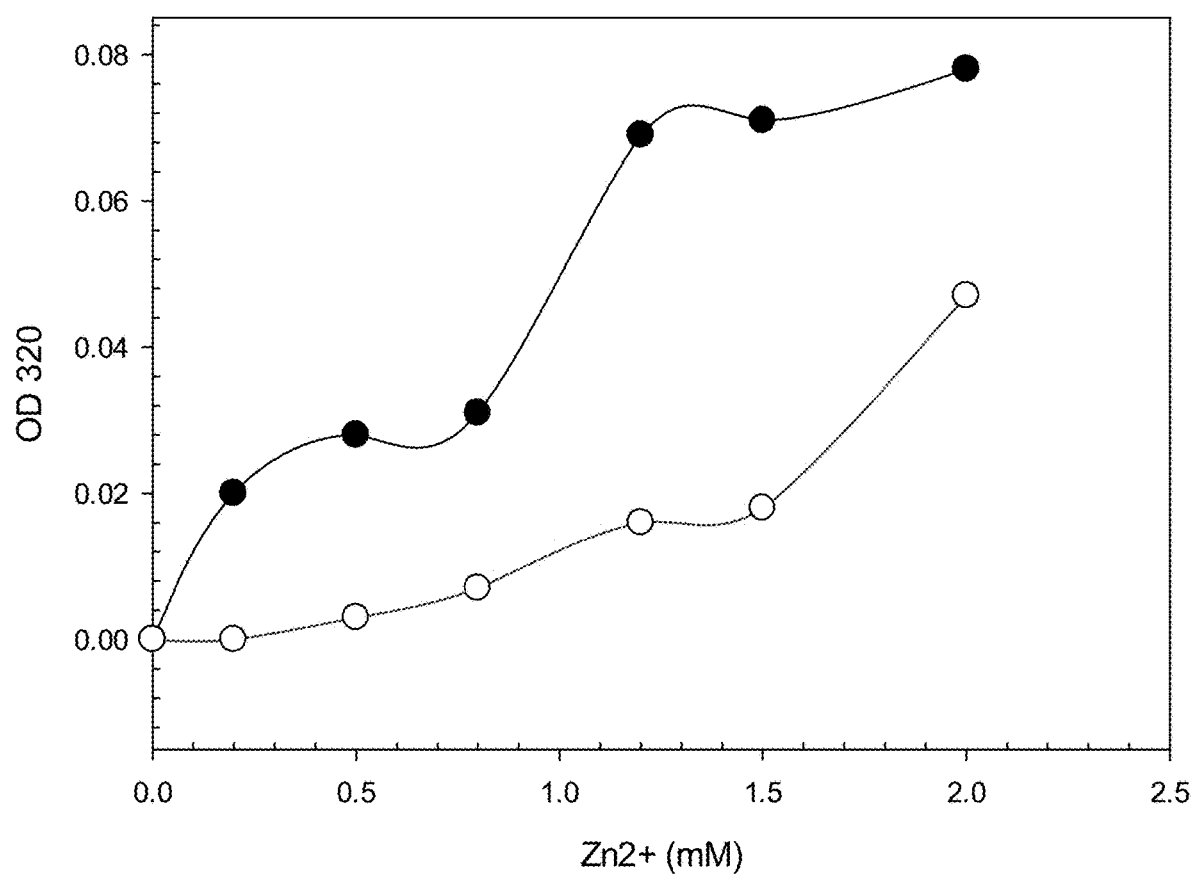
FIG. 20. Shows prevention of Zn2+-induced secretogranin II aggregation by resveratrol. Zn2+-induced secretogranin II aggregation (0.005 mg/ml) (0.07 µM) was significantly suppressed by 1 µM resveratrol at pH 7.4. Secretogranin II aggregation by increasing concentrations of Zn2+ is expressed in black line (closed circles) while that in the presence of resveratrol is expressed in grey line (open circles).
Figure 21:
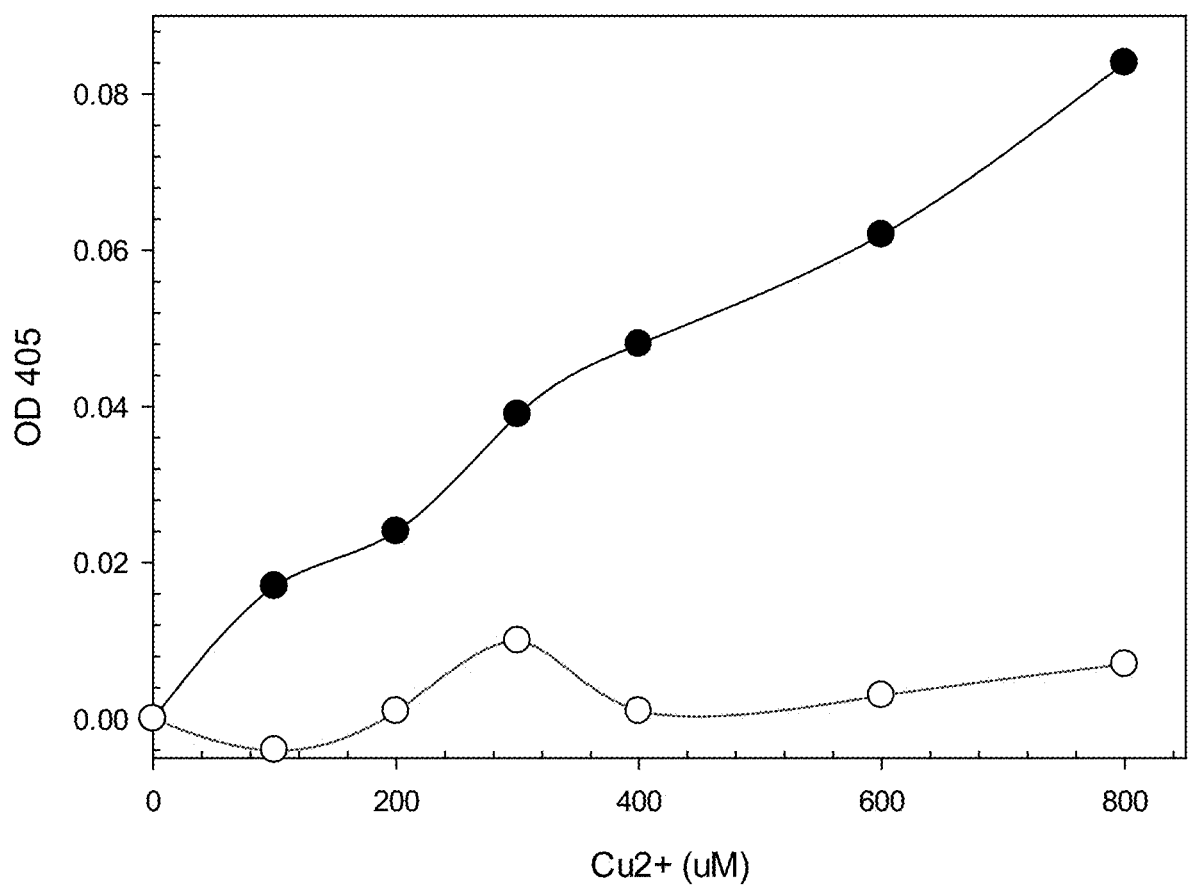
FIG. 21. Shows prevention of Cu2+-induced secretogranin II aggregation by epigallocatechin 3-gallate (EGCG). Cu2+-induced secretogranin II aggregation (0.005 mg/ml) (0.07 µM) was mostly suppressed by 1 µM EGCG at pH 7.4. Secretogranin II aggregation by increasing concentrations of Cu2+ is expressed in black line (closed circles) while that in the presence of EGCG is expressed in grey line (open circles).
Figure 22:
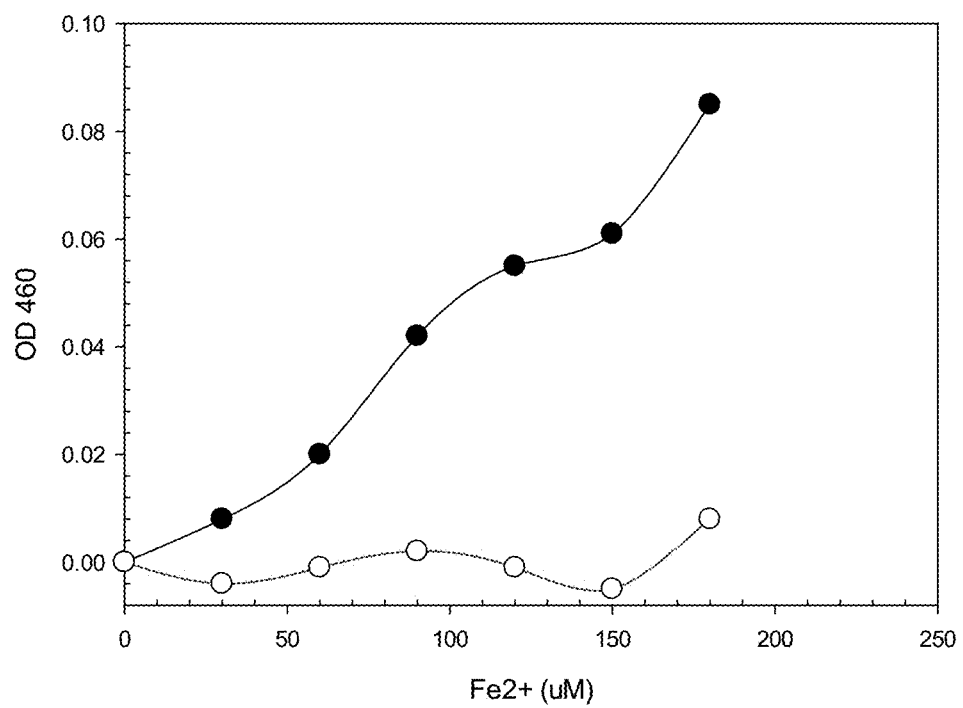
FIG. 22. Shows prevention of Fe2+-induced secretogranin II aggregation by epigallocatechin 3-gallate (EGCG). Fe2+-induced secretogranin II aggregation (0.005 mg/ml) (0.07 µM) was completely suppressed by 1 µM EGCG at pH 7.4. Secretogranin II aggregation by increasing concentrations of Fe2+ is expressed in black line (closed circles) while that in the presence of EGCG is expressed in grey line (open circles).
Figure 23:
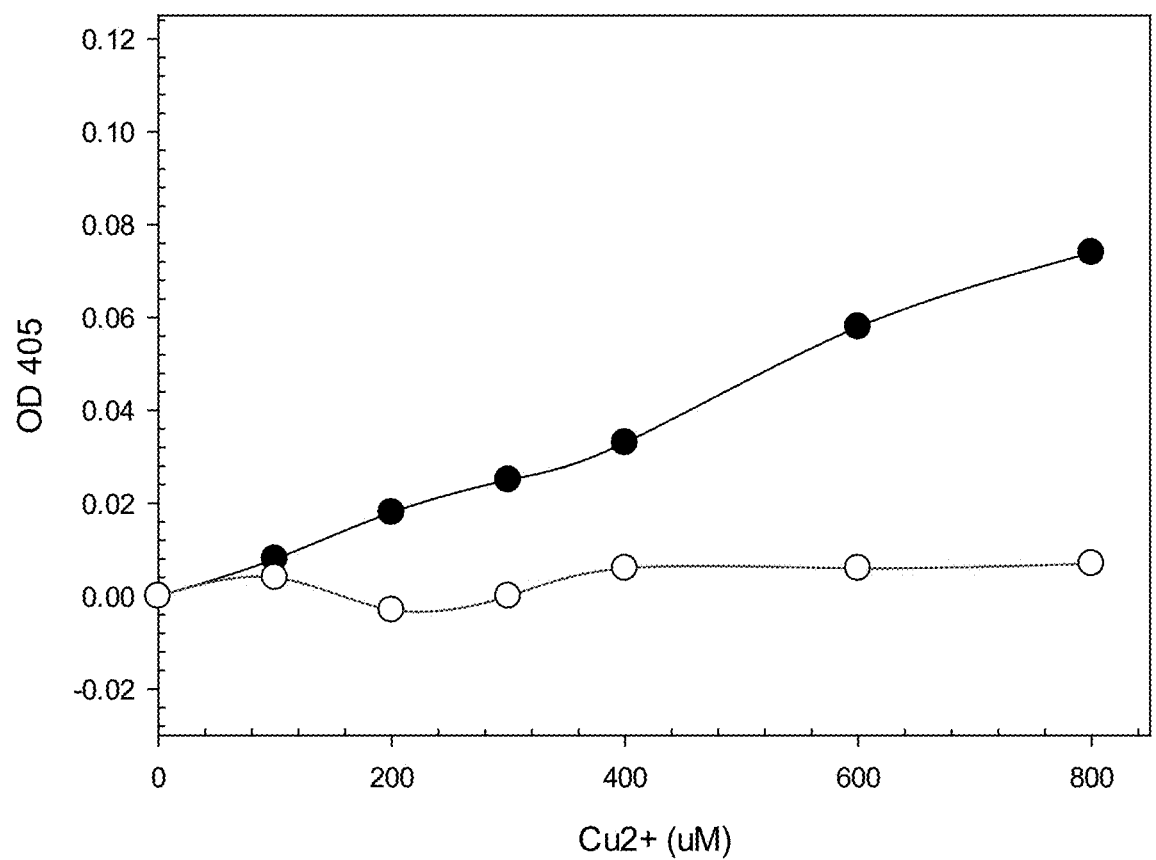
FIG. 23. Shows prevention of Cu2+-induced chromogranin A aggregation by cordycepin. Cu2+-induced chromogranin A aggregation (0.005 mg/ml) (0.1 µM) was mostly suppressed by 1 µM cordycepin at pH 7.4. Chromogranin A aggregation by increasing concentrations of Cu2+ is expressed in black line (closed circles) while that in the presence of cordycepin is expressed in grey line (open circles). Chromogranin A aggregation by Cu2+ was virtually inhibited by cordycepin.
Figure 24:
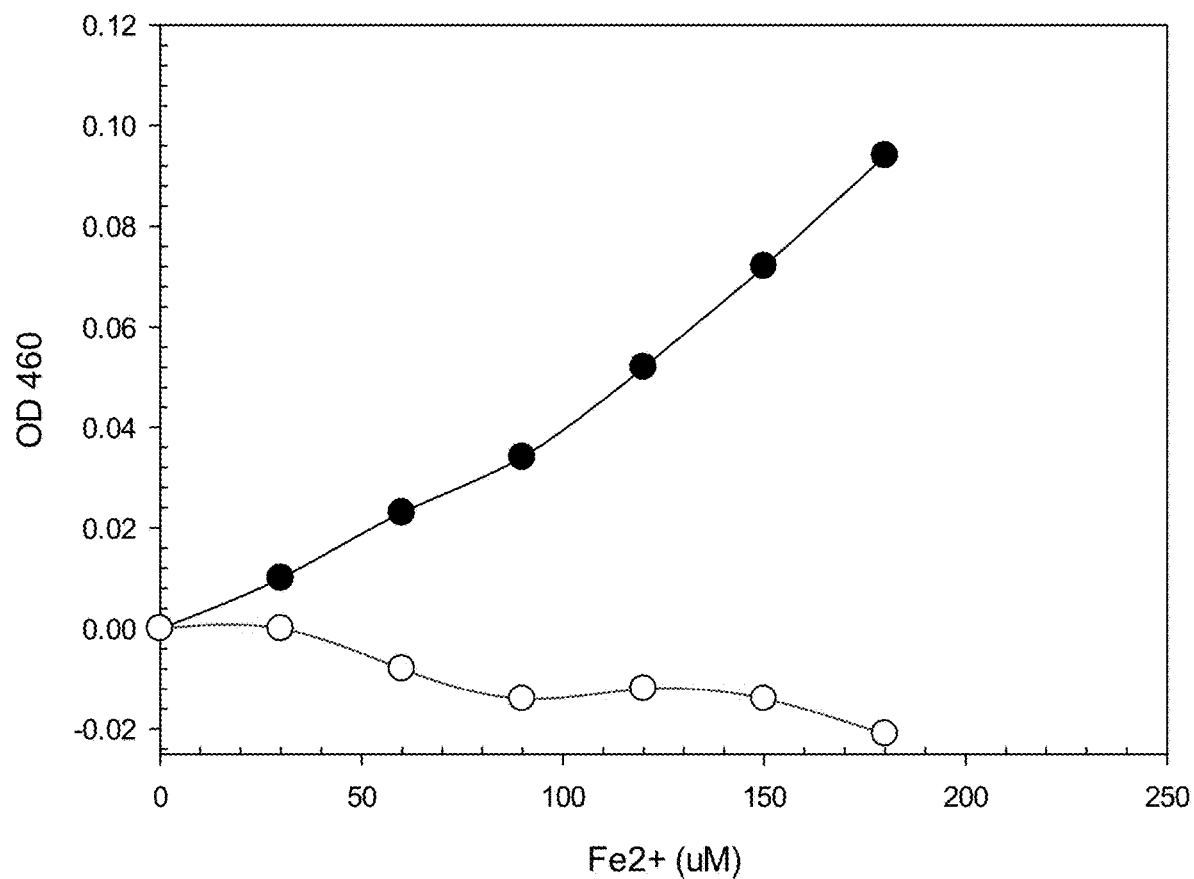
FIG. 24. Shows prevention of Fe2+-induced secretogranin II aggregation by cordycepin. Fe2+-induced secretogranin II aggregation (0.005 mg/ml) (0.07 µM) was significantly suppressed by 1 µM cordycepin at pH 7.4. Secretogranin II aggregation by increasing concentrations of Fe2+ is expressed in black line (closed circles) while that in the presence of cordycepin is expressed in grey line (open circles). Secretogranin II aggregation by Fe2+ was completely inhibited by cordycepin.
Figure 25:
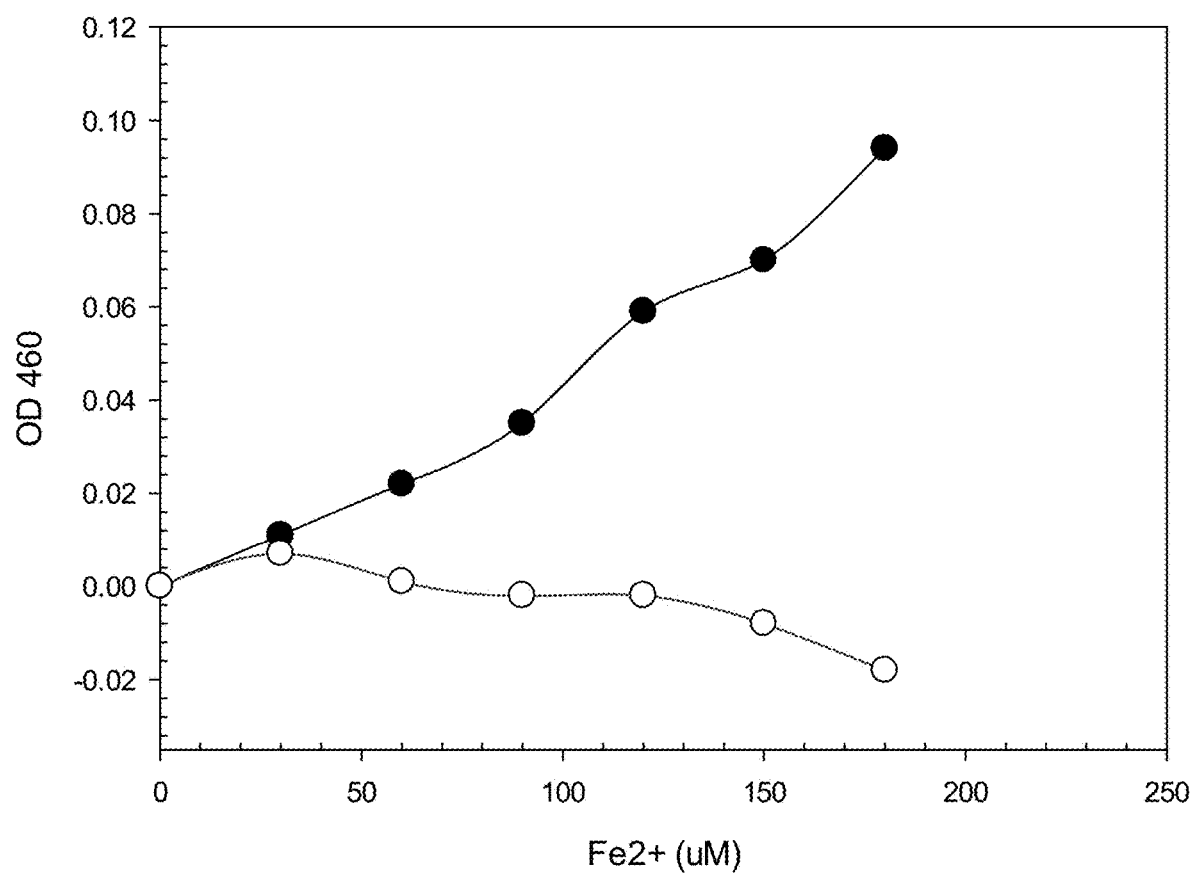
FIG. 25. Shows prevention of Fe2+-induced chromogranin A aggregation by tyrphostin AG1478. Fe2+-induced chromogranin A aggregation (0.005 mg/ml) (0.1 µM) was significantly suppressed by 1 µM tyrphostin AG1478 at pH 7.4. Chromogranin A aggregation by increasing concentrations of Fe2+ is expressed in black line (closed circles) while that in the presence of tyrphostin AG1478 is expressed in grey line (open circles). Chromogranin A aggregation by Fe2+ was completely inhibited by tyrphostin AG1478.
Figure 26:
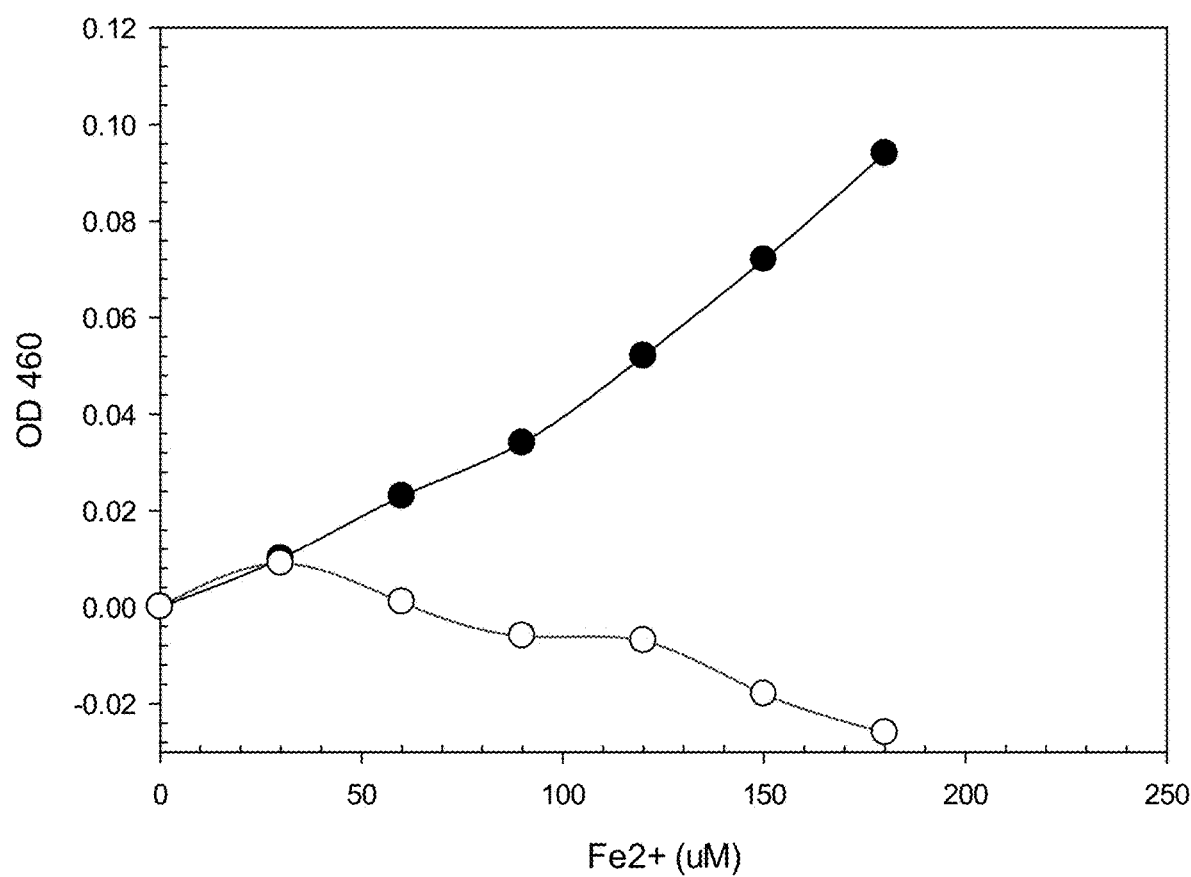
FIG. 26. Shows prevention of Fe2+-induced secretogranin II aggregation by tyrphostin AG1478. Fe2+-induced secretogranin II aggregation (0.005 mg/ml) (0.07 µM) was significantly suppressed by 1 µM tyrphostin AG1478 at pH 7.4. Secretogranin II aggregation by increasing concentrations of Fe2+ is expressed in black line (closed circles) while that in the presence of tyrphostin A is expressed in grey line (open circles). Secretogranin II aggregation by Fe2+ was completely inhibited by tyrphostin AG1478.
Figure 27:
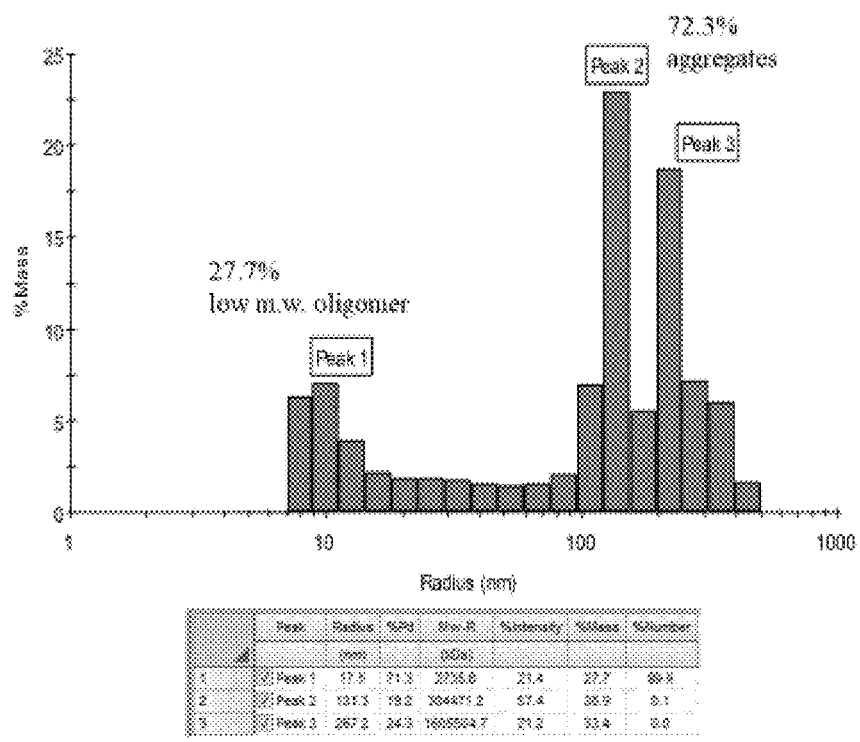
FIG. 27. Shows the distribution profile of hydrodynamic state of chromogranin B in the presence of 0.2 mM Fe2+. The distribution profile of hydrodynamic state of metal-induced granin aggregation was determined with chromogranin B (0.5 mg/ml) in the presence of 0.2 mM Fe2+ using dynamic light scattering method at pH 7.4.

FIG. 19 shows prevention of Fe2+-induced chromogranin B aggregation by resveratrol. Fe2+-induced chromogranin B aggregation (0.005 mg/ml) (0.06 µM) was mostly suppressed by 1 µM resveratrol at pH 7.4. Chromogranin B aggregation by increasing concentrations of Fe2+ is expressed in black line (closed circles) while that in the presence of resveratrol is expressed in grey line (open circles). From FIG. 19, it is evident that resveratrol mostly inhibited the $Fe^{2+}$-induced chromogranin A aggregation. FIG. 20 shows prevention of $Zn^{2+}$-induced secretogranin II aggregation by resveratrol. $Zn^{2+}$-induced secretogranin II aggregation (0.005 mg/ml) (0.07 µM) was significantly suppressed by 1 µM resveratrol at pH 7.4. Secretogranin II aggregation by increasing concentrations of $Zn^{2+}$ is expressed in black line (closed circles) while that in the presence of resveratrol is expressed in grey line (open circles). FIG. 21 shows prevention of $Cu^{2+}$-induced secretogranin II aggregation by EGCG. $Cu^{2+}$-induced secretogranin II aggregation (0.005 mg/ml) (0.07 µM) was mostly suppressed by 1 µM EGCG at pH 7.4. Secretogranin II aggregation by increasing concentrations of $Cu^{2+}$ is expressed in black line (closed circles) while that in the presence of EGCG is expressed in grey line (open circles). From FIG. 21, it is evident that EGCG mostly inhibited the $Cu^{2+}$-induced secretogranin II aggregation. FIG. 22 shows prevention of $Fe^{2+}$-induced secretogranin II aggregation by EGCG. $Fe^{2+}$-induced secretogranin II aggregation (0.005 mg/ml) (0.07 µM) was completely suppressed by 1 µM EGCG at pH 7.4. Secretogranin II aggregation by increasing concentrations of $Fe^{2+}$ is expressed in black line (closed circles) while that in the presence of EGCG is expressed in grey line (open circles). It is evident that EGCG completely inhibited the $Fe^{2+}$-induced secretogranin II aggregation. FIG. 23 shows prevention of $Cu^{2+}$-induced chromogranin A aggregation by cordycepin. $Cu^{2+}$-induced chromogranin A aggregation (0.005 mg/ml) (0.1 µM) was mostly suppressed by 1 µM cordycepin at pH 7.4. Chromogranin A aggregation by increasing concentrations of $Cu^{2+}$ is expressed in black line (closed circles) while that in the presence of cordycepin is expressed in grey line (open circles). Chromogranin A aggregation by $Cu^{2+}$ was virtually inhibited by cordycepin. FIG. 24 shows prevention of $Fe^{2+}$-induced secretogranin II aggregation by cordycepin. $Fe^{2+}$-induced secretogranin II aggregation (0.005 mg/ml) (0.07 µM) was significantly suppressed by 1 µM cordycepin at pH 7.4. Secretogranin II aggregation by increasing concentrations of $Fe^{2+}$ is expressed in black line (closed circles) while that in the presence of cordycepin is expressed in grey line (open circles). Secretogranin II aggregation by $Fe^{2+}$ was completely inhibited by cordycepin. FIG. 25 shows prevention of $Fe^{2+}$-induced chromogranin A aggregation by tyrphostin AG1478. $Fe^{2+}$-induced chromogranin A aggregation (0.005 mg/ml) (0.1 µM) was significantly suppressed by 1 µM tyrphostin AG1478 at pH 7.4. Chromogranin A aggregation by increasing concentrations of $Fe^{2+}$ is expressed in black line (closed circles) while that in the presence of tyrphostin AG1478 is expressed in grey line (open circles). Chromogranin A aggregation by $Fe^{2+}$ was completely inhibited by tyrphostin AG1478. FIG. 26 shows prevention of $Fe^{2+}$-induced secretogranin II aggregation by tyrphostin AG1478. $Fe^{2+}$-induced secretogranin II aggregation (0.005 mg/ml) (0.07 µM) was significantly suppressed by 1 µM tyrphostin AG1478 at pH 7.4. Secretogranin II aggregation by increasing concentrations of $Fe^{2+}$ is expressed in black line (closed circles) while that in the presence of tyrphostin A is expressed in grey line (open circles). Secretogranin II aggregation by $Fe^{2+}$ was completely inhibited by tyrphostin AG1478. FIG. 27 shows the distribution profile of hydrodynamic state of chromogranin B in the presence of 0.2 mM $Fe^{2+}$. The distribution profile of hydrodynamic state of metal-induced granin aggregation was determined with chromogranin B (0.5 mg/ml) in the presence of 0.2 mM Fe2+ using dynamic light scattering method at pH 7.4. Under this solution condition most of chromogranin B (72.3%) stayed in large aggregate state while 27.7% remained in low molecular weight oligomer state. Similar results were also obtained with other granins in the presence of metal ions. This result agrees with the results shown above (FIG. 5-10), confirming the metal-induced aggregation of granins.

Other flavonoids, stilbenoids, and molecules that had been tested in the inhibition of metal-induced granin aggregation as described in FIGS. 11-26 and 36-49 showed similar toxicity-inhibiting results in the identical cell assays (not shown), indicating the efficacy of these inhibitor molecules as the strong drug candidates for AD.

Example 2

Hydrodynamic Studies of Granins

Molecular dynamic light scattering: To determine whether granins are in a monomer-to-oligomer state or in high molecular weight aggregate states in different solution conditions, dynamic light scattering experiments of granins were carried out with a DynaPro NanoStar of Wyatt Technology (Santa Barbara, Calif.) at 24° C., and the results were analyzed by a program (Dynamics 7.5.0) provided by the company.

Figure 28:
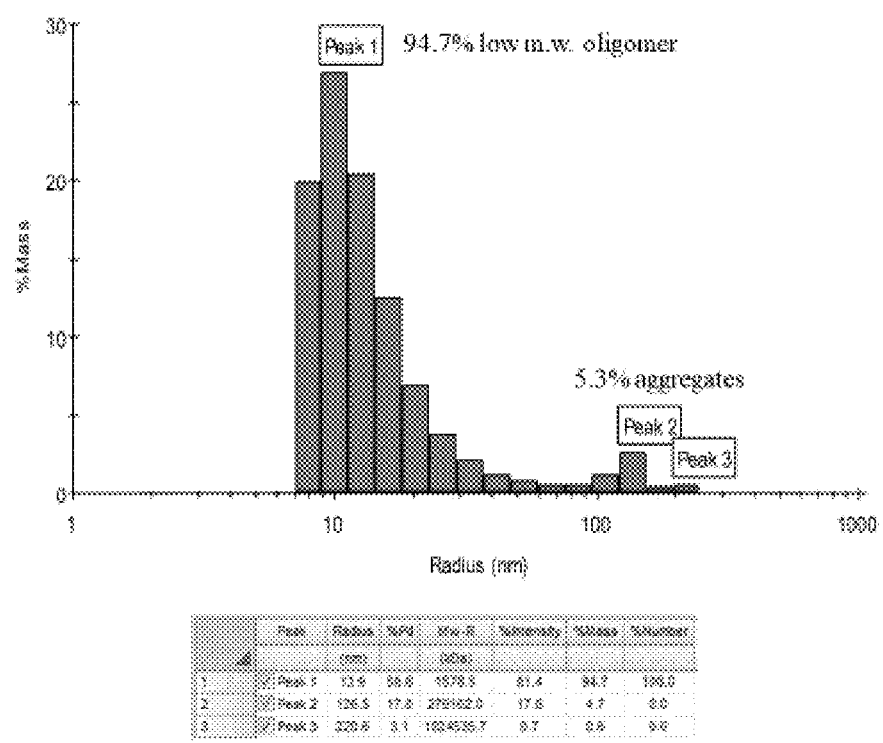
FIG. 28. Shows the distribution profile of hydrodynamic state of chromogranin B in the presence of baicalein, one of the flavonoids, and Fe2+. The distribution profile of hydrodynamic state of metal-induced granin aggregation was determined with chromogranin B (0.5 mg/ml) (6 µM) in the presence of 0.2 mM baicalein and 0.2 mM Fe2+ using dynamic light scattering method at pH 7.4.

FIG. 28. Shows the distribution profile of hydrodynamic state of chromogranin B in the presence of baicalein, one of the flavonoids, and Fe2+. The distribution profile of hydrodynamic state of metal-induced granin aggregation was determined with chromogranin B (0.5 mg/ml) (6 µM) in the presence of 0.2 mM baicalein and 0.2 mM Fe2+ using dynamic light scattering method at pH 7.4. Quite remarkably the vast majority of chromogranin B (94.7%) remained in low molecular weight oligomer state and only a small portion (5.3%) stayed in large aggregate state despite the presence of 0.2 mM Fe2+, which indicates that baicalein prevented chromogranin B from interacting with each other to form large aggregates and/or dissociated the large aggregate state of chromogranin B that was shown in FIG. 27 to low molecular weight oligomer state. Similar results were also obtained with other granins. This result agrees with the results shown above (FIGS. 11-26 and 36-49), and explains why flavonoids, stilbenoids, and some specific molecules inhibit the metal-induced aggregation of granins.

Example 3

Cell Toxicity Studies

In these experiments, selected compounds and agents were applied to the rats to test the effectiveness of these molecules as the therapeutics agents in the granin-induced Alzheimer's Disease (AD) pathogenesis. The compounds tested included flavonoids, stilbenoids, and others.

MTT cell toxicity assay: Cell toxicity assays were done using MTT cell proliferation assay kits from Invitrogen (U.S.A.) and 50,000 PC12 cells/well as described (Cheruvara et al., 2015; Shearman et al., 1994). The assays are designed to detect the level of MTT dye reduction by cells, and the resulting color changes at 570 nm are used as an indicator of cell viability (health). The healthier the cells the higher the color changes.

FIG. 50. Shows cell toxicity of each granin in the presence of 20 µM Cu2+ and 1 µM toxicity inhibitor luteolin. The cell toxicity of each granin (0.1 µM chromogranin A, 0.06 µM chromogranin B, and 0.07 µM secretogranin II) in the presence of 20 µM Cu2+ and in the additional presence of 1 µM luteolin (cf. FIG. 13-14 above), one of the metal-induced granin toxicity inhibitors, was measured using PC12 cells and MTT assays (Cheruvara et al., 2015; Shearman et al., 1994). Luteolin, one of the inhibitors of metal-induced granin aggregation (see FIG. 13-14 above), virtually stopped the granin-induced toxicity.

Four molecules were applied simultaneously to the rats to test the effectiveness of these molecules as the therapeutics agents in the granin-induced Alzheimer's Disease (AD) pathogenesis. Four groups of Wistar rats, 7-9 rats in each group, were used in the animal studies to test the effects of granins in AD pathogenesis and of AD drug candidates via intracerebroventricle injection methods as follows: Group 1 (control); 1 µl of 2 mM MOPS, pH 7.4 was injected into the intracerebroventricle of rat brain (7 rats). Group 2 (granins); 0.1 µM of CGA, CGB, and SgII each in 1 µl of 2 mM MOPS, pH 7.4 were injected into the intracerebroventricle of rat brain (9 rats). Group 3 (granins+metal ions); 0.1 µM of CGA, CGB, and SgII each plus 0.8 mM Cu2+, 250 µM Fe2+, and 2 mM of Zn2+, all in 1 µl of 2 mM MOPS, pH 7.4 were injected into the intracerebroventricle of rat brain (9 rats). Group 4 (granins+metal ions+4 kinds of flavonoids and stilbenoids); 0.1 µM of CGA, CGB, and SgII each, and 0.8 mM Cu2+, 250 µM Fe2+, and 2 mM of Zn2+, plus 1 µM each of 4 kinds of flavonoids, stilbenoids, and other molecules, all in 1 µl of 2 mM MOPS, pH 7.4 were injected into the intracerebroventricle of rat brain (8 rats).

The results presented herein indicate that metal chelators and/or any agents that prevent or suppress the granin aggregation can potentially serve as therapeutic agents for AD by inhibiting or preventing the metal induced aggregation illustrated in FIGS. 5-10. Indeed, flavonoids, stilbenoids and some specific molecules inhibited and/or suppressed the metal-induced aggregation of granins (FIGS. 11-26, 36-49) and were proven to be highly effective in preventing the toxic effects of granins in cells (FIG. 50) and in rat brains (FIG. 30-35, 51-59). It was further confirmed in the dynamic light scattering experiments that metal ions convert the monomer-oligomer state of granins to large aggregates (FIG.

27), i.e., from non-toxic to toxic states, and that the role of flavonoids and other molecules was to prevent the conversion of monomer-oligomer state of granins to large aggregates and/or to dissociate high molecular weight aggregates to a low molecular weight monomer-oligomer state (FIG. 28).

Example 4

Animal Studies

The experiments described below show further that the compounds and compositions provided herein for inhibiting the aggregation of a granin from a low molecular weight form to a high molecular weight aggregated form can potentially serve as the therapeutic agents for Alzheimer's AD and related neurodegenerative diseases Materials and Methods Animal Study: For animal studies, 8 week old Wistar rats, weighing ~280 g to 300 g, were purchased from a local breeder and housed in a specific pathogen free (SPF) animal facility, and used under strict conformity with the rules and regulation of the National Institutes of Health (USA) standards.

Stereotaxic Intracerebroventricular (ICV) Injection into Rat Brain: For this, a guide cannula purchased from Invivo 1 (VA, USA) was inserted into the rat's brain at a specific location, which is 2 mm to the right from the brain center line (from rostrum to cauda) and 0.8 mm to the caudal side from the bregma line (drawn on the bregma perpendicular to the brain center line), at the depth of 2.9 mm of the brain tissue. The injection cannula (Invivo 1, VA) protruded 0.5 mm further into the lateral ventricle from the end of the guide cannula. The first injection of granins and/or test molecules in 1 µl of 2 mM MOPS, pH 7.4 was carried out into the aforementioned right ventricle of the brains when the rats were 3 mo old, and the second injection was done a week thereafter. Control rats were injected with 1 µl of 2 mM MOPS, pH 7.4 at the same time as the experimental group.

Test of Learning Ability and Memory: To determine the effect of injected granins on the rats Morris water maze experiments were carried out for the purpose of testing the learning ability and the memory of each rat. The water tank had a diameter of 135 cm and the water depth was 23 cm with a platform (diameter of 12 cm) that rats can escape to the platform located 15 cm apart from the boundary wall in one quadrant. When the rats were 19-20 weeks (4.5-mo) old, the learning ability of each rat was tested. For this, seven rats in each group (Groups 1-4, cf. above) that appeared normal were trained to swim and find the platform for 5 times altogether over a period of 7-8 days (one training/a day or two) in the 18th-19th week. After the training, the platform was made invisible under 1.5 cm of milk-colored water (total depth, 24.5 cm) and allowed the rats to swim to reach the platform and measured the time required for each rat to reach it. The time required for each rat to arrive at the platform is interpreted to reflect each rat's ability to learn. For memory test, the rats were allowed to learn the location of the platform 3 more times in 3 days (once per day) and then the hidden platform was relocated to the opposite position relative to the environment by turning the water tank 180°. When the rats were allowed to swim starting from the location where the platform had been located and to find the relocated platform, the rats that had clearer memory of the original location of the platform kept searching for the platform for a long time in the original location before they could find the newly relocated platform. Here the time spent for the rats to locate the platform in the newly positioned water tank was used as a measure of memory of each rat.

Figure 29:
FIG. 29. Illustrates a rat with an injection cannula installed in the head and diagram of a frontal section of rat that shows where injection occurred. (Right) The intracerebroventricle of a rat is shown in grey and the location of the injection cannula is shown in grey color in right intracerebroventricle.
Figure 29:
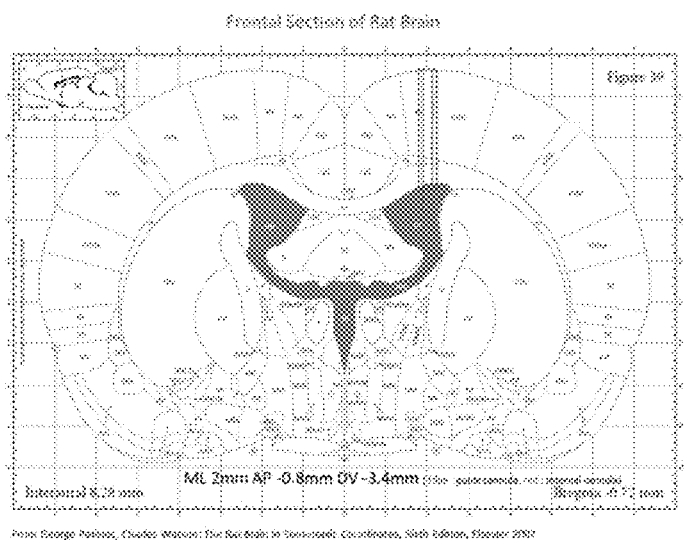

FIG. 29. Illustrates a rat with an injection cannula installed in the head and diagram of a frontal section of rat that shows where injection occurred. (Right) The intracerebroventricle of a rat is shown in blue color and the location of the injection cannula is shown in grey color in right intracerebroventricle. FIG. 30. Search time spent by rats in each group in Morris water maze test. The average time (in seconds) spent by rats in each group to escape to the platform in Morris water maze test was expressed with standard error (n is the number of rats in each group). Note that rats in groups 1 and 4 spent 7-8 s in locating the platform whereas those in group 2 spent 27 s and those in group 3 spent 37 s despite the fact that rats in group 4 had also injected granins and metal ions along with the drug candidates. These results indicate that members of flavonoids and stilbenoids completely prevented granins from exerting harmful effects to the rats, i.e., impairing the learning ability and memory, the hallmark symptoms of AD.

FIG. 31. Shows the representative swimming tracks of rats in different groups. The numbers at the top left indicate the group number and the traces show the swimming tracks of rats from each group. The small circle in lower left quadrant indicates where the rats started to swim to find the platform shown in the large circle in the top right quadrant.

FIG. 32. Shows time spent to find the relocated platform. After sufficient familiarization of the rats as to the location of the platform in Morris water maze test, the platform in the water tank was relocated to the opposite quadrant by turning the water tank 180° and the times required for the rats to find the relocated platform were measured in three different trials with a day gap between each trial. The numbers indicate group number, and the average times of search in seconds are expressed with standard error bars. Note that rats in groups 1 and 4 spent long time (>40 s) in the first trial trying to find the platform in the original location, but once they realized it was moved to a new location their search time was considerably shortened and they could find the platform in 6-8 seconds by the third trial. But this was not the case with the rats in groups 2 and 3 that spent 21-32 s in the first trial and 16-25 s in the third trial, indicating their lack of clear memory.

FIG. 33. Shows the representative swimming tracks of rats in each group. The numbers at the top left indicate the group number and the pink colors show the swimming tracks of rats from each group. The small circles in the top right quadrants indicate where the rats started to swim to find the platform shown in large green circles in the bottom left quadrants. The results apparently show that rats in groups 1 and 4 have markedly superior memory than those of groups 2 and 3, demonstrating clearly not only the harmful (neurodegenerative) effects of injected granins but also the striking effectiveness of the flavonoids and stilbenoids co-injected as the inhibitors (drug candidates) of granin-induced neurodegeneration.

FIG. 34. Shows abnormal posture of some rats injected with granins Some rats in group 3 showed skewed necks 2 weeks after the injection of granins plus metal ions ($Cu^{2+}$, $Zn^{2+}$, and $Fe^{2+}$) while some rats in group 2 started to show skewed necks 4-5 weeks after the injection of granins. No rats in groups 1 and 4 exhibited any abnormal posture and looked normal and healthy until they were old (sacrificed when ~18 months old).

FIG. 35. Shows shrunken hippocampus (right half) of a rat with skewed neck in group 2 (injected with granins). A rat in group 2 (injected with granins) with skewed neck was sacrificed 10 weeks after the injection of granins (6 weeks after the manifestation of skewed neck and 6 months after birth) and the brain tissue was examined. Quite remarkably the right half of hippocampus that is responsible for learning and memory was shown to be considerably shrunken compared to the left half. The right side is where the granins were injected into the right intracerebroventricle of these rats (cf. FIG. 29). Given that shrunken brains (including hippocampi) are the hallmarks of AD patients, it is quite surprising that granins can shrink the brains of young rats (6 months old) in such a short time (10 weeks after the injection of granins).

From the experiments and data described above, we identify 1) granins as the pathogenic agents for AD, 2) metal ions such as Cu2+, Zn2+, and Fe2+ as the cofactor in AD pathogenesis by inducing aggregation of granins in the brain, 3) members of flavonoids, stilbenoids, and their derivatives, and some other molecules as the drug candidates for AD via their ability to inhibit and/or suppress granin aggregation or to dissociate a high molecular weight aggregated form to a low molecular weight form, and 4) further demonstrate members of flavonoids and stilbenoids as the agents that inhibit AD-like symptoms in rats.

From the experiments and data described above, we propose that the following agents can potentially serve as the therapeutic agents for Alzheimer's and related neurodegenerative diseases: 1) any molecules or agents that inhibit or suppress the increase of metal ions, such as $Zn^{2+}$, $Cu^{2+}$, $Fe^{2+}$, and $Ca^{2+}$, in the brain, 2) any molecules (natural products, proteins, nucleic acids, etc.) that interact with granins and prevent or suppress aggregation of granins, and 3) chelators of metal ions and any agents that remove metal ions from granins.

Example 5

In Vitro and In Vivo Studies

Materials and Methods

Materials: The major granin proteins, chromogranin A (CGA), chromogranin B (CGB), and secretogranin II (SgII) were purified from secretory granules of bovine adrenal medulla as described (Park et al., 2002; Yoo, 1995; Yoo and Albanesi, 1990). Chelex 100 was from Bio-Rad, and other chemicals were of highest purity that is commercially available.

Aggregation Experiments: Prior to aggregation studies, it is necessary to remove metal ions that had interacted with granins during purification process from granins through extensive treatments with chelating agents such as Chelex 100 to dissociate the granin aggregates. For metal-induced aggregation studies, Chelex 100-treated CGA, CGB, or SgII in 2 mM MOPS, pH 7.4, was titrated with concentrated metal ions such as $CuCl_2$, $FeCl_2$, and $ZnCl_2$. Aggregation was monitored by measuring the turbidity change with a Beckman spectrophotometer. All the measurements were done at 24° C.

Molecular dynamic light scattering: To determine whether granins are in a monomer-to-oligomer state or in high molecular weight aggregate states in different solution conditions, dynamic light scattering experiments of granins were carried out with a DynaPro NanoStar of Wyatt Technology (Santa Barbara, Calif.) at 24° C., and the results were analyzed by a program (Dynamics 7.5.0) provided by the company.

Animal Study: For animal studies, 8 week old Wistar rats, weighing ~280 g to 300 g, were purchased from a local breeder and housed in a specific pathogen free (SPF) animal facility, and used under strict conformity with the rules and regulation of the National Institutes of Health (USA) standards.

Stereotaxic intracerebroventricular (ICV) injection into rat brain: For this, a guide cannula purchased from Invivo 1 (VA, USA) was inserted into the rat's brain at a specific location, which is 2 mm to the right from the brain center line (from rostrum to cauda) and 0.8 mm to the caudal side from the bregma line (drawn on the bregma perpendicular to the brain center line), at the depth of 2.9 mm of the brain tissue. The injection cannula (Invivo 1, VA) protruded 0.5 mm further into the lateral ventricle from the end of the guide cannula. The first injection of granins and/or test molecules in 1 µl of 2 mM MOPS, pH 7.4 was carried out into the aforementioned right ventricle of the brains when the rats were 3 mo old, and the second injection was done a week thereafter. Control rats were injected with 1 µl of 2 mM MOPS, pH 7.4 at the same time as the experimental group.

Test of Learning Ability and Memory: To determine the effect of injected granins on the rats Morris water maze experiments were carried out for the purpose of testing the learning ability and the memory of each rat. The water tank had a diameter of 135 cm and the water depth was 23 cm with a platform (diameter of 12 cm) that rats can escape to the platform located 15 cm apart from the boundary wall in one quadrant. When the rats were 19-20 weeks (4.5-mo) old, the learning ability of each rat was tested. For this, seven rats in each group (Groups 1-4, cf. above) that appeared normal were trained to swim and find the platform for 5 times altogether over a period of 7-8 days (one training/a day or two) in the 18th-19th week. After the training, the platform was made invisible under 1.5 cm of milk-colored water (total depth, 24.5 cm) and allowed the rats to swim to reach the platform and measured the time required for each rat to reach it. The time required for each rat to arrive at the platform is interpreted to reflect each rat's ability to learn. For memory test, the rats were allowed to learn the location of the platform 3 more times in 3 days (once per day) and then the hidden platform was relocated to the opposite position relative to the environment by turning the whole tank 180°. When the rats were allowed to swim starting from the location where the platform had been located and to find the relocated platform, the rats that had clearer memory of the original location of the platform kept searching for the platform for a long time in the original location before they could find the newly relocated platform. Here the time spent for the rats to locate the platform in the newly positioned water tank was used as a measure of memory of each rat.

Histochemical study of the brain: To examine whether the granin-injected rat brains are affected by the granins, the brains of the rats were taken out, sectioned in thin slices and stained for examination.

Results

Prevention of Zn2+-induced chromogranin B aggregation by apigenin. For the experiment with the results set forth in FIG. 36 Zn2+-induced chromogranin B aggregation (0.005 mg/ml) was mostly suppressed by 1 µM apigenin at pH 7.4. Chromogranin B aggregation by increasing concentrations of Zn2+ is expressed in black line (closed circles) while that in the presence of apigenin is expressed in grey line (open circles). Based on this experiment, apigenin mostly inhibited Zn2+-induced aggregation of chromogranin B.

Prevention of Cu2+-induced chromogranin A aggregation by apigenin. For the experiment with the results set forth in FIG. 37, Cu2+-induced chromogranin A aggregation (0.005 mg/ml) (0.1 µM) was completely suppressed by 1 µM apigenin at pH 7.4. Chromogranin A aggregation by increasing concentrations of Cu2+ is expressed in black line (closed circles) while that in the presence of apigenin is expressed in grey line (open circles). Based on this experiment, apigenin completely inhibited Cu2+-induced aggregation of chromogranin A.

Prevention of Fe2+-induced chromogranin B aggregation by tangeretin. For the experiment with the results set forth in FIG. 38, Fe2+-induced chromogranin B aggregation (0.005 mg/ml) (0.06 µM) was completely suppressed by 1 µM tangeretin at pH 7.4. Chromogranin B aggregation by increasing concentrations of Fe2+ is expressed in black line (closed circles) while that in the presence of tangeretin is expressed in grey line (open circles). Based on this experiment, tangeretin completely inhibited Fe2+-induced aggregation of chromogranin B.

Prevention of Cu2+-induced chromogranin A aggregation by tangeretin. For the experiment with the results set forth in FIG. 39, Cu2+-induced chromogranin A aggregation (0.005 mg/ml) (0.1 µM) was mostly suppressed by 1 µM tangeretin at pH 7.4. Chromogranin A aggregation by increasing concentrations of Cu2+ is expressed in black line (closed circles) while that in the presence of tangeretin is expressed in grey line (open circles). Based on this experiment, tangeretin mostly inhibited Cu2+-induced aggregation of chromogranin A.

Prevention of Cu2+-induced chromogranin B aggregation by quercetin. For the experiment with the results set forth in FIG. 40, Cu2+-induced chromogranin B aggregation (0.005 mg/ml) (0.06 µM) was completely suppressed by 1 µM quercetin at pH 7.4. Chromogranin B aggregation by increasing concentrations of Cu2+ is expressed in black line (closed circles) while that in the presence of quercetin is expressed in grey line (open circles). Based on this experiment, quercetin completely inhibited Cu2+-induced aggregation of chromogranin B.

Prevention of Fe2+-induced secretogranin II aggregation by quercetin. For the experiment with the results set forth in FIG. 41, Fe2+-induced secretogranin II aggregation (0.005 mg/ml) (0.07 µM) was completely suppressed by 1 µM quercetin at pH 7.4. Secretogranin II aggregation by increasing concentrations of Fe2+ is expressed in black line (closed circles) while that in the presence of quercetin is expressed in grey line (open circles). Based on this experiment, quercetin completely inhibited Fe2+-induced aggregation of secretogranin II.

Prevention of Fe2+-induced chromogranin A aggregation by fisetin. For the experiment with the results set forth in FIG. 42, Fe2+-induced chromogranin A aggregation (0.005 mg/ml) (0.1 µM) was completely suppressed by 1 µM fisetin at pH 7.4. Chromogranin A aggregation by increasing concentrations of Fe2+ is expressed in black line (closed circles) while that in the presence of fisetin is expressed in grey line (open circles). Based on this experiment, fisetin mostly inhibited Fe2+-induced aggregation of chromogranin A.

Prevention of Fe2+-induced secretogranin II aggregation by fisetin. For the experiment with the results set forth in FIG. 43, Fe2+-induced secretogranin II aggregation (0.005 mg/ml) was completely suppressed by 1 µM fisetin at pH 7.4. Secretogranin II aggregation by increasing concentrations of Fe2+ is expressed in black line (closed circles) while that in the presence of fisetin is expressed in grey line (open circles). Based on this experiment, fisetin completely inhibited Fe2+-induced aggregation of secretogranin II.

Prevention of Fe2+-induced chromogranin A aggregation by myricetin. For the experiment with the results set forth in FIG. 44, Fe2+-induced chromogranin A aggregation (0.005 mg/ml) (0.1 µM) was completely suppressed by 1 µM myricetin at pH 7.4. Chromogranin A aggregation by increasing concentrations of Fe2+ is expressed in black line (closed circles) while that in the presence of myricetin is expressed in grey line (open circles). Based on this experiment, myricetin completely inhibited Fe2+-induced aggregation of chromogranin A.

Prevention of Fe2+-induced chromogranin B aggregation by myricetin. For the experiment with the results set forth in FIG. 45, Fe2+-induced chromogranin B aggregation (0.005 mg/ml) was completely suppressed by 1 µM myricetin at pH 7.4. Chromogranin B aggregation by increasing concentrations of Fe2+ is expressed in black line (closed circles) while that in the presence of myricetin is expressed in grey line (open circles). Based on this experiment, myricetin completely inhibited Fe2+-induced aggregation of chromogranin B.

Prevention of Fe2+-induced chromogranin A aggregation by morin. For the experiment with the results set forth in FIG. 46, Fe2+-induced chromogranin A aggregation (0.005 mg/ml) was completely suppressed by 1 µM morin at pH 7.4. Chromogranin A aggregation by increasing concentrations of Fe2+ is expressed in black line (closed circles) while that in the presence of morin is expressed in grey line (open circles). Based on this experiment, morin completely inhibited Fe2+-induced aggregation of chromogranin A.

Prevention of Zn2+-induced chromogranin A aggregation by morin. For the experiment with the results set forth in FIG. 47, Zn2+-induced chromogranin A aggregation (0.005 mg/ml) was mostly suppressed by 1 µM morin at pH 7.4. Chromogranin A aggregation by increasing concentrations of Zn2+ is expressed in black line (closed circles) while that in the presence of morin is expressed in grey line (open circles). Based on this experiment, morin mostly inhibited Zn2+-induced aggregation of chromogranin A.

Prevention of Zn2+-induced chromogranin A aggregation by 5,7-demethoxyflavone. For the experiment with the results set forth in FIG. 48, Zn2+-induced chromogranin A aggregation (0.005 mg/ml) was mostly suppressed by 1 µM 5,7-dimethoxyflavone at pH 7.4. Chromogranin A aggregation by increasing concentrations of Zn2+ is expressed in black line (closed circles) while that in the presence of 5,7-dimethoxyflavone is expressed in grey line (open circles). Based on this experiment, 5,7-dimethoxyflavone mostly inhibited Zn2+-induced aggregation of chromogranin A.

Prevention of Fe2+-induced chromogranin A aggregation by 5,7-demethoxyflavone. For the experiment with the results set forth in FIG. 49, Fe2+-induced chromogranin A aggregation (0.005 mg/ml) was completely suppressed by 1 µM 5,7-dimethoxyflavone at pH 7.4. Chromogranin A aggregation by increasing concentrations of Fe2+ is expressed in black line (closed circles) while that in the presence of 5,7-dimethoxyflavone is expressed in grey line (open circles). Based on this experiment, 5,7-dimethoxyflavone completely inhibited Fe2+-induced aggregation of chromogranin A.

Cell toxicity of each granin in the presence of 20 µM Cu2+ and 1 µM toxicity inhibitor luteolin as seen in FIG. 50.

The cell toxicity of each granin (0.1 µM chromogranin A, 0.06 µM chromogranin B, and 0.07 µM secretogranin II) in the presence of 20 µM $Cu^{2+}$ and in the additional presence of 1 µM luteolin, one of the metal-induced granin toxicity inhibitors, was measured using PC12 cells and MTT assays. Luteolin, one of the inhibitors of metal-induced granin aggregation virtually stopped the granin-induced toxicity. Other flavonoids, stilbenoids, and molecules that had been tested in the inhibition of metal-induced granin aggregation as described in FIGS. 11-26 and 36-49. As seen in the other experiment, they showed similar toxicity-inhibiting results in the identical cell assays (not shown), foretelling the efficacy of these inhibitor molecules as the strong drug candidates for AD.

In FIG. 51, the search time spent by rats in each group in Morris water maze test 2.5-mo after intraventricular injection is shown. The average time (in seconds) spent by rats in each group to escape to the platform was expressed with standard error (n is the number of rats in each group). Note that rats in groups 1 and 4 spent 6.0-6.5 s in locating the platform whereas those in group 2 spent 16.8 s and those in group 3 spent 13.3 s, implying that rats in group 3 recovered from the granin-induced toxicity a bit faster than group 2 rats. Based on these experiments, it was seen that members of flavonoids and stilbenoids completely prevented granins from exerting harmful effects to the rats, i.e., impairing the learning ability and memory, the hallmark symptoms of AD, even 2.5-mo after the granin injection.

In FIG. 52, the representative swimming tracks of rats in each group from FIG. 51 are shown. The numbers at the top left indicate the group number and the traces show the swimming tracks of rats from each group. The small circle in lower left quadrant indicates where the rats started to swim to find the platform shown in large circle in top right quadrant.

FIGS. 53(*a*) and 53(*b*) show the frontal sections of the hippocampus from 10.5 month old rats with and without AD-like symptoms. FIG. 53(*a*), the brain sections of 10.5 month old (7.5-mo after the granin injection) rats were stained with haematoxylin, and the hippocampus of control (group 1), granin-injected (group 2), granins plus metal ions-injected (group 3), and granins, metal ions plus disaggregation compounds-injected (group 4) rats were compared. The hippocampus of group 2 rats showed numerous large hollow spaces, which are the signs of dead cell, followed by that of group 3 rats. There were significantly fewer signs of dead cells in the hippocampus of control rats (group 1) compared to groups 2 and 3 rats. Additionally, there were very few hollow spaces in the hippocampus of group 4 rats, much fewer than those of control rats, which apparently demonstrated well preserved integrity of the hippocampus of group 4 rats. FIG. 53(*b*) shows higher magnification views of approximately the same areas of hippocampus from 53(*a*). Bar=100 µm.

FIG. 54 shows the frontal sections of the cortex from 10.5 month old rats with and without AD-like symptoms. The brain sections of 10.5 month old rats were stained with haematoxylin, and the cortex of control (group 1), granin-injected (group 2), granins plus metal ions-injected (group 3), and granins, metal ions plus disaggregation compounds-injected (group 4) rats were compared. The cortex of group 2 rats showed numerous large hollow spaces, which are the signs of dead cell, followed by that of group 3 rats. Like the hippocampus, there were significantly fewer signs of dead cells in the cortex of control rats (group 1) compared to groups 2 and 3 rats. But in the cortex of group 4 rats there were very few hollow spaces, drastically fewer than those of control rats. Group 4 rats had a well-preserved integrity of the cortex. Bar=100 µm.

FIG. 55 shows a comparison of the brain tissue density in 10.5 month old rats with and without AD-like symptoms. There were significant differences in the brain tissue densities between the rats with and without the AD-like symptoms. The brain tissue densities of the rats that express AD-like symptoms (groups 2 and 3) were significantly reduced, decreasing by ~10-25% compared to the control rats. The brain tissue densities of group 4 rats increased by ~3-4%, indicating that the disaggregation compounds which were injected along with granins and metal ions protected the integrity of the brain cells. Data are averages of 4 measurements of different areas of the cortex and hippocampus and expressed as average±s.e. relative to the controls.

FIG. 56, shows the immunostaining of the hippocampus from 10.5 month old rats with chromogranin A-specific antibody. The brain sections of 10.5 month old rats were immunostained with chromogranin A-specific antibody, and the hippocampus of all four groups of rats were compared. There were numerous chromogranin A-containing plaques in the hippocampus and cortex (not shown). Yet there were far more chromogranin A-containing plaques in the groups 1 and 2 rats than those in groups 3 and 4 rats though the plaques in group 1 rats were significantly smaller. Moreover, the chromogranin A-containing plaques as well as the tissue holes, which are the sign of dead cells, were larger in groups 2 and 3 than in groups 1 and 4. The granin-containing plaques in group 3 brains were notably the largest and often appeared insulated in hollow spaces. The chromogranin A-containing plaques in group 4 rats were rare and the brain tissues looked well preserved with fewer holes than even the control brain tissues. Bar=50 µm.

FIG. 57 shows the immunostaining of hippocampus from 10.5 month old rats with chromogranin B-specific antibody. The brain sections of 10.5 month old rats were immunostained with chromogranin B-specific antibody, and the hippocampus of four groups of rats were compared. There were numerous chromogranin B-containing plaques in the hippocampus and cortex (not shown). There were far more chromogranin B-containing plaques in the groups 1 and 2 rats than those in groups 3 and 4 rats though the plaques in group 1 rats were significantly smaller. The chromogranin B-containing plaques as well as the tissue holes were larger in groups 2 and 3 than in groups 1 and 4. The granin-containing plaques in group 3 brains were the largest and frequently appeared insulated in hollow spaces. Similar to chromogranin A, the chromogranin B-containing plaques in group 4 rats were rare and the brain tissues looked well preserved with fewer holes than even those of the control group. Bar=50 µm.

FIG. 58 shows the immunostaining of hippocampus from 10.5 month old rats with secretogranin II-specific antibody. The brain sections of 10.5 month old rats were immunostained with secretogranin II-specific antibody, and the hippocampus of four groups of rats were compared. There were numerous secretogranin II-containing plaques in the hippocampus and cortex (not shown). There were far more secretogranin II-containing plaques in the groups 1 and 2 rats than those in groups 3 and 4 rats though the plaques in group 1 rats were significantly smaller. The secretogranin II-containing plaques as well as the tissue holes were larger in groups 2 and 3 than in groups 1 and 4. As shown before, the granin-containing plaques in group 3 brains were large, compact, and often appeared insulated in hollow spaces. Analogous to other granins, the secretogranin II-containing plaques in group 4 rats were rare and the brain tissues looked well preserved with fewer holes than even those of the control group. Bar=50 μm.

FIG. 59, shows a comparison of mobile activity of the 11.5 month old rats with and without AD-like symptoms. The mobile activity of the rats was measured using a spinning wheel in which each rat's activity time was the duration each rat is engaged in spinning the wheel. In addition, the length of time each rat can hang on to the wheel when it was moved 90° forward or backward was considered as activity as well. The control rats (group 1) engaged in 17.5 s of activity out of 2 min. Those with AD-like symptoms (groups 2 and 3) did so for 11.2 s and 14.2 s, respectively. The group 4 rats that had been injected with the disaggregation compounds engaged in 23.5 s of activity, substantially longer than that of control rats. There were 4 rats in each group and the measurements were made 4 different times, and the data are expressed as average±s.e.

The results shown herein demonstrate that granins can induce AD-like symptoms; which include, 1) impaired learning ability, 2) impaired memory, 3) accelerated loss of brain cells, 4) accelerated development of granin-containing senile plaques in the brain, and 5) reduced mobile activity, the hallmarks of AD. The results shown herein demonstrate an inhibition of granin-induced AD-like symptoms in rats by simultaneous application of four molecules of flavonoids and stilbenoids.

A composition for inhibiting the aggregation of a granin from a low molecular weight form to a high molecular weight aggregated form, the composition comprising at least two of the following: scutellarein, luteolin, baicalein, kaempferol, quercetin, apigenin, tangeretin, myricetin, fisetin, morin, resveratrol, EGCG, cordycepin, 5,7-dimethoxyflavone, and tyrphostin AG1478.

A composition according to claim 1, comprising at least four of the following: scutellarein, luteolin, baicalein, kaempferol, quercetin, resveratrol, EGCG, cordycepin, and tyrphostin AG1478.

A composition according to claim 1, comprising the following: scutellarein, luteolin, baicalein, kaempferol, resveratrol, and EGCG.

A composition according to claim 1, comprising the following: scutellarein, luteolin, baicalein, kaempferol, quercetin, resveratrol, EGCG, cordycepin, and tyrphostin AG1478.

A composition according to claim 1, wherein the granin comprises one or more of the following: chromogranin A (CGA), chromgranin B (CGB), secretogranin II (SgII) and secretogranin III (SgIII).

A composition according to claim 1, further comprising one or more agent that reduces, inhibits, suppress, or sequesters one of more of the following metal ions Zn2+, Cu2+, Fe2+ and Ca2+ in the nervous system of an animal, the agent selected from the following metalloproteins, Zn2+ binding and sequestering molecules, casein, albumin, zinc finger transcription factors, Cu2+ binding and sequestering molecules, ceruloplasmin, casein, albumin, Fe2+ binding and sequestering molecules, calmodulin, troponin, ferritin, transferrin, lactoferrin, and anthocyanin.

A composition according to claim 1 further comprising a chelator of a metal ion selected from Zn2+, Cu2+, or Fe2+.

A composition according to claim 1, wherein the composition is effective to inhibit the aggregation of a granin from a low molecular weight form to a high molecular weight aggregated form and/or to dissociate a high molecular weight aggregated form to a low molecular weight form in an animal.

A composition for inhibiting the aggregation of a granin from a low molecular weight form to a high molecular weight aggregated form and/or dissociating a high molecular weight aggregated form to a low molecular weight form, the composition comprising i) an anthoxanthin selected from scutellarein, luteolin, baicalein, kaempferol, quercetin, apigenin, tangeretin, myricetin, fisetin, and ii) a stilbenoid selected from resveratrol, piceatannolin, pinosylvin, pterostilbene, astringin, piceid, iii) a flavan selected from epigallocatechin 3-gallate (EGCG), catechin, gallocatechin, catechin 3-gallate, gallocatechin 3-gallate, epicatechin, epigallocatechin, epicatechin 3-gallate, theaflavin-3-gallate, theaflavin-3'-gallate, theaflavin-3,3'-gallate, thearubigin, and proanthocyanidins. and iv) a compound selected from cordycepin, tyrphostin AG1478, and 5,7-dimethoxyflavone.

A composition for inhibiting the interaction of granins with metal ions, the composition comprising at least two of the following: scutellarein, luteolin, baicalein, kaempferol, quercetin, resveratrol, EGCG, cordycepin, and tyrphostin AG1478.

A composition according to claim 10, comprising the following: scutellarein, luteolin, baicalein, kaempferol, resveratrol, and EGCG.

A composition according to claim 10, comprising the following: scutellarein, luteolin, baicalein, kaempferol, quercetin, resveratrol, EGCG, cordycepin, and tyrphostin AG1478.

A composition according to claim 1, wherein the granin comprises one or more of the following: chromogranin A (CGA), chromogranin B (CGB), secretogranin II (SgII) and secretogranin III (SgIII).

A composition according to claim 10, further comprising one or more agent that reduces, inhibits, suppress, or sequesters a metal ion selected from Zn2+, Cu2+, Fe2+ and Ca2+ in the nervous system of an animal.

A composition according to claim 10 further comprising a chelator of a metal ion selected from Zn2+, Cu2+, Fe2+.

A composition according to claim 10, wherein the composition is effective to inhibit the aggregation of a granin from a low molecular weight form to a high molecular weight aggregated form and/or to dissociate a high molecular weight aggregated form to a low molecular weight form in an animal.

A composition for inhibiting the interaction of granins with metal ions, the composition comprising i) an anthoxanthin selected from scutellarein, luteolin, baicalein, kaempferol, quercetin, apigenin, tangeretin, myricetin, fisetin, morin, and ii) a stilbenoid selected from resveratrol, piceatannolin, pinosylvin, pterostilbene, astringin, piceid, iii) a flavan selected from epigallocatechin 3-gallate (EGCG), catechin, gallocatechin, catechin 3-gallate, gallocatechin 3-gallate, epicatechin, epigallocatechin, epicatechin 3-gallate, theaflavin-3-gallate, theaflavin-3'-gallate, theaflavin-3,3'-gallate, thearubigin, and proanthocyanidins. and iv) a compound selected from cordycepin, tyrphostin AG1478, and 5,7-dimethoxyflavone.

A pharmaceutical composition for the treatment or prevention of dementia or Alzheimer's disease comprising a composition for inhibiting the aggregation of a granin from a low molecular weight form to a high molecular weight aggregated form.

A pharmaceutical composition for the treatment or prevention of dementia or Alzheimers disease, the composition comprising at least two of the following: scutellarein, luteolin, baicalein, kaempferol, quercetin, apigenin, tangeretin, myricetin, fisetin, resveratrol, EGCG, cordycepin, and tyrphostin AG1478.

A pharmaceutical composition according to claim 19, comprising at least four of the following: scutellarein, luteolin, baicalein, kaempferol, quercetin, apigenin, tangeretin, myricetin, fisetin, morin, resveratrol, EGCG, cordycepin, 5,7-dimethoxyflavone, and tyrphostin AG1478.

A pharmaceutical composition according to claim 19, comprising the following: scutellarein, luteolin, baicalein, kaempferol, apigenin, tangeretin, myricetin, fisetin, morin, resveratrol, and EGCG.

A pharmaceutical composition according to claim 19, comprising the following: scutellarein, luteolin, baicalein, kaempferol, quercetin, apigenin, tangeretin, myricetin, fisetin, morin, resveratrol, EGCG, cordycepin, 5,7-dimethoxyflavone, and tyrphostin AG1478.

A pharmaceutical composition according to claim 19, wherein the granin comprises one or more of the following: chromogranin A (CGA), chromogranin B (CGB), secretogranin II (SgII) and secretogranin III (SgIII).

A pharmaceutical composition according to claim 19, further comprising one or more agent that reduces, inhibits, suppress, or sequesters a metal ion selected from Zn2+, Cu2+, Fe2+ and Ca2+ in the nervous system of an animal.

A pharmaceutical composition according to claim 19 further comprising a chelator of a metal ion selected from Zn2+, Cu2+, or Fe2+.

A pharmaceutical composition according to claim 19, wherein the composition is effective to inhibit the aggregation of a granin from a low molecular weight form to a high molecular weight aggregated form in an animal.

A pharmaceutical composition for the treatment or prevention of dementia or Alzheimers disease, the composition comprising i) an anthoxanthin selected from scutellarein, luteolin, baicalein, kaempferol, quercetin, apigenin, tangeretin, myricetin, fisetin, morin, and ii) a stilbenoid selected from resveratrol, piceatannolin, pinosylvin, pterostilbene, astringin, piceid, iii) a flavan selected from epigallocatechin 3-gallate (EGCG), catechin, gallocatechin, catechin 3-gallate, gallocatechin 3-gallate, epicatechin, epigallocatechin, epicatechin 3-gallate, theaflavin-3-gallate, theaflavin-3'-gallate, theaflavin-3,3'-gallate, thearubigin, and proanthocyanidins. and iv) a compound selected from cordycepin, tyrphostin AG1478, and 5,7-dimethoxyflavone.

A method of reducing or inhibiting cell toxicity, the method comprising administering a composition for inhibiting the aggregation of a granin from a low molecular weight form to a high molecular weight aggregated form.

A method of reducing or inhibiting cell toxicity, the method comprising administering a composition for inhibiting the aggregation of a granin from a low molecular weight form to a high molecular weight aggregated form, wherein the composition comprises at least four of the following: scutellarein, luteolin, baicalein, kaempferol, resveratrol, and EGCG.

A method for the treatment or prevention of dementia or Alzheimer's disease, the method comprising administering an effective amount of a pharmaceutical composition for inhibiting the aggregation of a granin from a low molecular weight form to a high molecular weight aggregated form, the composition comprising at least two of the following: scutellarein, luteolin, baicalein, kaempferol, quercetin, resveratrol, EGCG, cordycepin, 5,7-dimethoxyflavone, and tyrphostin AG1478.

A method according to claim 30, wherein the pharmaceutical composition comprises at least four of the following: scutellarein, luteolin, baicalein, kaempferol, quercetin, resveratrol, EGCG, cordycepin, and tyrphostin AG1478.

A method according to claim 30, wherein the pharmaceutical composition comprises the following: scutellarein, luteolin, baicalein, kaempferol, resveratrol, and EGCG.

A method according to claim 30, wherein the pharmaceutical composition comprises the following: scutellarein, luteolin, baicalein, kaempferol, quercetin, resveratrol, EGCG, cordycepin, 5,7-dimethoxyflavone, and tyrphostin AG1478.

A method according to claim 30, wherein the pharmaceutical composition comprises a granin including one or more of the following: chromogranin A (CGA), chromogranin B (CGB), secretogranin II (SgII) and secretogranin III (SgIII).

A method according to claim 30, wherein the pharmaceutical composition further comprises one or more agent that reduces, inhibits, suppress, or sequesters a metal ion selected from Zn2+, Cu2+, Fe2+ and Ca2+ in the nervous system of an animal.

A method according to claim 30, wherein the pharmaceutical composition further comprises a chelator of a metal ion selected from Zn2+, Cu2+, or Fe2+.

A method according to claim 30, wherein the method is effective to inhibit the aggregation of a granin from a low molecular weight form to a high molecular weight aggregated form and/or to dissociate a high molecular weight aggregated form to a low molecular weight form in an animal.

A method for the treatment or prevention of dementia or Alzheimer's disease, the method comprising administering an effective amount of a pharmaceutical composition comprising: i) an anthoxanthin selected from scutellarein, luteolin, baicalein, kaempferol, quercetin, apigenin, tangeretin, myricetin, fisetin, morin, and ii) a stilbenoid selected from resveratrol, piceatannolin, pinosylvin, pterostilbene, astringin, piceid, iii) a flavan selected from epigallocatechin 3-gallate (EGCG), catechin, gallocatechin, catechin 3-gallate, gallocatechin 3-gallate, epicatechin, epigallocatechin, epicatechin 3-gallate, theaflavin-3-gallate, theaflavin-3'-gallate, theaflavin-3,3'-gallate, thearubigin, and proanthocyanidins. and iv) a compound selected from cordycepin, tyrphostin AG1478, and 5,7-dimethoxyflavone.

A method according to claim 38, wherein the pharmaceutical composition comprises at least four of the following: scutellarein, luteolin, baicalein, kaempferol, quercetin, apigenin, tangeretin, myricetin, fisetin, morin, resveratrol, EGCG, cordycepin, 5,7-dimethoxyflavone, and tyrphostin AG1478.

A method according to claim 38, wherein the pharmaceutical composition comprises the following: scutellarein, luteolin, baicalein, kaempferol, apigenin, tangeretin, myricetin, fisetin, morin, resveratrol, and EGCG.

A method according to claim 38, wherein the pharmaceutical composition comprises the following: scutellarein, luteolin, baicalein, kaempferol, quercetin, apigenin, tangeretin, myricetin, fisetin, morin, resveratrol, EGCG, cordycepin, 5,7-dimethoxyflavone, and tyrphostin AG1478.

A method according to claim 38, wherein the pharmaceutical composition comprises a granin including one or more of the following: chromogranin A (CGA), chromogranin B (CGB), secretogranin II (SgII) and secretogranin III (SgIII).

A method according to claim 38, wherein the pharmaceutical composition further comprises one or more agent that reduces, inhibits, suppress, or sequesters a metal ion selected from Zn2+, Cu2+, Fe2+ and Ca2+ in the nervous system of an animal.

A method according to claim 38, wherein the pharmaceutical composition further comprises a chelator of a metal ion selected from Zn2+, Cu2+, or Fe2+.

A method according to claim 38, wherein the method is effective to inhibit the aggregation of a granin from a low molecular weight form to a high molecular weight aggregated form in an animal.

A method for the treatment or prevention of dementia or Alzheimer's disease in a subject, the method comprising administering an effective amount of a pharmaceutical composition comprising one or more agent that reduces, inhibits, suppress, or sequesters a metal ion selected from $Zn^{2+}$, $Cu^{2+}$, $Fe^{2+}$ and $Ca^{2+}$ in the nervous system of the subject.

A method according to claim 46, wherein the pharmaceutical composition comprises at least four of the following: scutellarein, luteolin, baicalein, kaempferol, quercetin, apigenin, tangeretin, myricetin, fisetin, morin, resveratrol, EGCG, cordycepin, 5,7-dimethoxyflavone, and tyrphostin AG1478.

A method according to claim 46, wherein the pharmaceutical composition comprises the following: scutellarein, luteolin, baicalein, kaempferol, resveratrol, and EGCG.

A method according to claim 46, wherein the pharmaceutical composition comprises the following: scutellarein, luteolin, baicalein, kaempferol, quercetin, resveratrol, EGCG, cordycepin, 5,7-dimethoxyflavone, and tyrphostin AG1478.

A method according to claim 46, wherein the pharmaceutical composition comprises a granin including one or more of the following: chromogranin A (CGA), chromogranin B (CGB), secretogranin II (SgII) and secretogranin III (SgIII).

A method according to claim 46, wherein the pharmaceutical composition further comprises one or more agent that reduces, inhibits, suppress, or sequesters a metal ion selected from $Zn^{2+}$, $Cu^{2+}$, $Fe^{2+}$ and $Ca^{2+}$ in the nervous system of an animal.

A method according to claim 46, wherein the pharmaceutical composition further comprises a chelator of a metal ion selected from $Zn^{2+}$, $Cu^{2+}$, or $Fe^{2+}$.

A method according to claim 46, wherein the method is effective to inhibit the aggregation of a granin from a low molecular weight form to a high molecular weight aggregated form in an animal.

A method of screening Alzheimer's Disease drug candidates, the method comprising selecting a drug candidate based on it's ability to inhibit and/or suppress the aggregation of one or more granin induced by a metal ion selected from $Zn^{2+}$, $Cu^{2+}$, $Fe^{2+}$, and $Ca^{2+}$, or to dissociate aggregated granins.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A method for inhibiting the aggregation of a granin from a low molecular weight form to a high molecular weight aggregated form in a subject, comprising
administering to a subject in need thereof a composition, the composition comprising:
i) at least one anthoxanthin selected from the group consisting of scutellarein, luteolin, baicalein, kaempferol, quercetin, apigenin, tangeretin, myricetin, fisetin, and morin,
ii) at least one stilbenoid selected from the group consisting of resveratrol, piceatannolin, pinosylvin, pterostilbene, astringin, and piceid,
iii) at least one flavan selected from the group consisting of epigallocatechin 3-gallate (EGCG), catechin, gallocatechin, catechin 3-gallate, gallocatechin 3-gallate, epicatechin, epigallocatechin, epicatechin 3-gallate, theaflavin-3-gallate, theaflavin-3'-gallate, theaflavin-3, 3'-gallate, thearubigin, and proanthocyanidins, and
iv) at least one compound selected from the group consisting of cordycepin, tyrphostin AG1478, and 5,7-dimethoxyflavone.

2. The method according to claim 1, wherein the composition comprises scutellarein, luteolin, baicalein, kaempferol, quercetin, resveratrol, EGCG, cordycepin, and tyrphostin AG1478.

3. The method according to claim 1, wherein the granin comprises one or more of the following: chromogranin A (CGA), chromogranin B (CGB), secretogranin II (SgII) and secretogranin III (SgIII).

4. The method according to claim 1, further comprising administering one or more agent that reduces, inhibits, suppress, or sequesters one or more of $Zn^{2+}$, $Cu^{2+}$, $Fe^{2+}$ and $Ca^{2+}$ in a nervous system of the subject,
wherein the agent is selected from the group consisting of $Zn^{2+}$ binding and sequestering molecules, zinc finger transcription factors, $Cu^{2+}$ binding and sequestering molecules, ceruloplasmin, casein, albumin, $Fe^{2+}$ binding and sequestering molecules, calmodulin, troponin, ferritin, transferrin, lactoferrin, and anthocyanin.

5. The method according to claim 1 further comprising administering a chelator of a metal ion selected from the group consisting of $Zn^{2+}$, $Cu^{2+}$, and $Fe^{2+}$.

6. The method according to claim 1, wherein the method dissociates the high molecular weight aggregated form to the low molecular weight form.

7. The method according to claim 1, wherein the method inhibits the interaction of the granin with metal ions.

8. The method according to claim 1, wherein the method treats or prevents dementia or Alzheimer's disease, and the subject suffers from the dementia or the Alzheimer's disease.

* * * * *